(12) United States Patent
Lu et al.

(10) Patent No.: US 10,494,359 B2
(45) Date of Patent: Dec. 3, 2019

(54) COMPOUND AND ORGANIC ELECTRONIC DEVICE USING THE SAME

(71) Applicant: NICHEM FINE TECHNOLOGY CO., LTD., Jhubei, Hsinchu County (TW)

(72) Inventors: Tai-Ni Lu, Jhubei (TW); Hui-Ling Wu, Jhubei (TW); Shwu-Ju Shieh, Jhubei (TW); Chi-Chung Chen, Jhubei (TW)

(73) Assignee: SHANGHAI NICHEM FINE CHEMICAL CO., LTD., Shanghai (CN)

( * ) Notice: Subject to any disclaimer, the term of this patent is extended or adjusted under 35 U.S.C. 154(b) by 183 days.

(21) Appl. No.: 15/712,870

(22) Filed: Sep. 22, 2017

(65) Prior Publication Data

US 2019/0092745 A1    Mar. 28, 2019

(51) Int. Cl.
*C07D 335/12*    (2006.01)
*C07D 311/96*    (2006.01)
(Continued)

(52) U.S. Cl.
CPC .......... *C07D 335/12* (2013.01); *C07D 311/96* (2013.01); *H01L 51/0071* (2013.01);
(Continued)

(58) Field of Classification Search
CPC ............ H01L 51/0073; H01L 51/0074; C07D 311/96; C07D 335/12
See application file for complete search history.

(56) References Cited

FOREIGN PATENT DOCUMENTS

| CN | 105778891 A | * | 7/2016 |
|----|-------------|---|--------|
| CN | 106467510 A |   | 3/2017 |

(Continued)

OTHER PUBLICATIONS

Computer-generated English-language translation of CN105778891A.*
SciFinder Search (May 20, 2019).*

*Primary Examiner* — Vu A Nguyen
(74) *Attorney, Agent, or Firm* — Birch, Stewart, Kolasch & Birch, LLP

(57) ABSTRACT

Provided are a novel compound and an organic electronic device using the same. The novel compound is represented by the following Formula (I):

Formula (I)

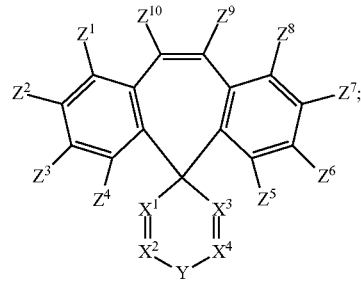

wherein Y is an oxygen atom or a sulfur atom; $X^1$ and $X^2$ are each independently $C(R^a)$, the two $(R^a)$s are the same or different, and the two $(R^a)$s are joined together to form a first aryl ring; $X^3$ and $X^4$ are each independently $C(R^b)$, the two $(R^b)$s are the same or different, and the two $(R^b)$s are joined to form a second aryl ring or a heteroaryl ring.

17 Claims, 18 Drawing Sheets

(51) Int. Cl.
 *H01L 51/00* (2006.01)
 *H01L 51/50* (2006.01)
(52) U.S. Cl.
 CPC ...... *H01L 51/0073* (2013.01); *H01L 51/0072* (2013.01); *H01L 51/5072* (2013.01)

(56) References Cited

FOREIGN PATENT DOCUMENTS

| CN | 106467544 A | * | 3/2017 |
| CN | 106467740 A | | 3/2017 |

\* cited by examiner

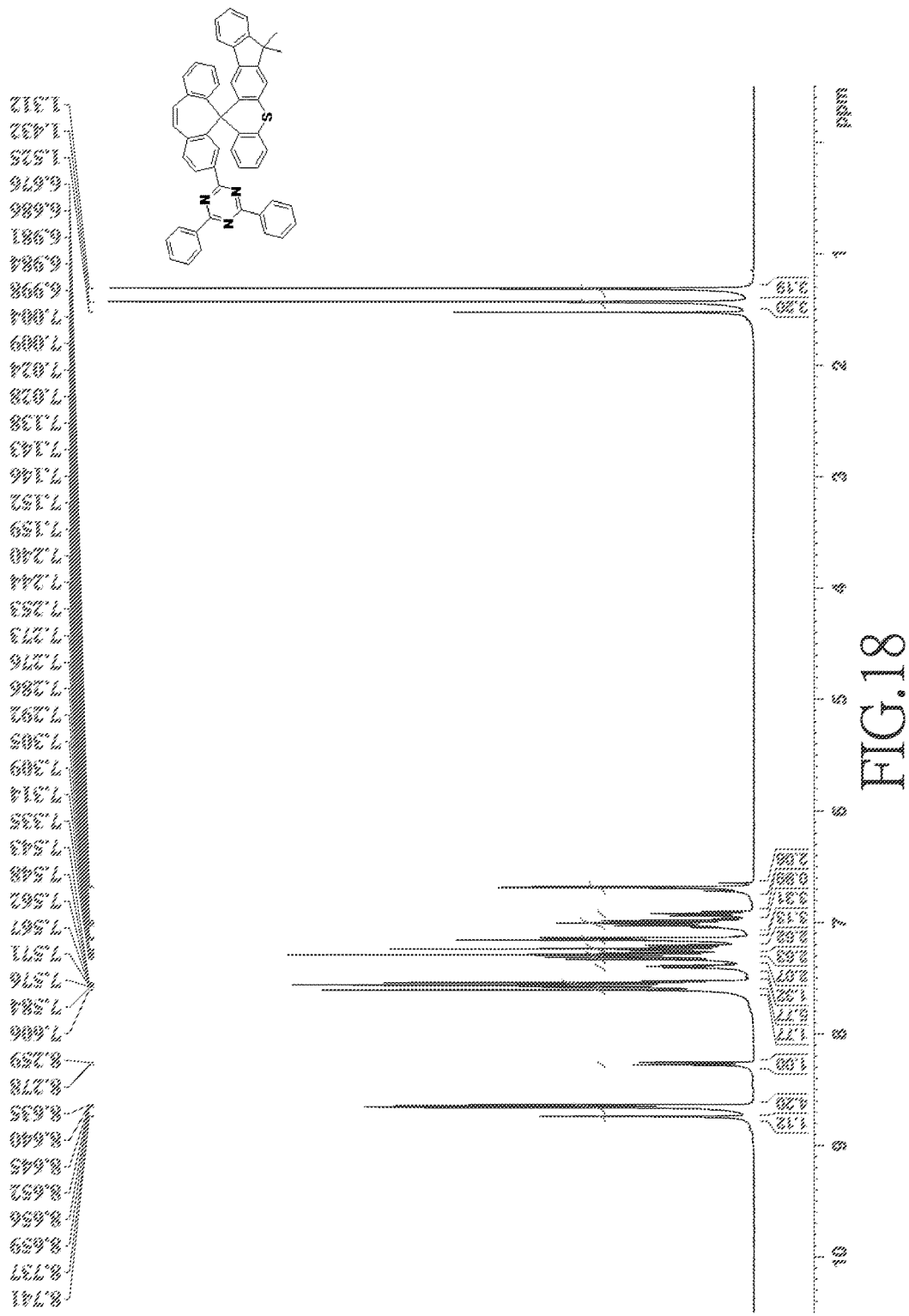

COMPOUND AND ORGANIC ELECTRONIC DEVICE USING THE SAME

BACKGROUND OF THE INVENTION

1. Field of the Invention

The present invention relates to a novel compound and an organic electronic device using the same, more particularly to a novel compound as electron-transporters and an organic electronic device using the same.

2. Description of the Prior Arts

With the advance of technology, various organic electronic devices that make use of organic materials have been energetically developed. Examples of organic electronic devices include organic light emitting devices (OLEDs), organic phototransistors, organic photovoltaic cells, and organic photodetectors.

OLED was initially invented and proposed by Eastman Kodak Company through a vacuum evaporation method. Dr. Ching W. Tang and Steven VanSlyke of Kodak Company deposited an electron transport material such as tris(8-hydroxyquinoline)aluminum(III) (abbreviated as Alq$_3$) on a transparent indium tin oxide glass (abbreviated as ITO glass) formed with a hole transport layer of organic aromatic diamine thereon, and subsequently deposited a metal electrode onto an electron transport layer to complete the fabrication of the OLED. OLEDs have attracted lots of attention due to their numerous advantages, such as fast response speed, light weight, compactness, wide viewing angle, high brightness, higher contrast ratio, no need of backlight, and low power consumption. However, the OLEDs still have the problems such as low efficiency and short lifetime.

To overcome the problem of low efficiency, one of the approaches is to interpose some interlayers between the cathode and the anode. With reference to FIG. 1, a modified OLED 1 may have a structure of a substrate 11, an anode 12, a hole injection layer 13 (abbreviated as HIL), a hole transport layer 14 (abbreviated as HTL), an emission layer 15 (abbreviated as EL), an electron transport layer 16 (abbreviated as ETL), an electron injection layer 17 (abbreviated as EIL), and a cathode 18 stacked in sequence. When a voltage is applied between the anode 12 and the cathode 18, the holes injected from the anode 12 move to the EL via HIL and HTL and the electrons injected from the cathode 18 move to the EL via EIL and ETL. Recombination of the electrons and the holes occurs in the EL to generate excitons, thereby emitting a light when the excitons decay from excited state to ground state.

Another approach is to modify the materials of ETL for OLEDs to render the electron transport materials to exhibit hole-blocking ability. Examples of conventional electron transport materials include 3,3'-[5'-[3-(3-Pyridinyl)phenyl][1,1':3',1''-terphenyl]-3,3''-diyl]bispyridine (TmPyPb), 1,3,5-tris(1-phenyl-1H-benzimidazol-2-yl)benzene (TPBi), tris(2,4,6-trimethyl-3-(pyridin-3-yl)phenyl)borane (3TPYMB), 1,3-bis(3,5-dipyrid-3-yl-phenyl)benzene (BmPyPb), 3-(Biphenyl-4-yl)-5-(4-tert-butylphenyl)-4-phenyl-4H-1,2,4-triazole (TAZ), and 9,10-bis(3-(pyridin-3-yl)phenyl)anthracene (DPyPA).

However, even using the foresaid electron transport materials, the current efficiency of OLEDs still needs to be improved. Therefore, the present invention provides a novel compound to mitigate or obviate the problems in the prior art.

SUMMARY OF THE INVENTION

An objective of the present invention is to provide a novel compound useful for an organic electronic device.

Another objective of the present invention is to provide an organic electronic device using the novel compound, so as to improve the efficiency of the organic electronic device.

To achieve the foresaid objectives, the present invention provides a novel compound represented by the following Formula (I):

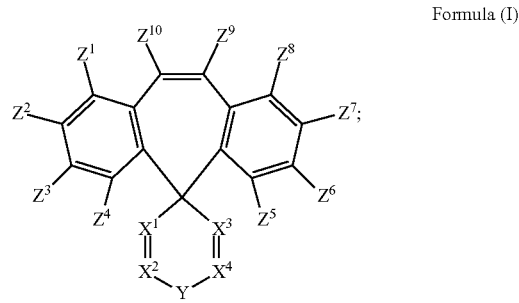

Formula (I)

In Formula (I), Y is an oxygen atom or a sulfur atom.

In Formula (I), $X^1$ and $X^2$ are each independently $C(R^a)$, the two $(R^a)$s are the same or different, and the two $(R^a)_s$ are joined together to form a first aryl ring.

In Formula (I), $X^3$ and $X^4$ are each independently $C(R^b)$, the two $(R^b)$s are the same or different, and the two $(R^b)$s are joined together to form a second aryl ring or a heteroaryl ring.

In Formula (I), $Z^1$ to $Z^{10}$ are each independently selected from the group consisting of: a hydrogen atom, a deuterium atom, a halogen group, a cyano group, a nitro group, a trifluoromethyl group, an alkyl group having 1 to 40 carbon atoms, an alkenyl group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

Preferably, the first aryl ring extended from $X^1$ and $X^2$ in Formula (I) and the second aryl ring extended from $X^3$ and $X^4$ in Formula (I) are each independently a substituted or unsubstituted 6 to 60-membered carbon ring, more preferably a substituted or unsubstituted 6 to 20-membered carbon ring. For example, the substituted or unsubstituted 6 to 60-membered carbon ring may be selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted pyrene ring, a substituted or unsubstituted fluoranthene ring, a substituted or unsubstituted benzofluoranthene ring, and a substituted or unsubstituted fluorene ring, but it is not limited thereto. More preferably, the substituted or unsubstituted 6 to 60-membered carbon ring is a substituted or unsubstituted benzene structure, a substituted or unsubstituted naphthalene ring or a substituted or unsubstituted fluorene ring. The substitution group on the 6 to 20-membered carbon ring may be, but not limited to, a halogen group, a cyano group, a nitro group, an alkyl group having 1 to 12 carbon atoms, an alkenyl group having 2 to 12 carbon atoms, or an alkynyl group having 2 to 12 carbon atoms.

Preferably, the heteroaryl ring extended from $X^3$ and $X^4$ in Formula (I) may contain at least one furan group or at least one thiophene group. For example, the heteroaryl ring may be, but not limited to, a substituted or unsubstituted dibenzofuran ring, a substituted or unsubstituted dibenzothiophene ring, a substituted or unsubstituted benzofuran ring, a substituted or unsubstituted isobenzofuran ring, a substituted or unsubstituted benzothiophene ring, or a substituted or unsubstituted isobenzothiophene ring.

Preferably, $Z^1$ to $Z^{10}$ are each independently selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 30 ring carbon atoms, an alkoxy group having 1 to 12 carbon atoms, an aryloxy group having 6 to 30 ring carbon atoms, an alkylsilyl group having 1 to 12 carbon atoms, an arylsilyl group having 6 to 30 ring carbon atoms, an alkylboron group having 1 to 12 carbon atoms, an arylboron group having 6 to 30 ring carbon atoms, a phosphine group having 1 to 12 carbon atoms, and a phosphine oxide group having 1 to 12 carbon atoms.

In a case that Y is an oxygen atom, the compound may be, for example, represented by Formula (I-I)

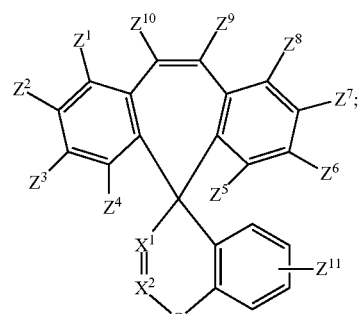

Formula (I-III)

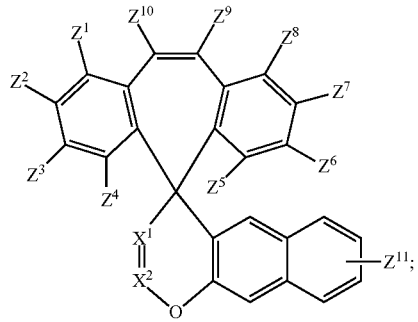

Formula (I-V)

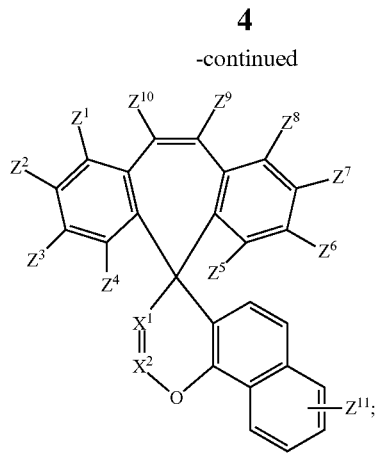

Formula (I-VII)

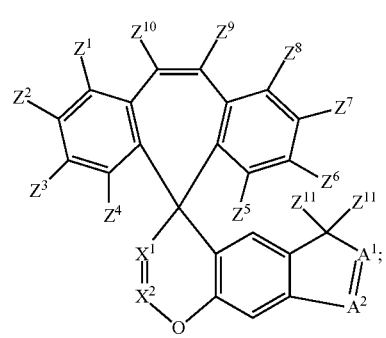

Formula (I-IX)

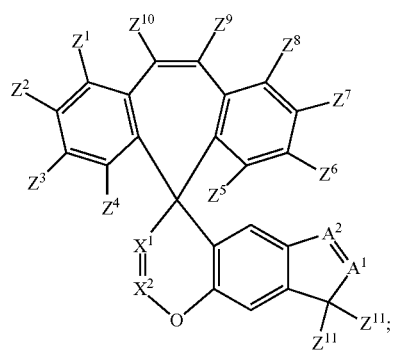

Formula (I-XI)

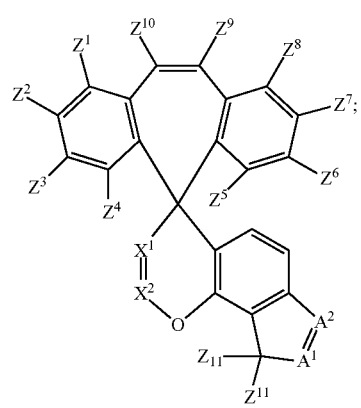

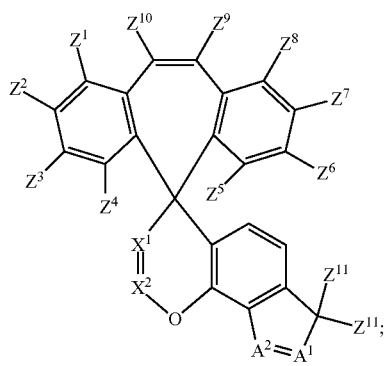
Formula (I-XIII)
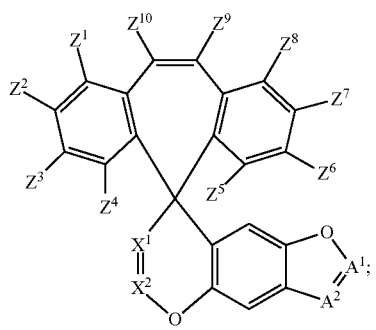
Formula (I-XV)
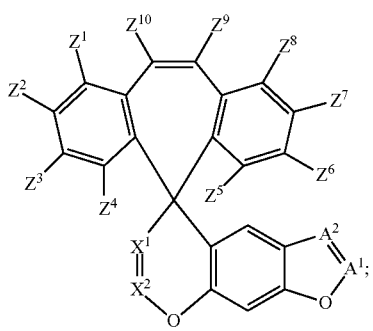
Formula (I-XVII)
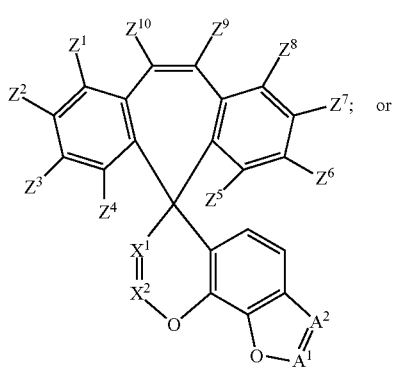
Formula (I-XIX) or
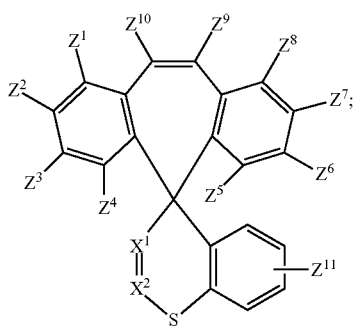
Formula (I-XXI)
In a case that Y is a sulfur atom, the compound may be, for example, represented by any one of the following Formulae:
Formula (I-II)
Formula (I-IV)
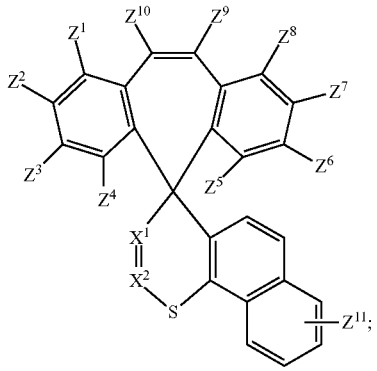
Formula (I-VI)

Formula (I-VIII)

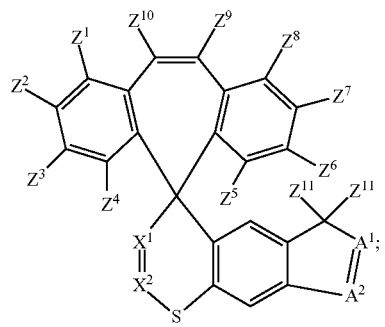

Formula (I-X)

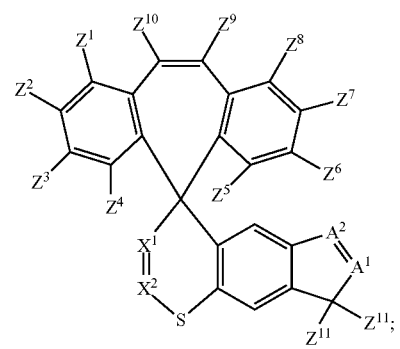

Formula (I-XII)

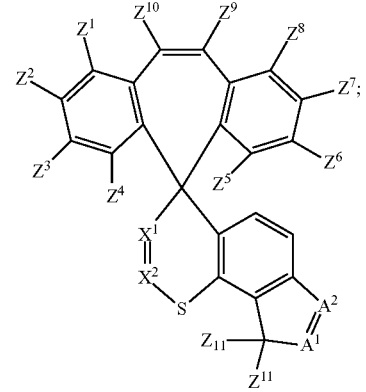

Formula (I-XIV)

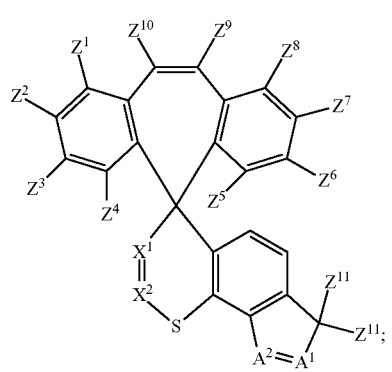

Formula (I-XVI)

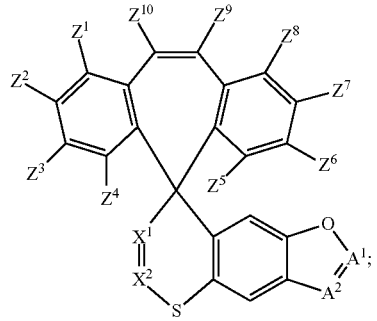

Formula (I-XVIII)

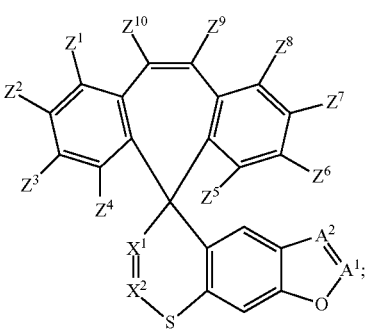

Formula (I-XX)

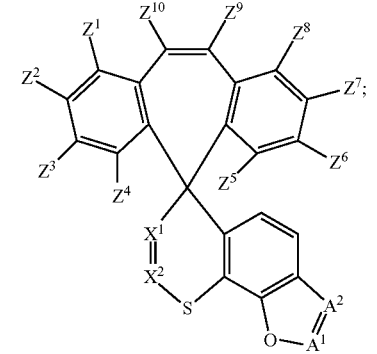

Formula (I-XXII)

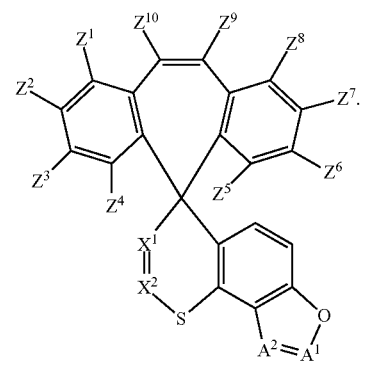

In accordance with the present invention, the foresaid $A^1$ and $A^2$ are each independently $C(R^c)$, and the two $(R^c)$s are the same or different. The two $(R^c)$s are joined together to form an aromatic structure contained in the second aryl ring or the heteroaryl ring.

In accordance with the present invention, each of the foresaid $Z^{11}$ is selected from the group consisting of: a methyl group, an ethyl group, a propyl group, a butyl group, a pentyl group, a hexyl group, and a phenyl group.

Preferably, the aromatic structure formed by the two (R<sup>c</sup>)s may be a substituted or unsubstituted 6 to 20-membered carbonaromatic cyclic structure, for example, but not limited to, a substituted or unsubstituted benzene structure, a substituted or unsubstituted naphthalene structure, a substituted or unsubstituted anthracene structure, a substituted or unsubstituted phenanthrene structure, a substituted or unsubstituted pyrene structure, a substituted or unsubstituted fluoranthene structure, a substituted or unsubstituted benzofluoranthene structure, or a substituted or unsubstituted fluorene structure. The substitution group on the 6 to 20-membered carbon aromatic cyclic structure may be, but not limited to, a halogen group, a cyano group, a nitro group, a trifluoromethyl group, an alkyl group having 1 to 12 carbon atoms, an alkenyl group having 2 to 12 carbon atoms, or an alkynyl group having 2 to 12 carbon atoms.

Preferably, at least one of $Z^1$ to $Z^8$ in formula (I) may be selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to carbon atoms and substituted with at least one functional group, an arylboron group having 6 to 60 ring carbon atoms, a phosphine group having 1 to 40 carbon atoms and substituted with at least one functional group, and a phosphine oxide group having 1 to 40 carbon atoms and substituted with at least one functional group; and the other(s) of $Z^1$ to $Z^8$ in Formula (I) may be any other substitution groups as mentioned in the specification. Said functional group is selected from the group consisting of: a cyano group, a nitro group, a trifluoromethyl group, a fluoro group, and a chloro group.

More specifically, at least one of $Z^1$ to $Z^8$ in Formula (I) may be a specific aromatic substitution. The specific aromatic substitution may be selected from the group consisting of:

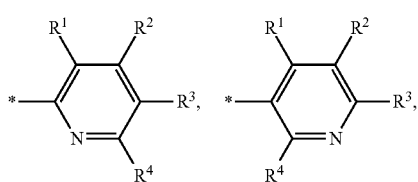

-continued

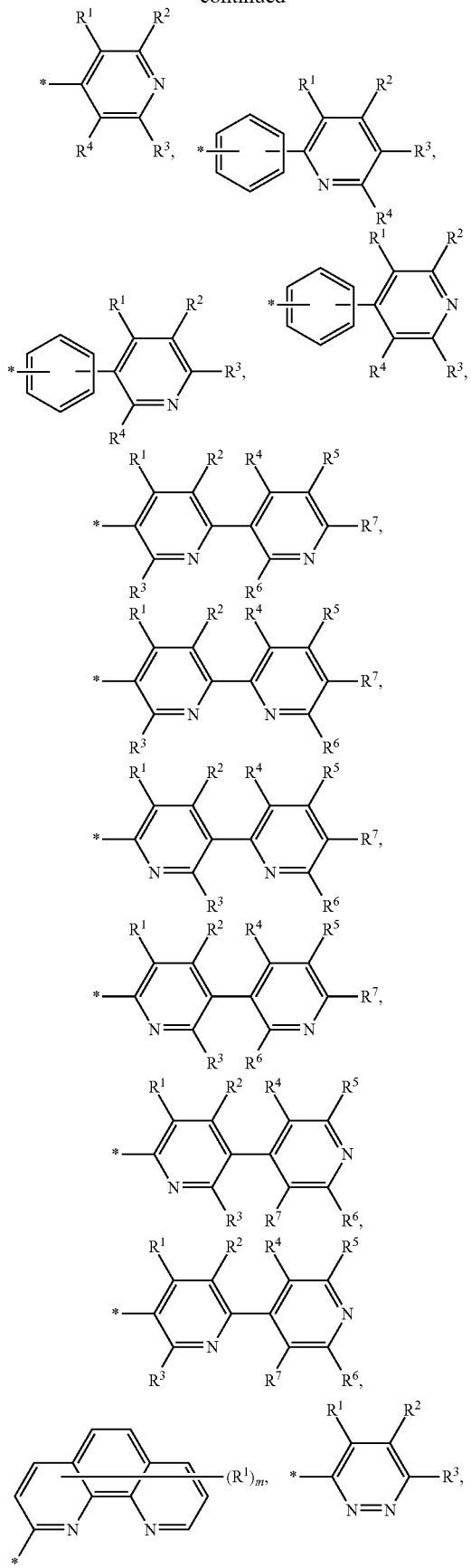

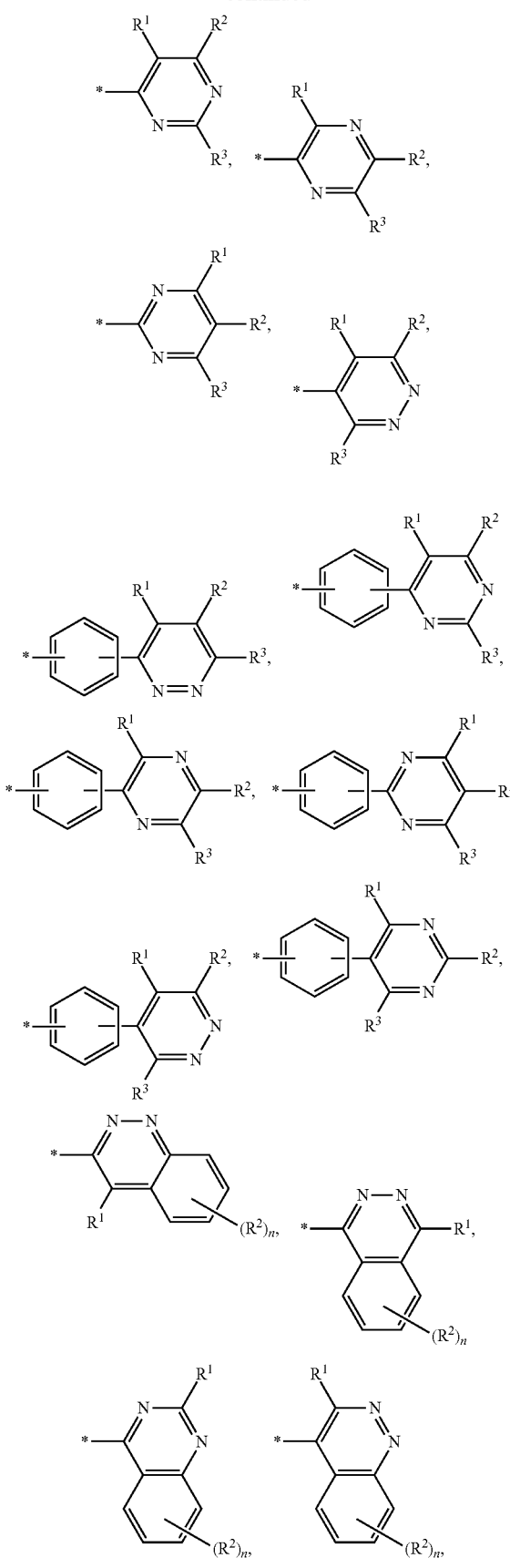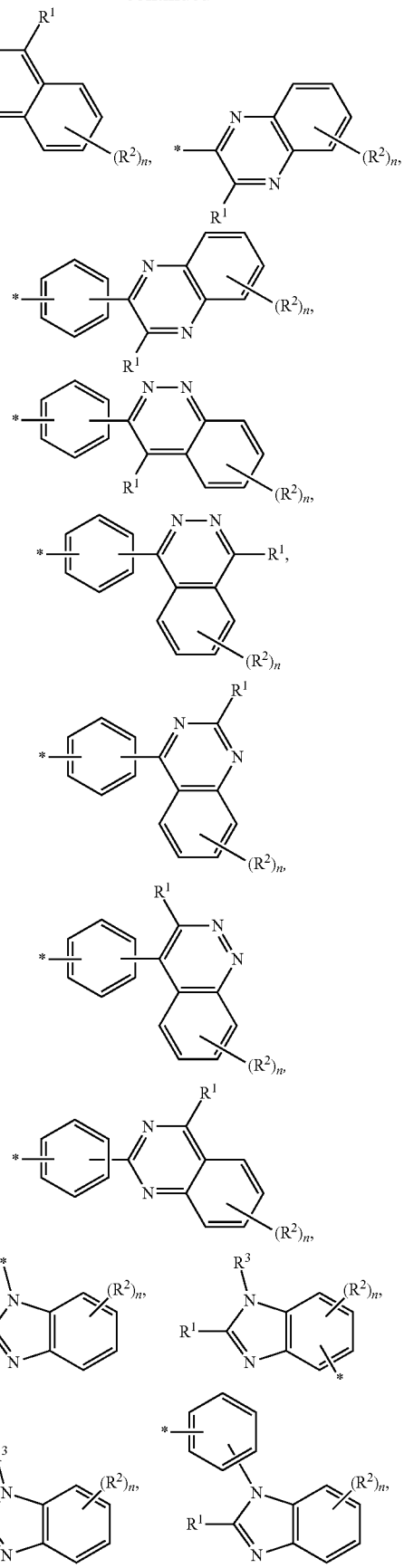

-continued

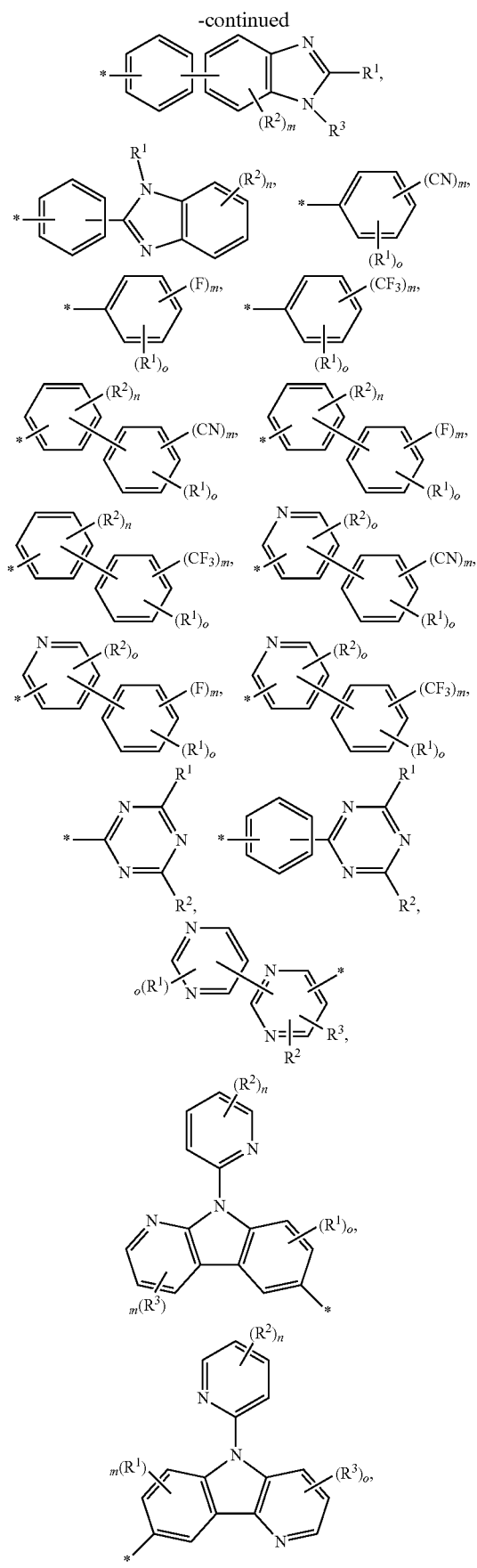

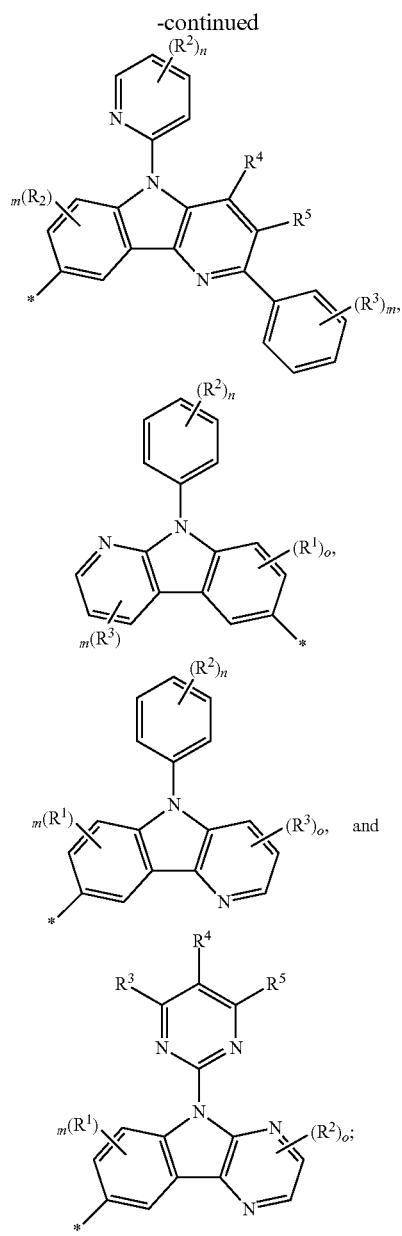

wherein $R^1$ to $R^7$ are each independently selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is an integer from 0 to 4, m is an integer from 0 to 3, o is an integer from 0 to 3, and the total of m and o is not more than 5.

Preferably, $R^1$ to $R^3$ each may independently be, for example, but not limited to, phenyl group, pyridine group, pyrimidine group, pyrazine group, pyridazine group, phenylpyridine group, phenylpyrimidine group, phenylpyrazine group, or phenylpyridazine group.

Preferably, at least one of $Z^1$, $Z^2$, $Z^3$, $Z^6$, $Z^7$, and $Z^8$ in Formula (I) may be the specific aromatic substitution as stated above, and $Z^4$ and $Z^5$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms. Or, at least one of $Z^2$, $Z^3$, $Z^6$, and $Z^7$ in Formula (I) may be the specific aromatic substitution as stated above, and $Z^1$, $Z^4$, $Z^5$, $Z^8$ are each independently selected from the group consisting of: a hydrogen atom, a deuterium atom, an alkyl group having 1 to 12 carbon atoms, an alkenyl group having 2 to 12 carbon atoms, and an alkynyl group having 2 to 12 carbon atoms.

Preferably, at least one of $Z^2$, $Z^3$, $Z^6$, and $Z^7$ in Formula (I) is selected from the group consisting of:

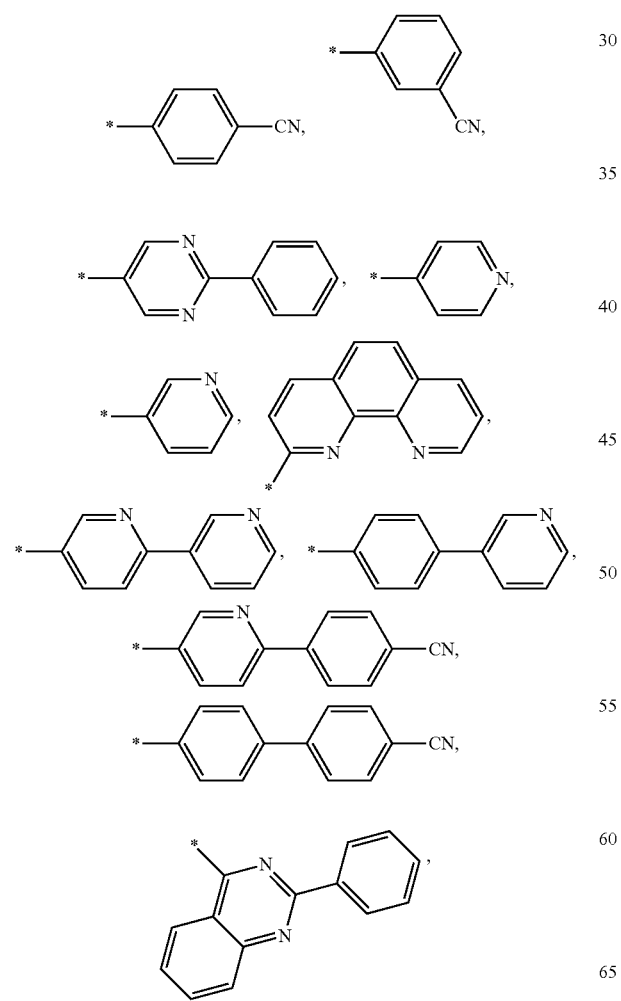

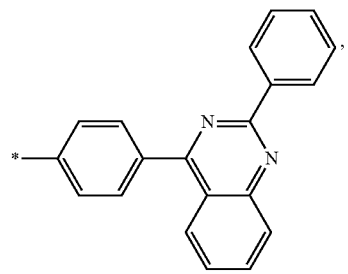

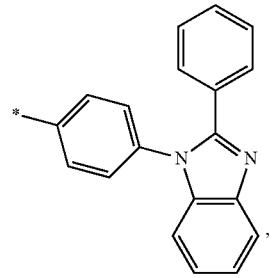

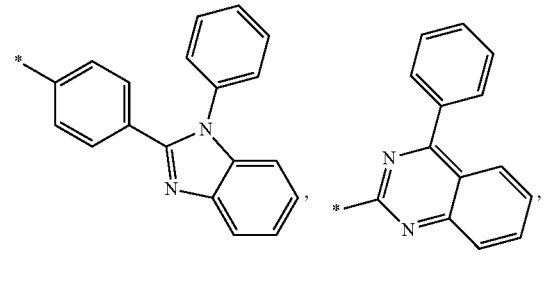

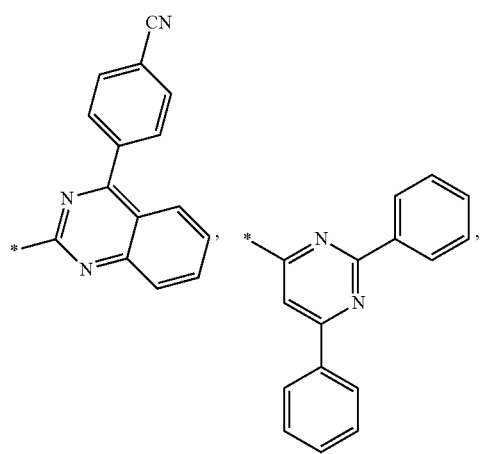

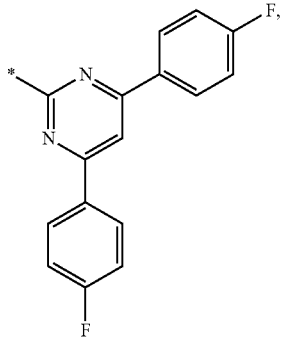

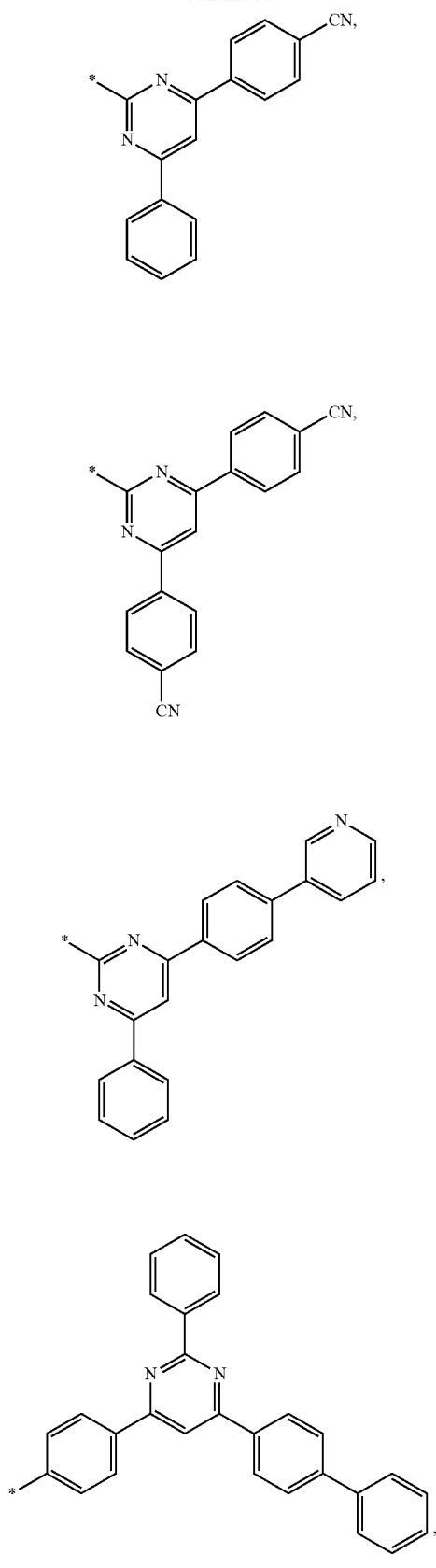
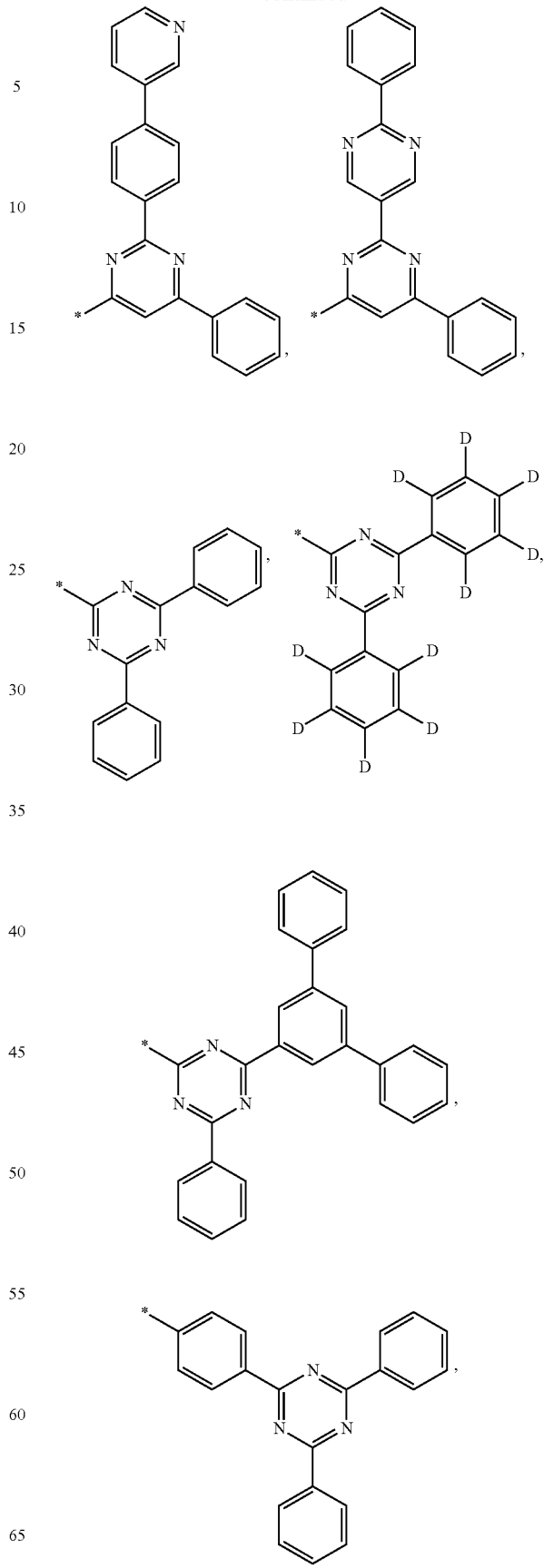

-continued

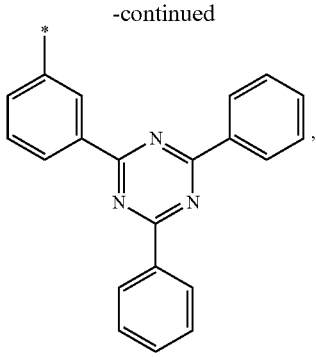

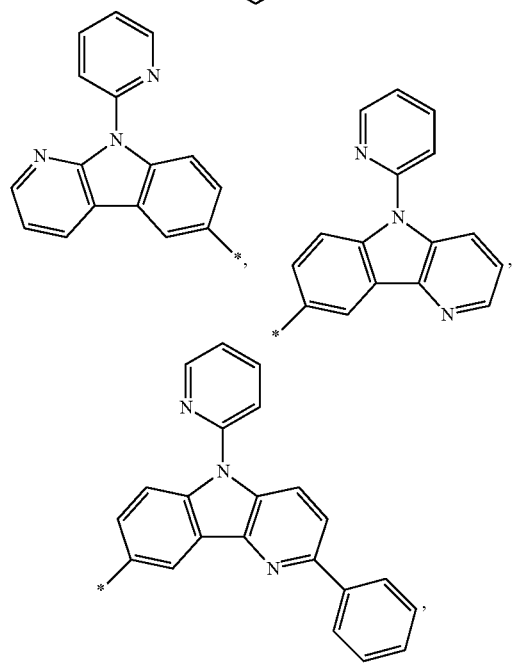

More preferably, at least one of $Z^1$, $Z^2$, $Z^3$, $Z^6$, $Z^7$, and $Z^8$ in Formula (I) may be a substituted triazine group with two phenyl groups, two pyridine groups, two pyrimidine groups, two pyrazine groups, two pyridazine groups, two phenylpyridine groups, two phenylpyrimidine groups, two phenylpyrazine groups, or two phenylpyridazine groups.

Preferably, $Z^9$ and $Z^{19}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

In accordance with the present invention, $Z^1$ and $Z^8$ may be the same or different. In accordance with the present invention, $Z^2$ and $Z^7$ may be the same or different. In accordance with the present invention, $Z^3$ and $Z^6$ may be the same or different. In one embodiment, any two of $Z^1$, $Z^2$, $Z^3$, $Z^6$, $Z^7$, and $Z^8$ may be the same substitution as stated above, and the others of $Z^1$, $Z^2$, $Z^3$, $Z^6$, $Z^7$, and $Z^8$ may be a hydrogen atom, a deuterium atom, a halogen group, a cyano group, a nitro group, an alkyl group having 1 to 12 carbon atoms, an alkenyl group having 2 to 12 carbon atoms, or an alkynyl group having 2 to 12 carbon atoms.

For example, the compound may be selected from the group consisting of:

Compound 1

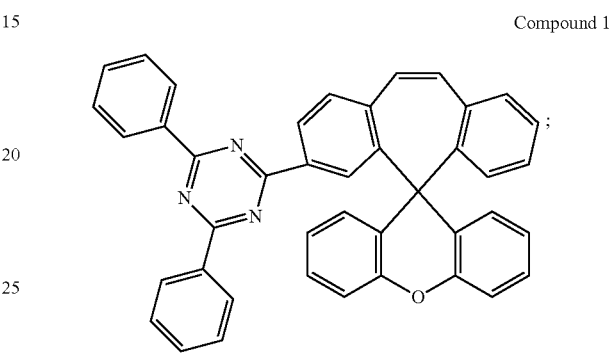

Compound 2

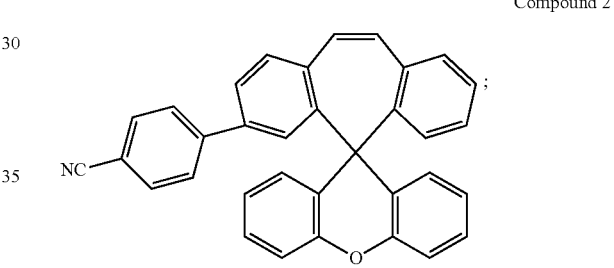

Compound 3

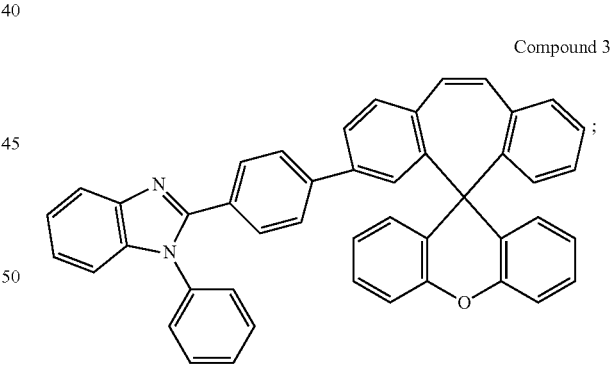

Compound 4

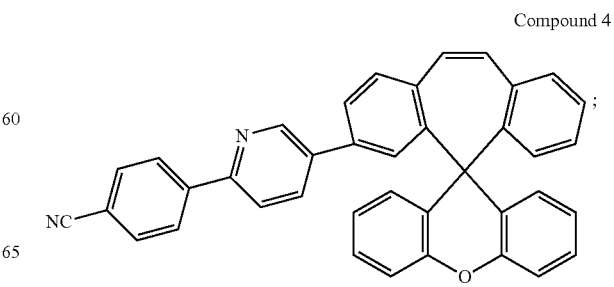

Compound 5
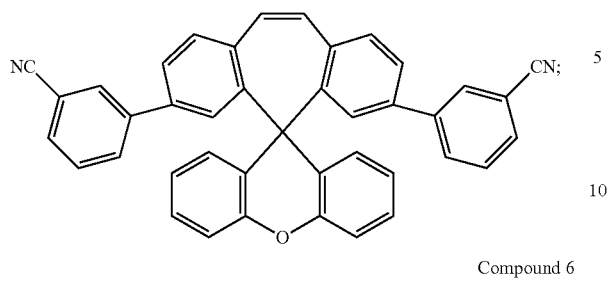
Compound 6
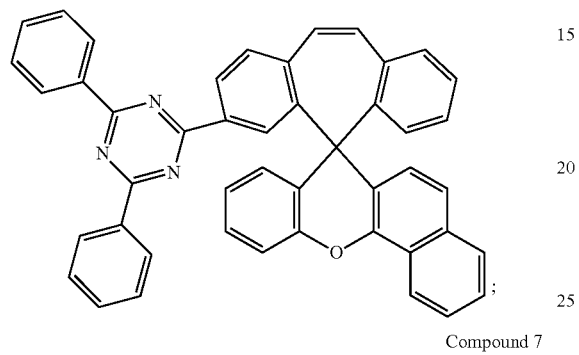
Compound 7
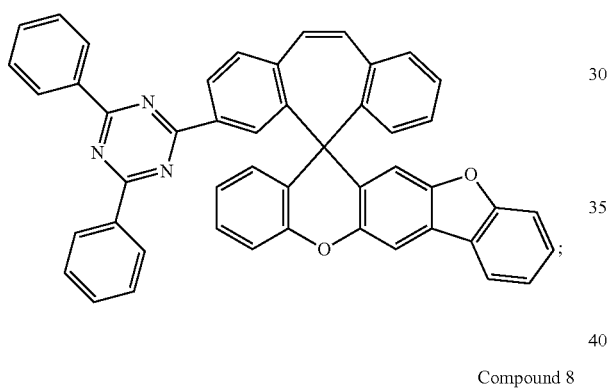
Compound 8
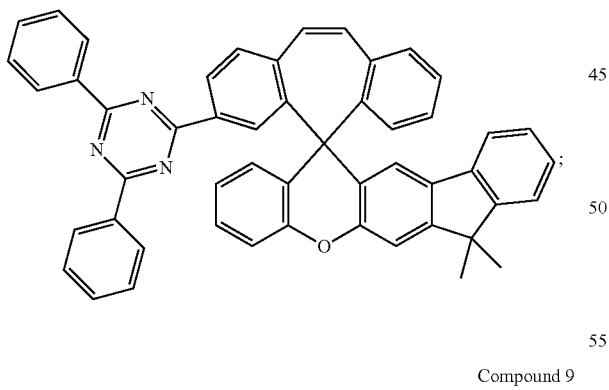
Compound 9
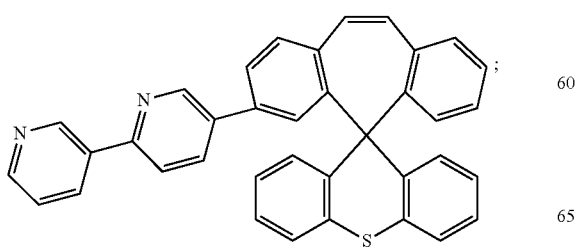
Compound 10
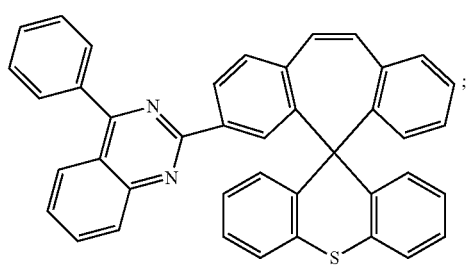
Compound 11
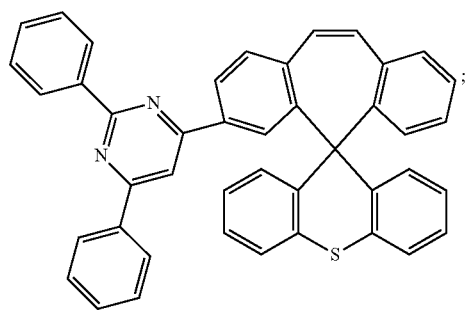
Compound 12
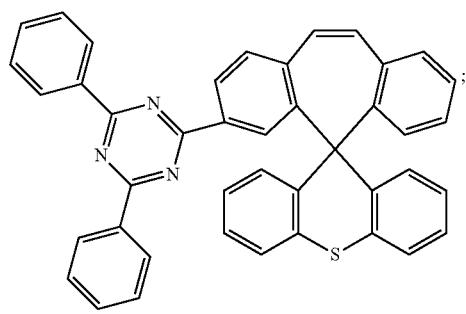
Compound 13
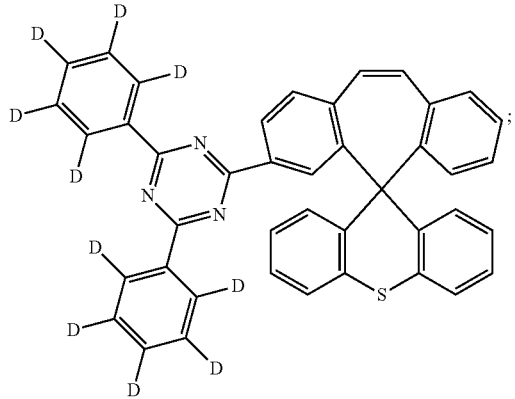

Compound 14
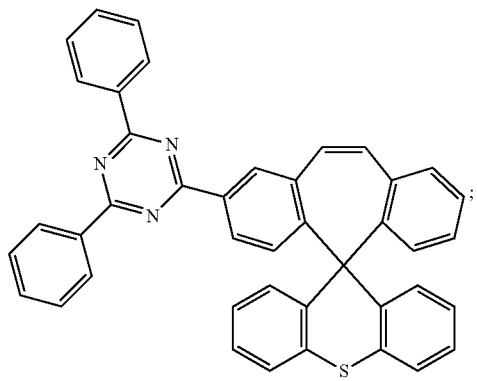
Compound 15
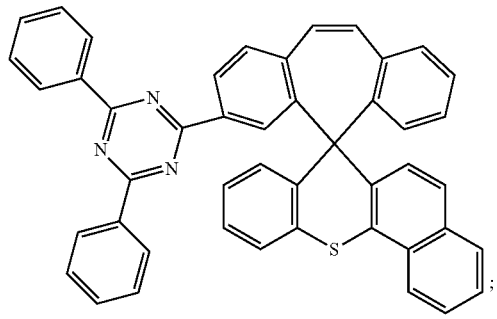
Compound 16
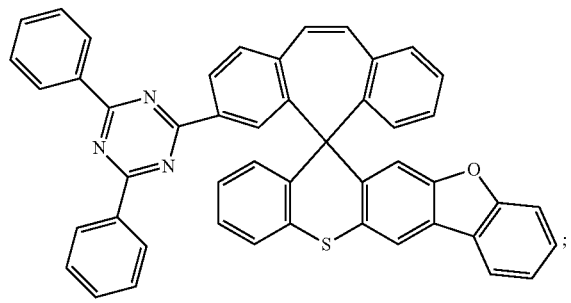
Compound 17
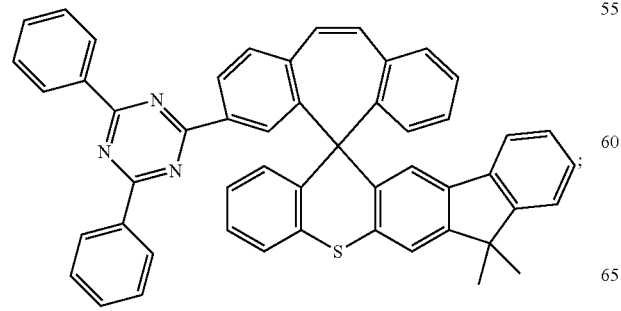
Compound 18
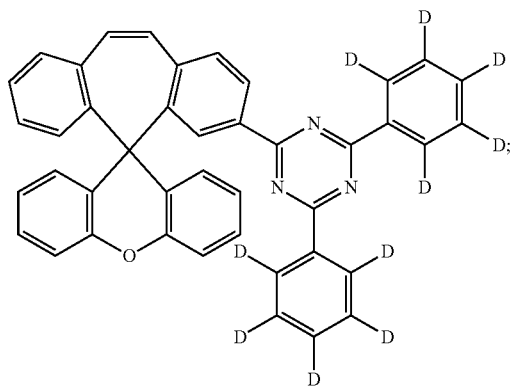
Compound 19
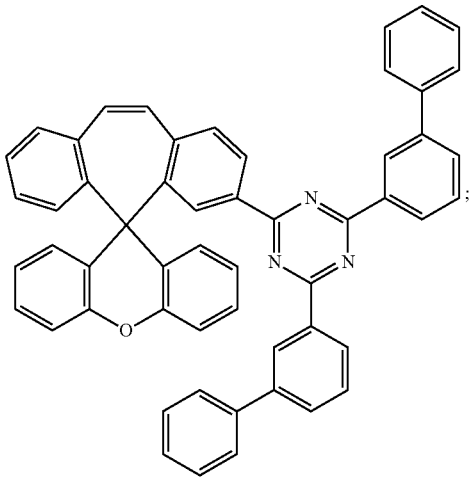
Compound 20
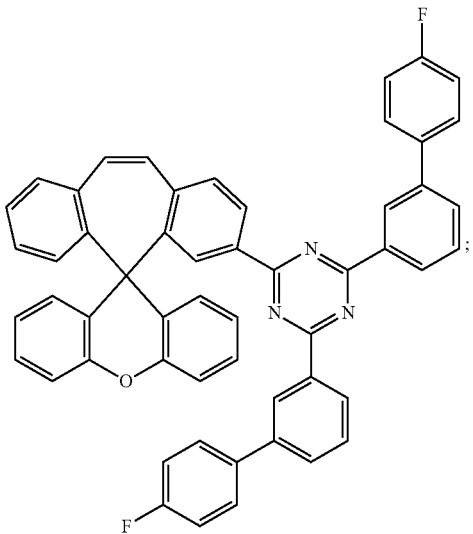

-continued
Compound 21
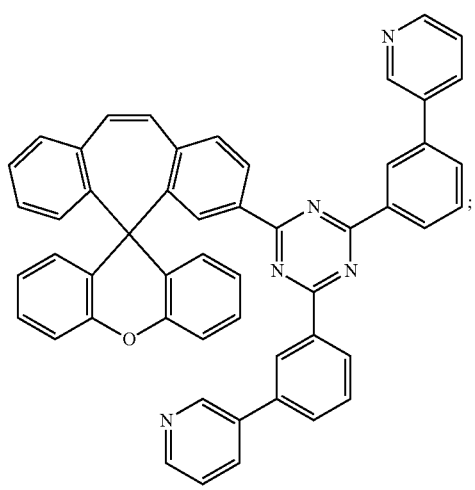
Compound 22
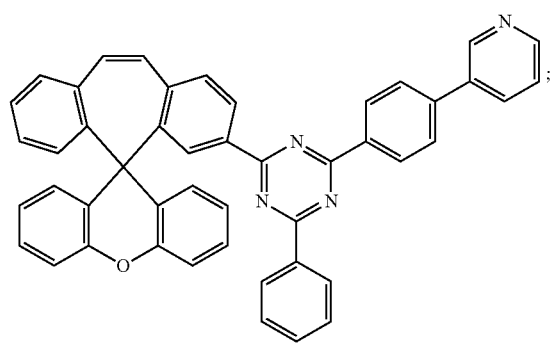
Compound 23
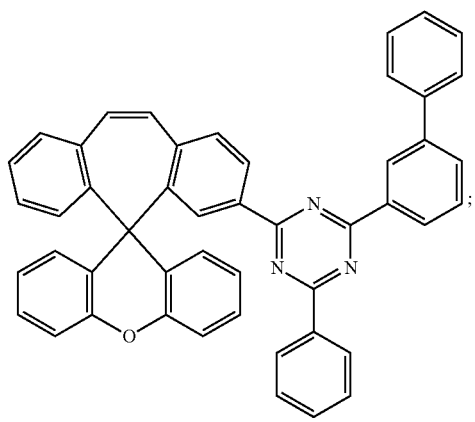
Compound 24
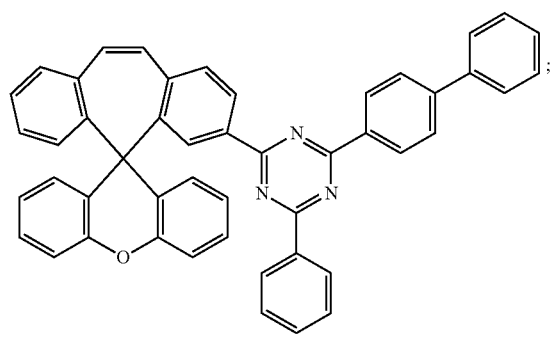
-continued
Compound 25
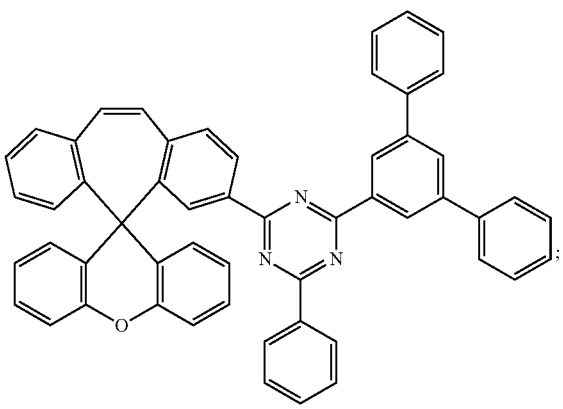
Compound 26
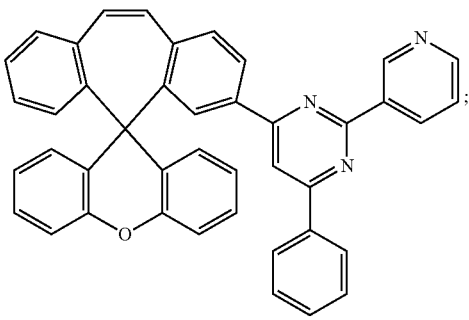
Compound 27
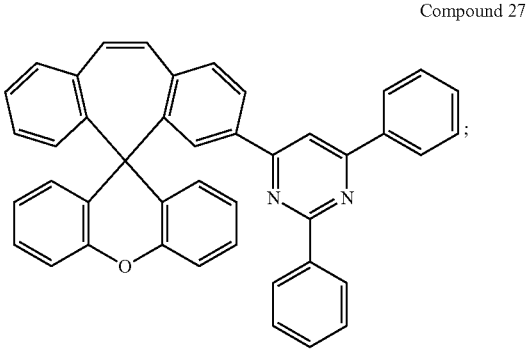
Compound 28
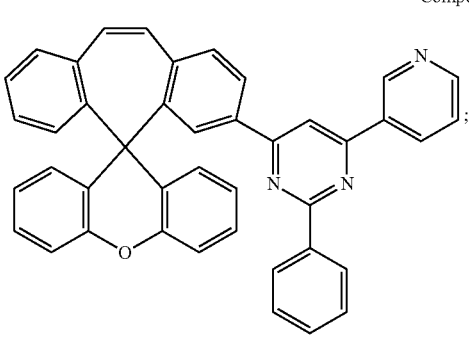

Compound 29
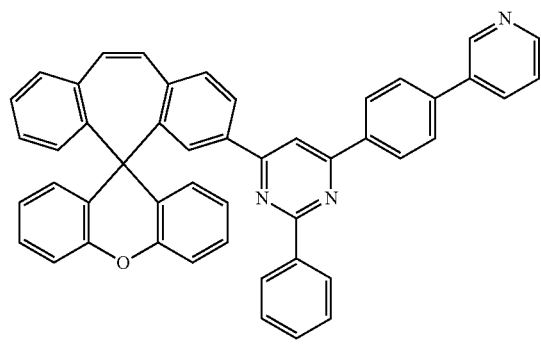
Compound 30
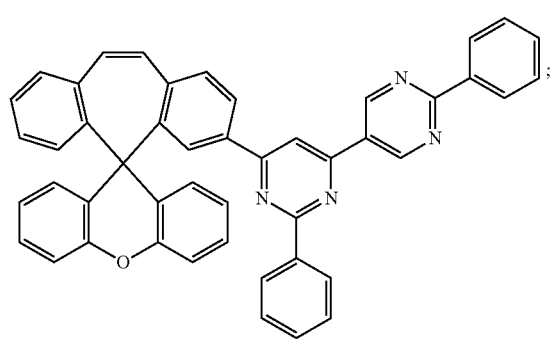
Compound 31
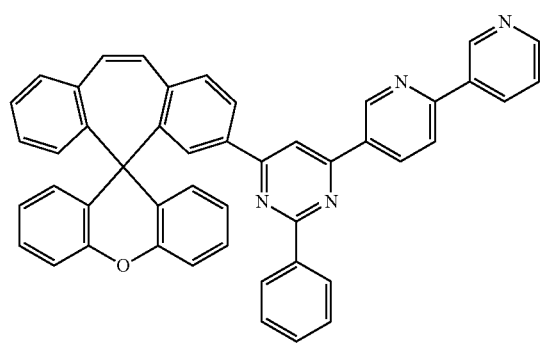
Compound 32
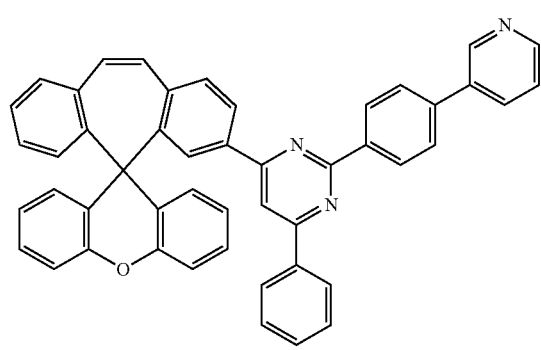
Compound 33
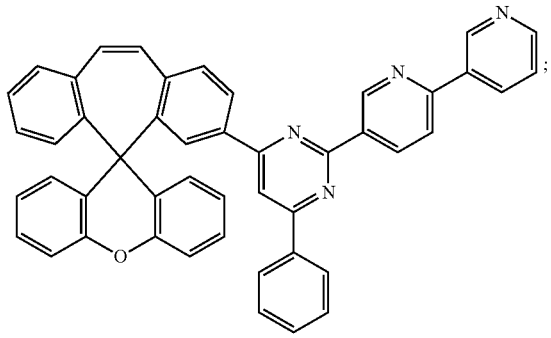
Compound 34
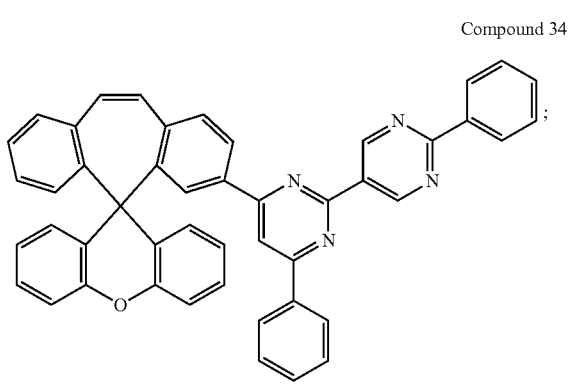
Compound 35
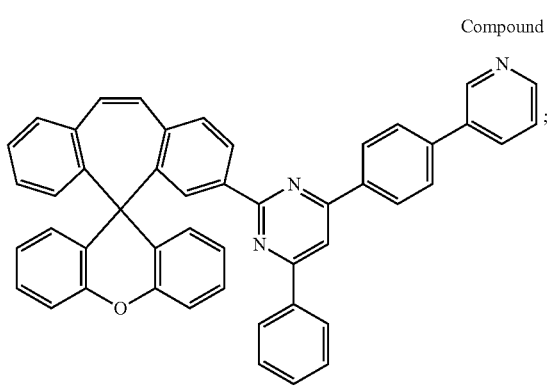
Compound 36
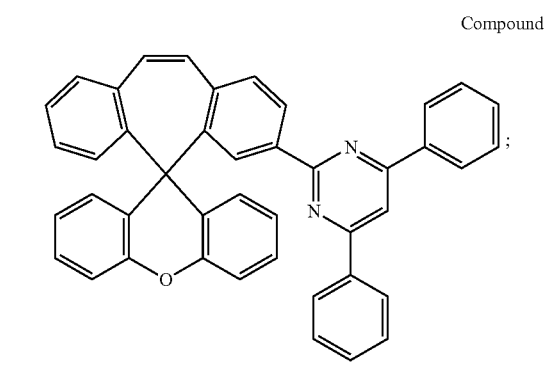

Compound 37
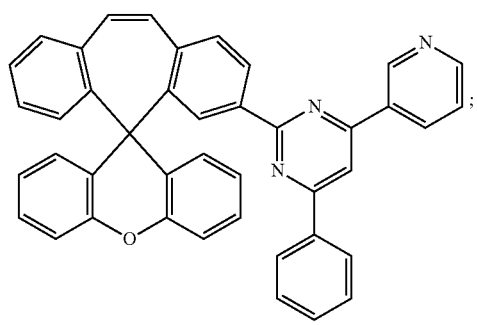
Compound 38
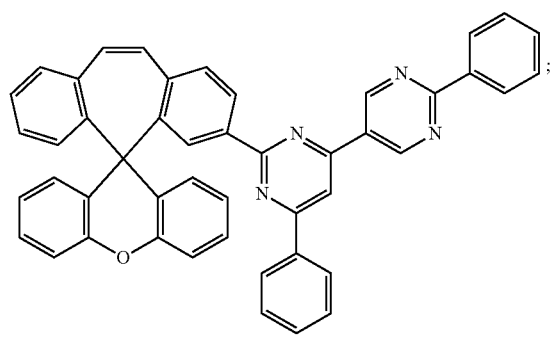
Compound 39
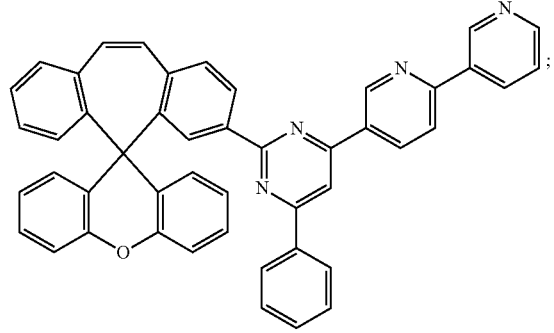
Compound 40
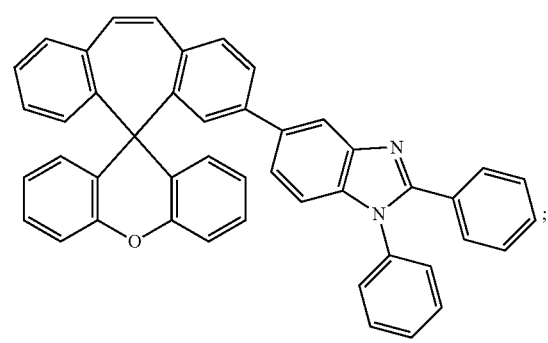
Compound 41
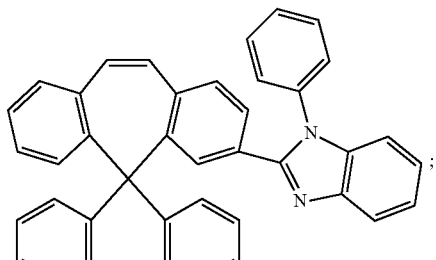
Compound 42
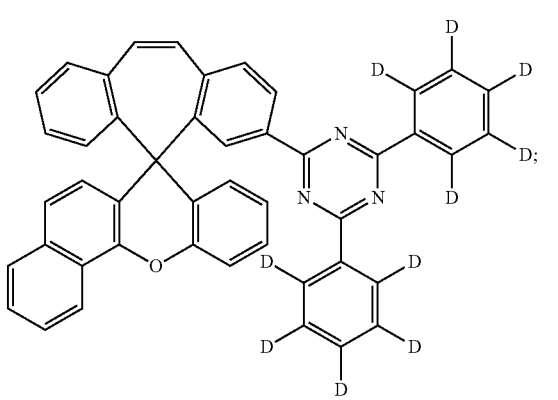
Compound 43
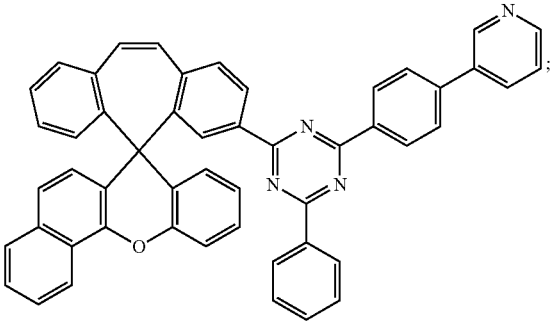
Compound 44
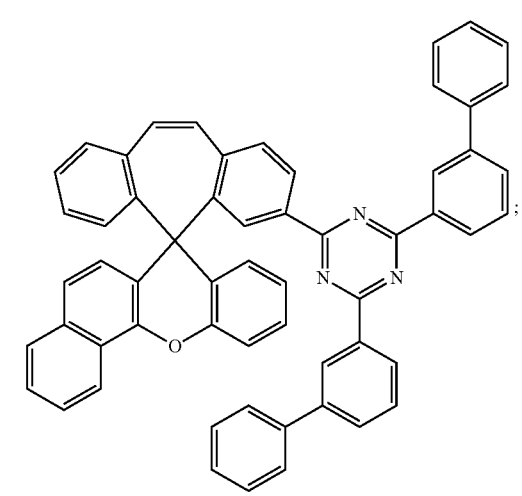

Compound 45
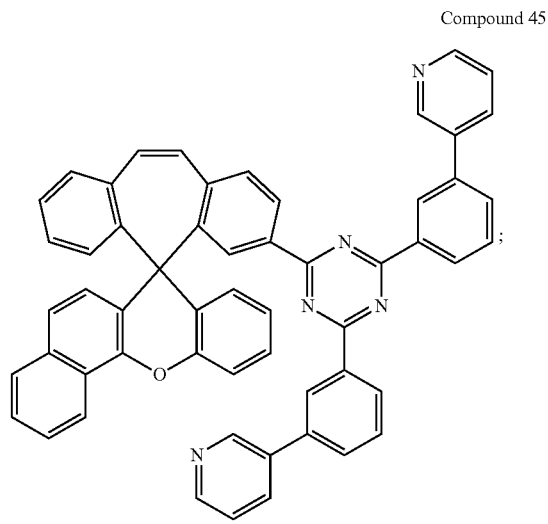
Compound 46
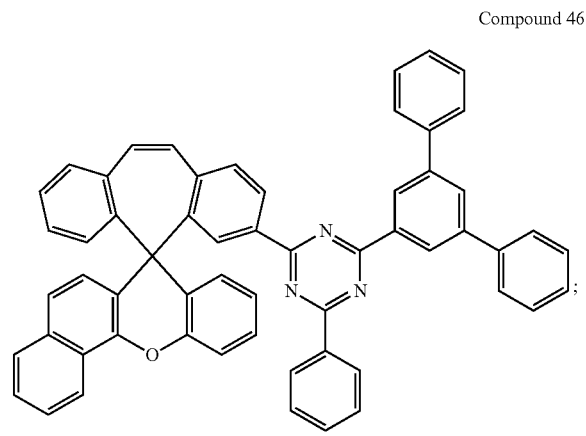
Compound 47
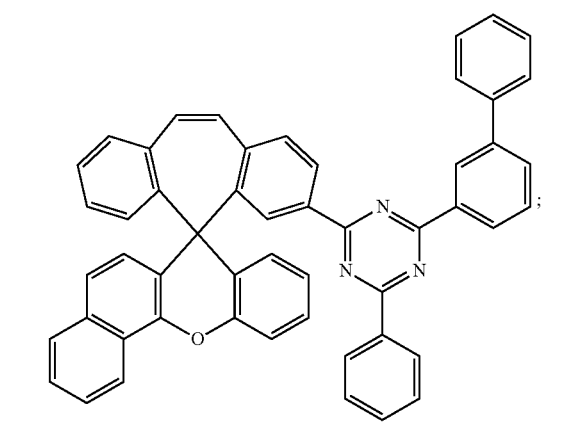
Compound 48
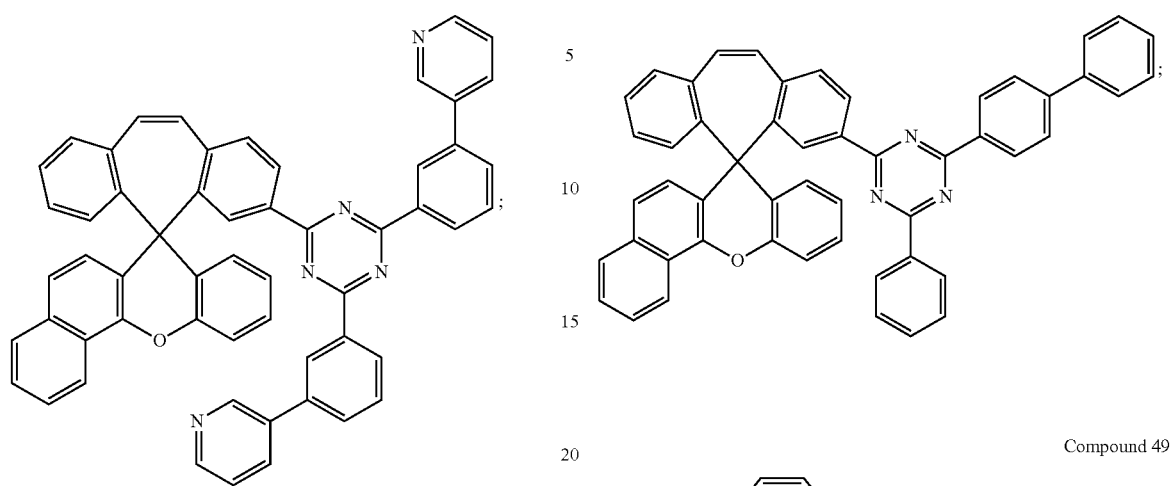
Compound 49
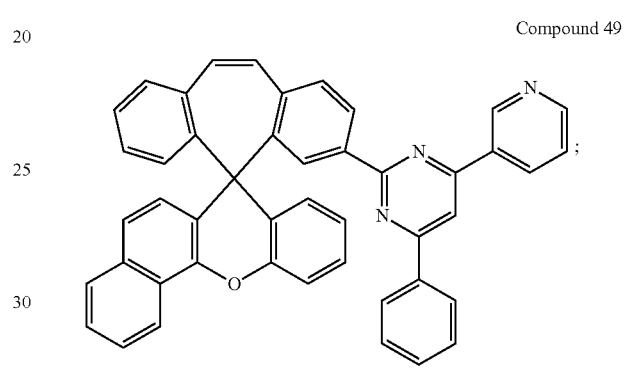
Compound 50
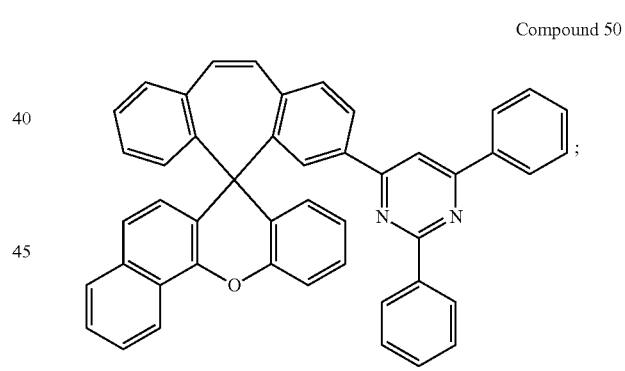
Compound 51
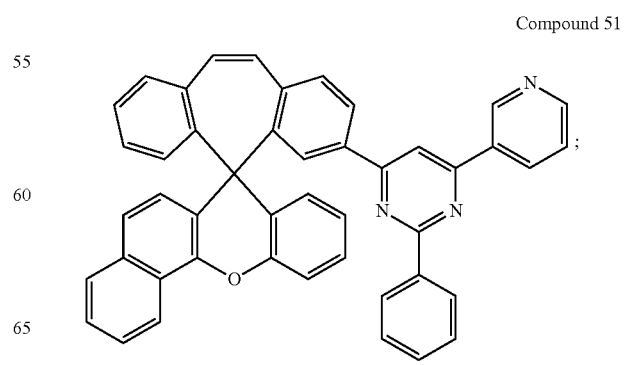

Compound 52
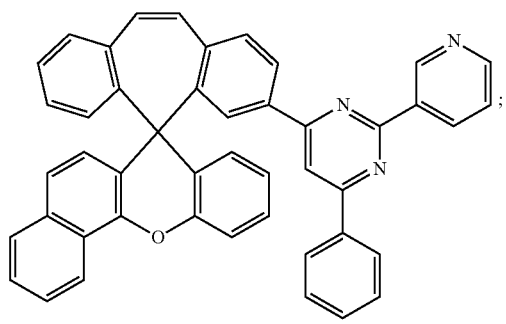
Compound 56
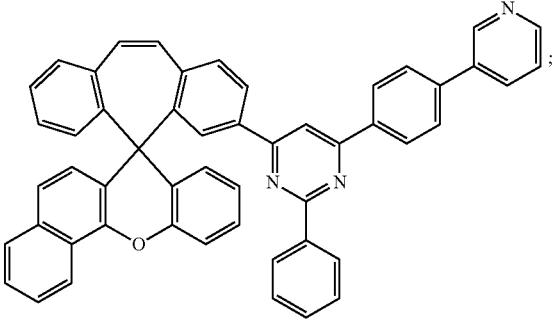
Compound 53
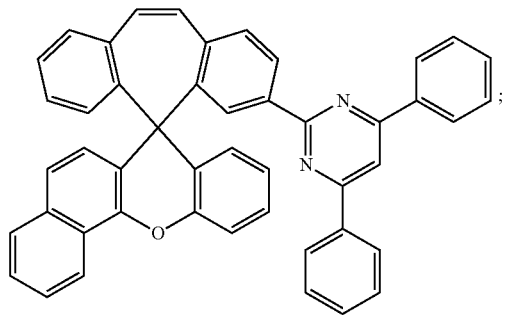
Compound 57
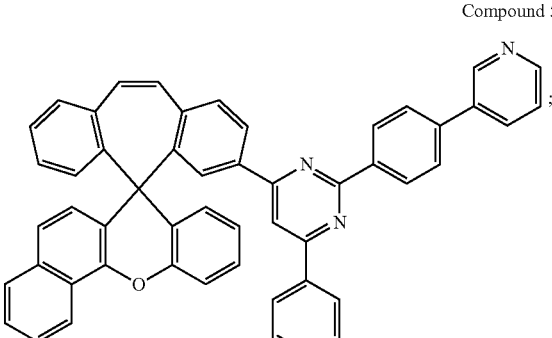
Compound 54
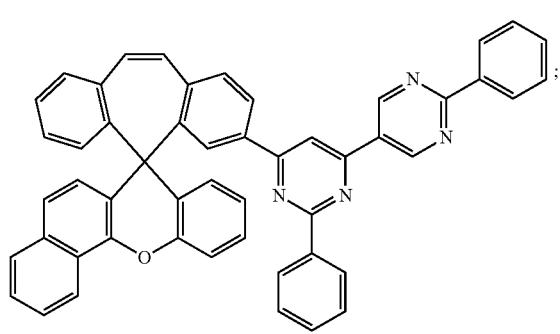
Compound 58
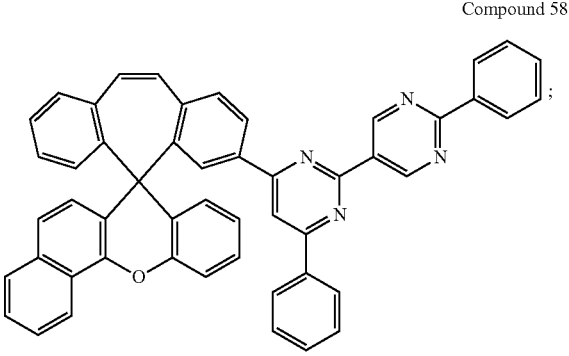
Compound 55
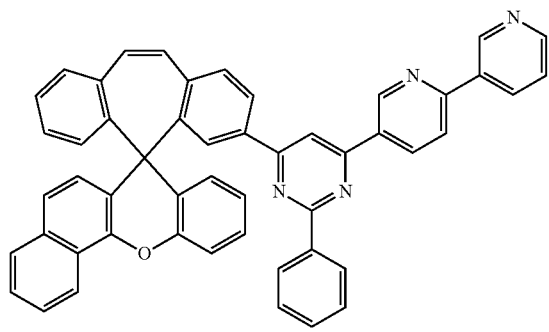
Compound 59
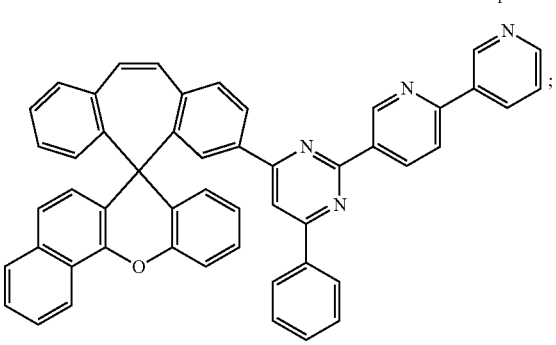

-continued
Compound 60
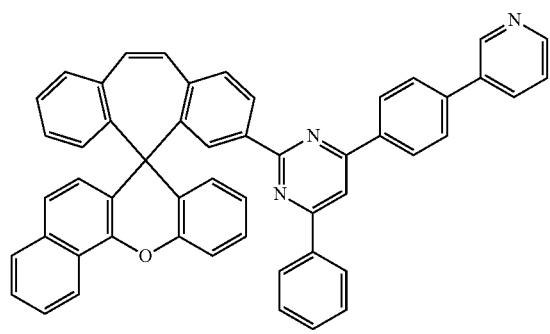
Compound 61
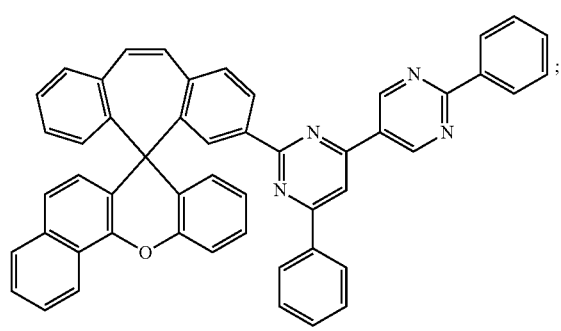
Compound 62
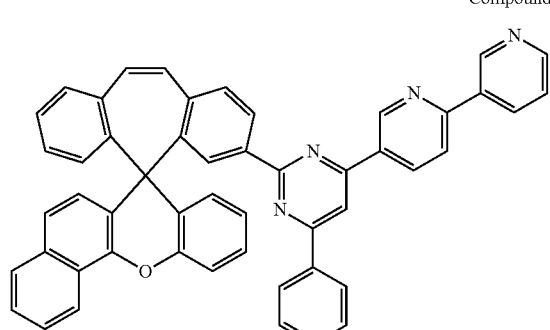
Compound 63
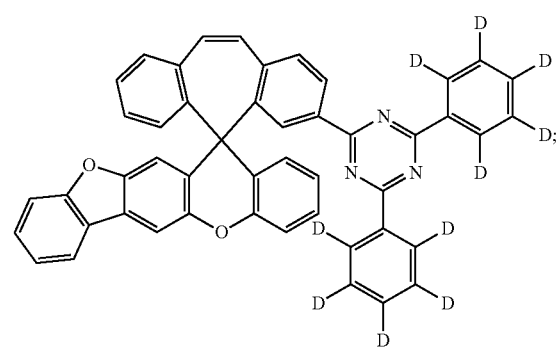
Compound 64
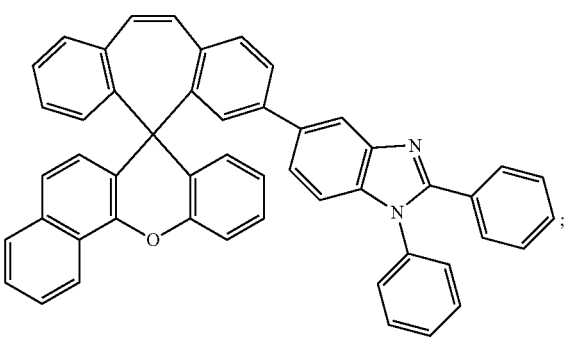
Compound 65
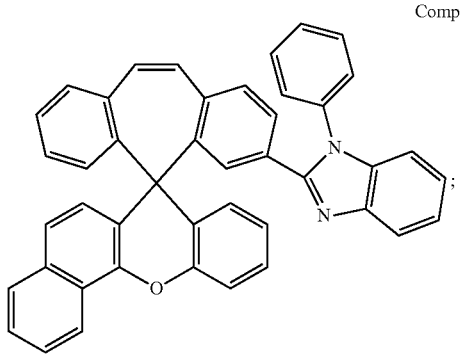
Compound 66
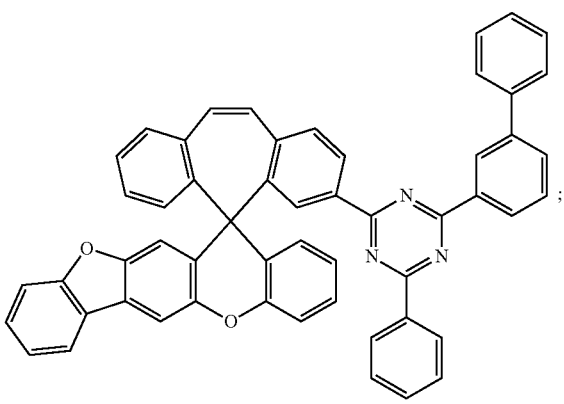
Compound 67
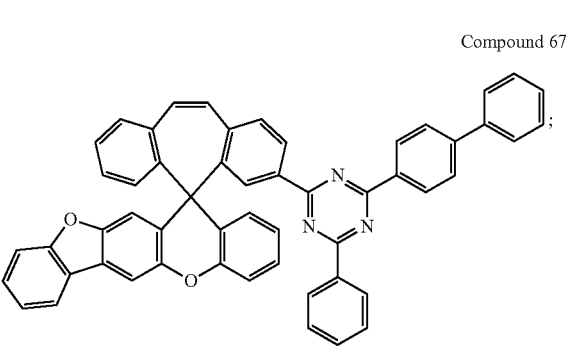

Compound 68
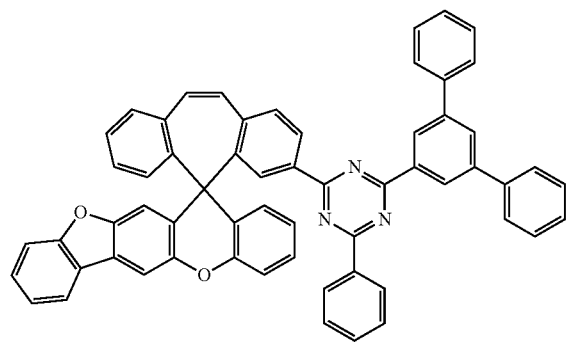
Compound 69
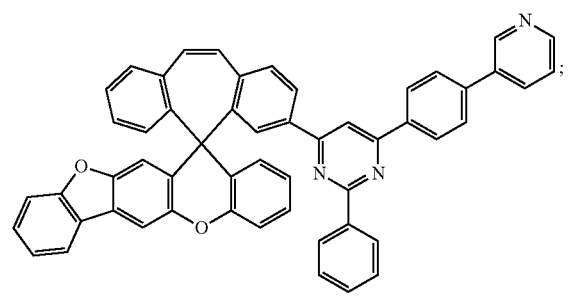
Compound 73
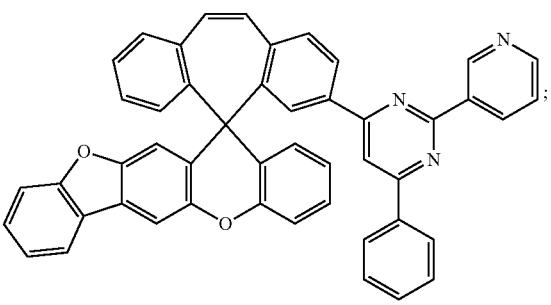
Compound 74
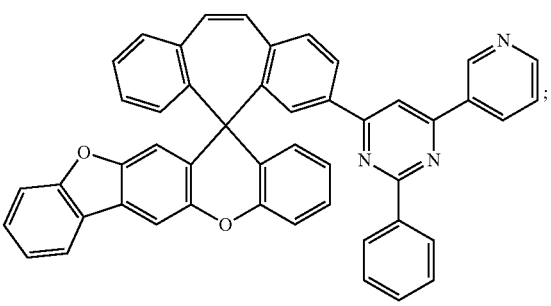
Compound 70
Compound 75
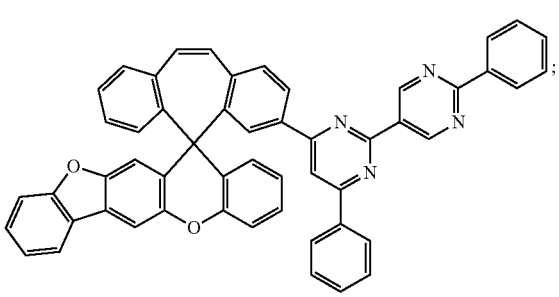
Compound 71
Compound 76
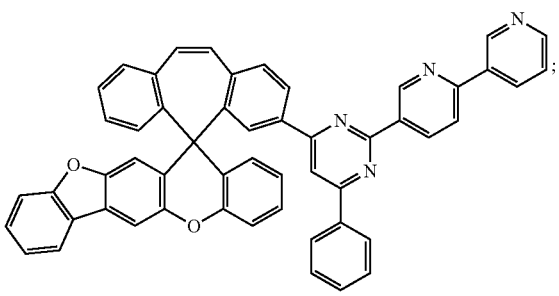
Compound 72
Compound 77
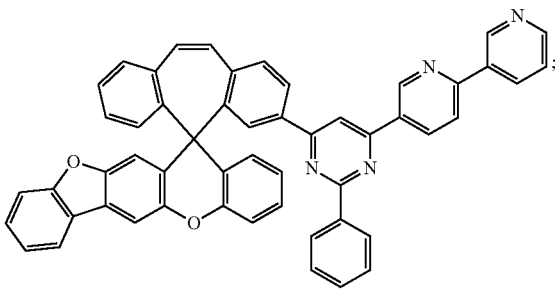

Compound 78
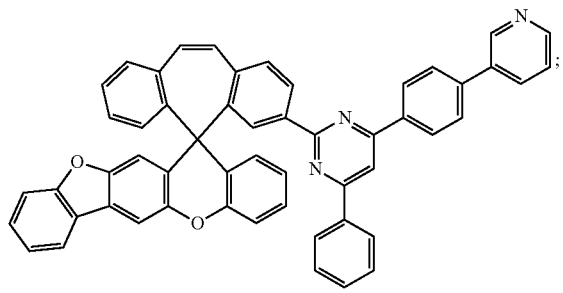
Compound 79
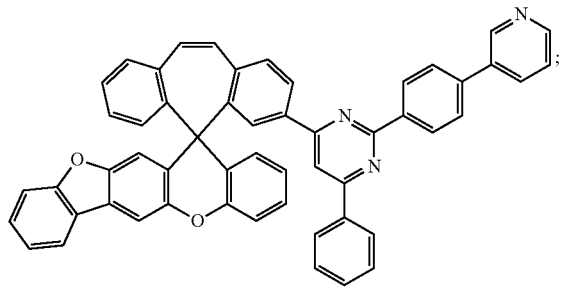
Compound 80
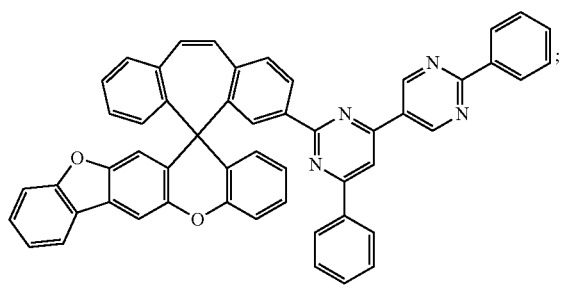
Compound 81
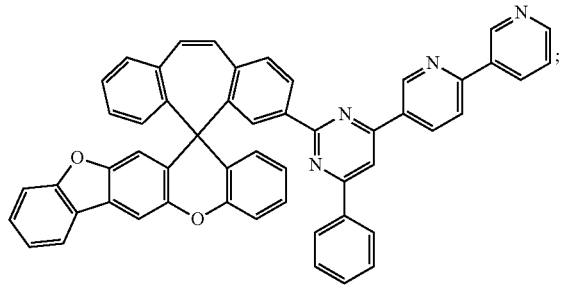
Compound 82
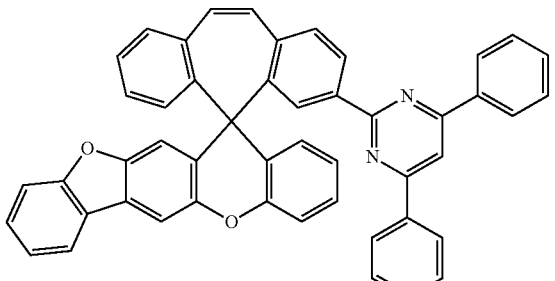
Compound 83
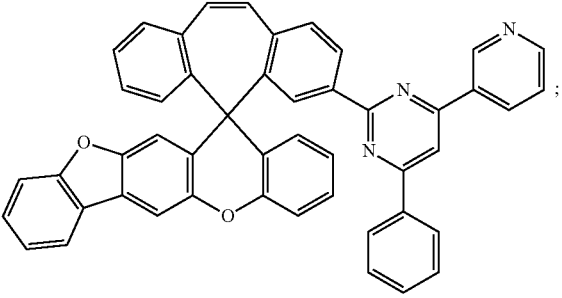
Compound 84
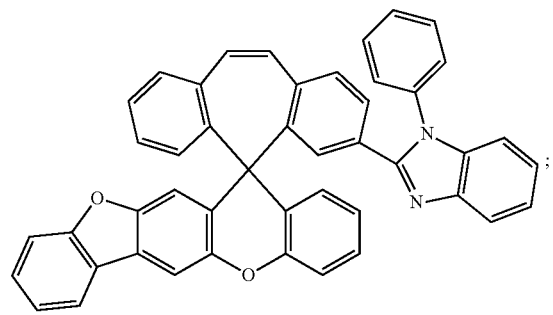
Compound 85
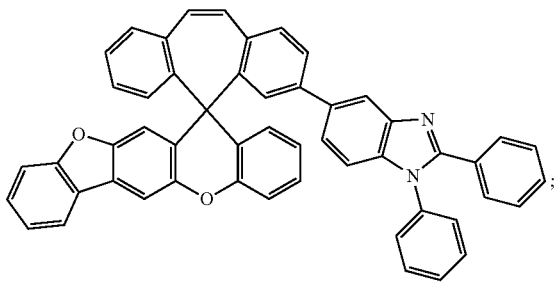
Compound 86
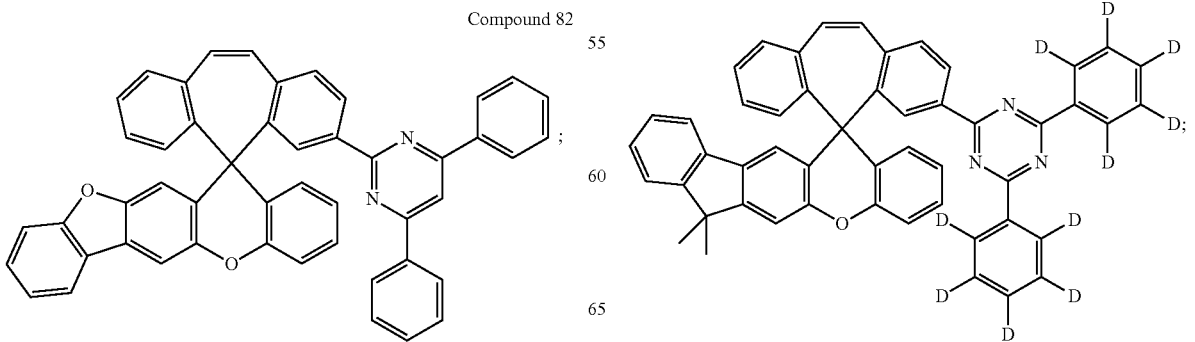

Compound 87
Compound 88
Compound 89
Compound 90
Compound 91 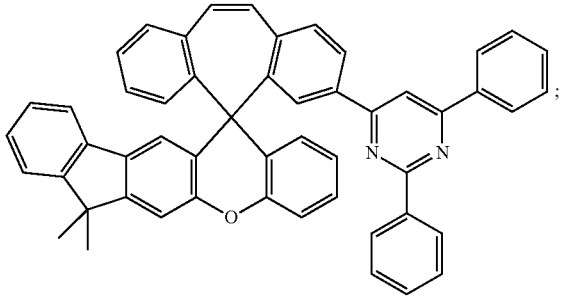
Compound 92 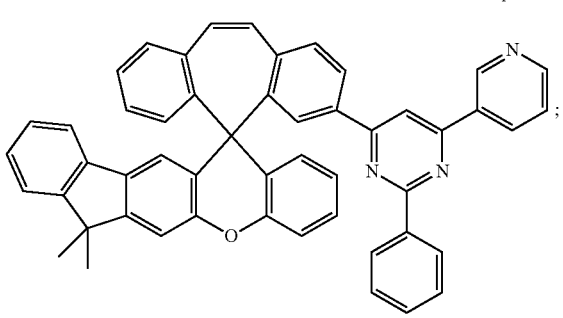
Compound 93 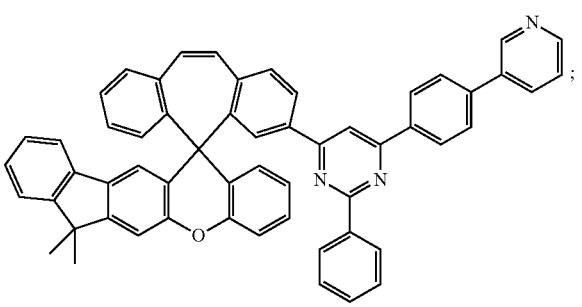
Compound 94 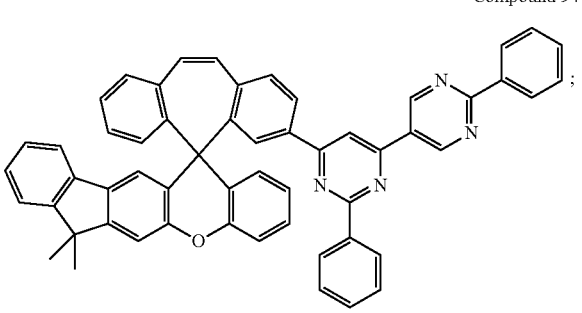
Compound 95 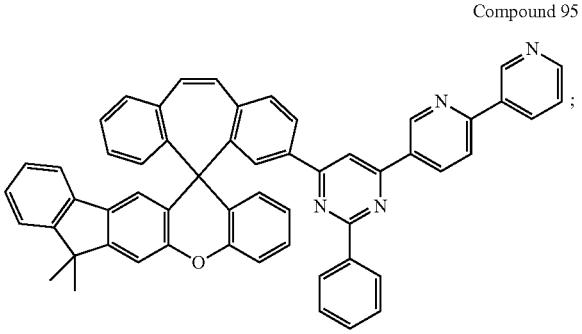

Compound 96
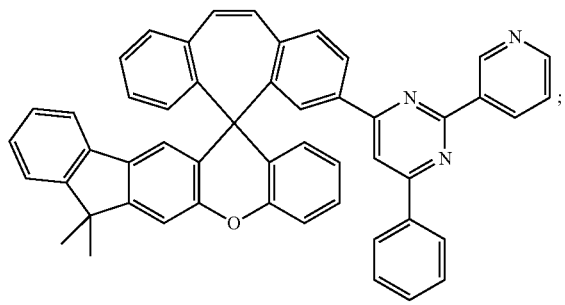
Compound 97
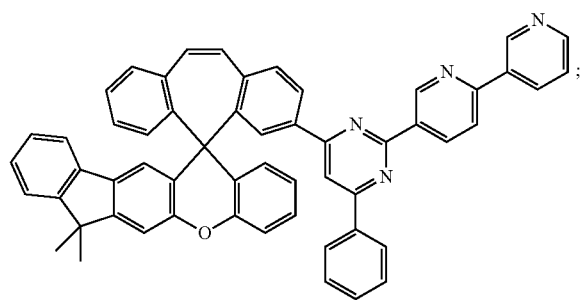
Compound 98
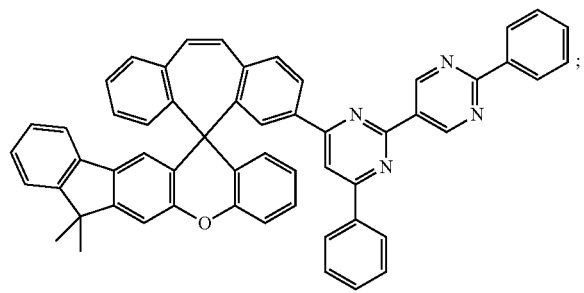
Compound 99
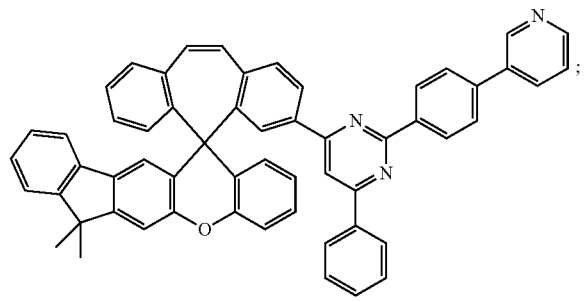
Compoudn 100
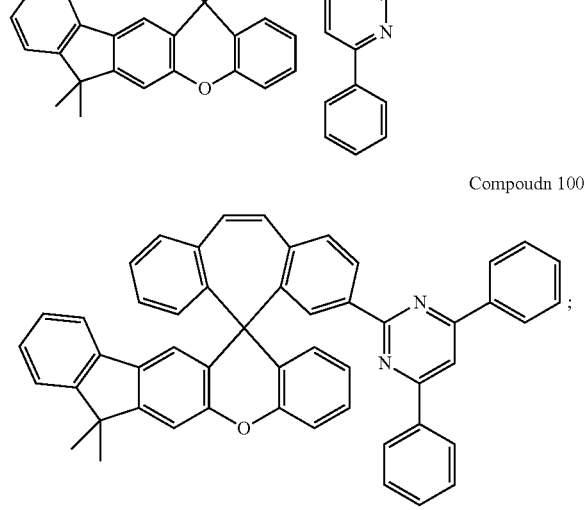
Compound 101
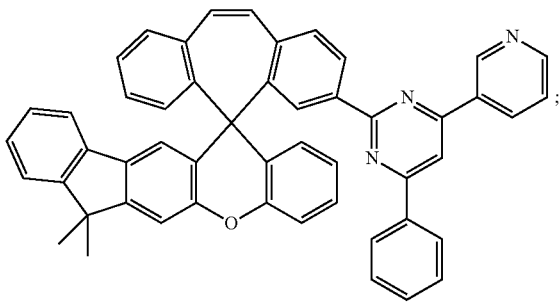
Compound 102
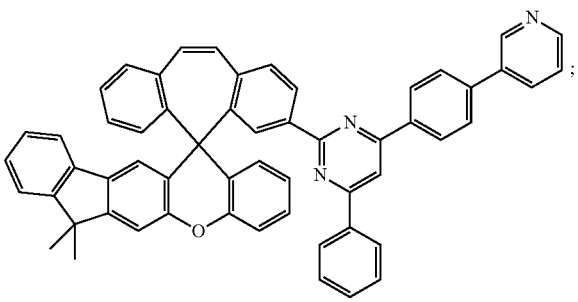
Compound 103
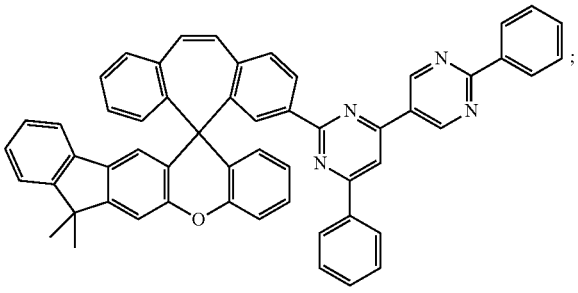
Compound 104
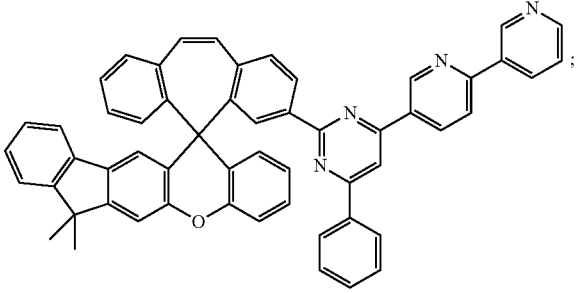
Compound 105
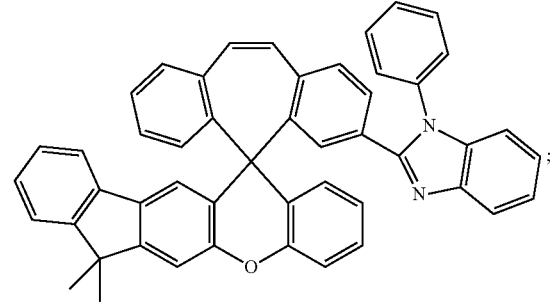

Compound 106
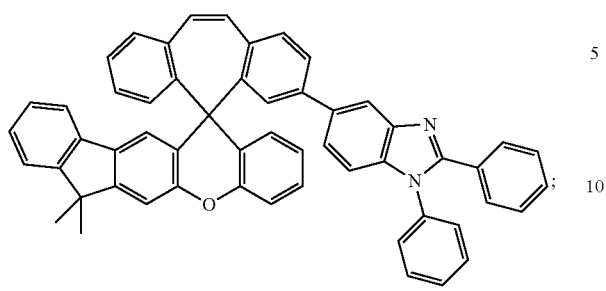
Compound 107
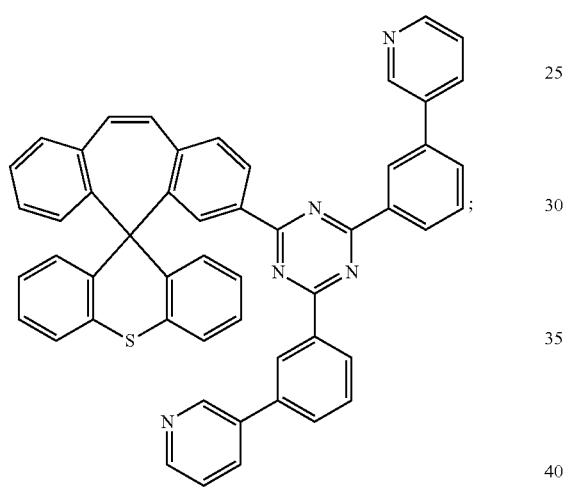
Compound 108
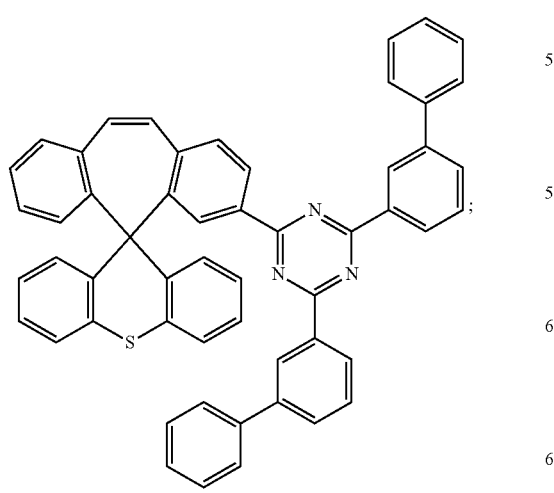
Compound 109
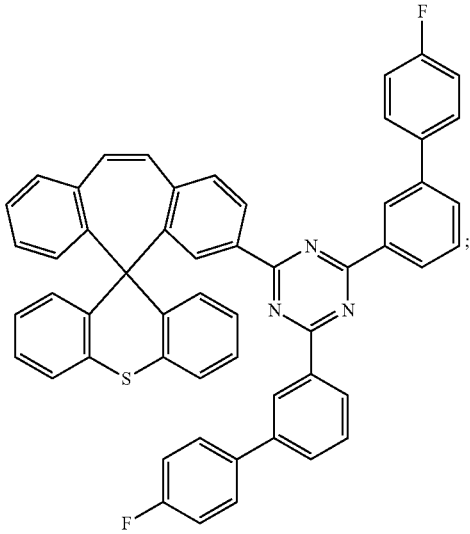
Compound 110
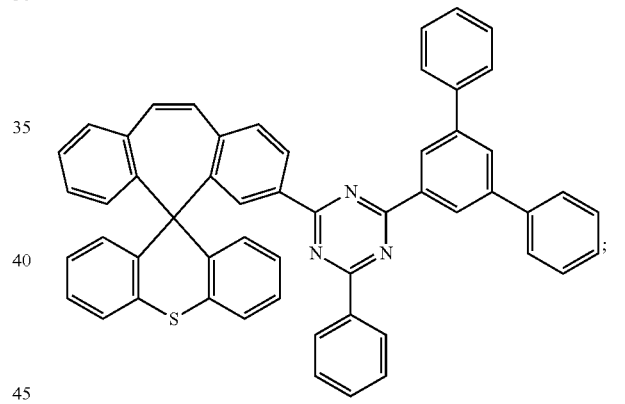
Compound 111
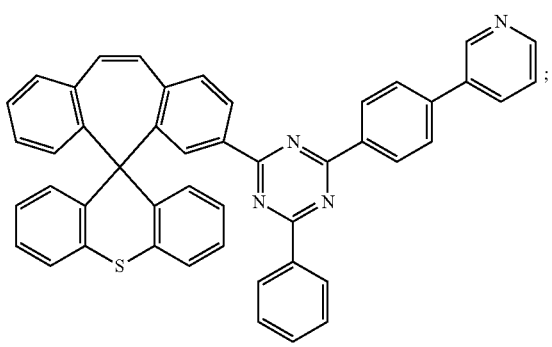

Compound 112
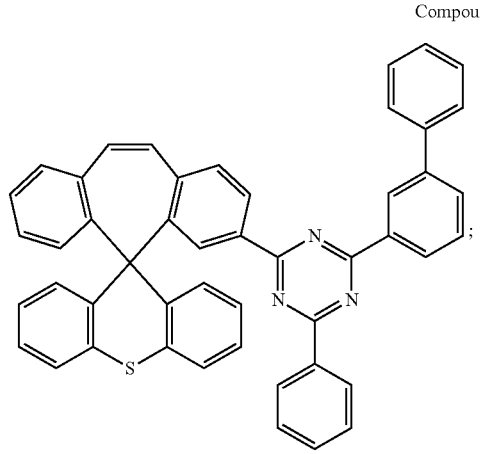
Compound 113
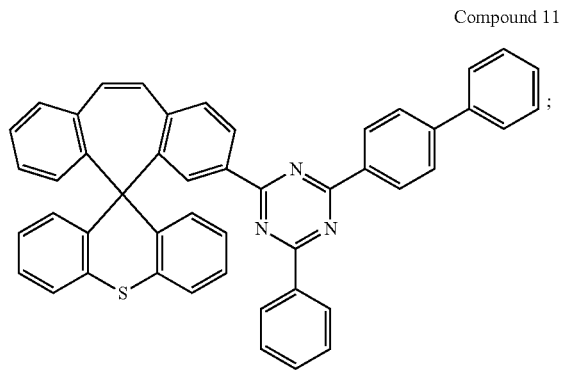
Compound 114
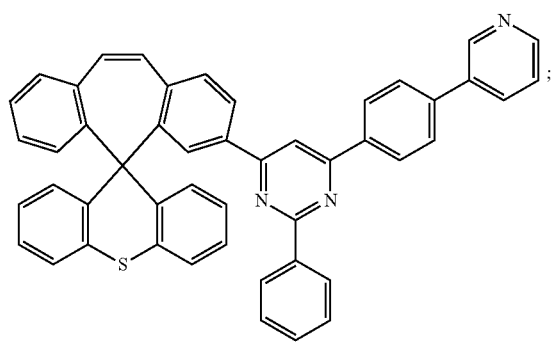
Compound 115
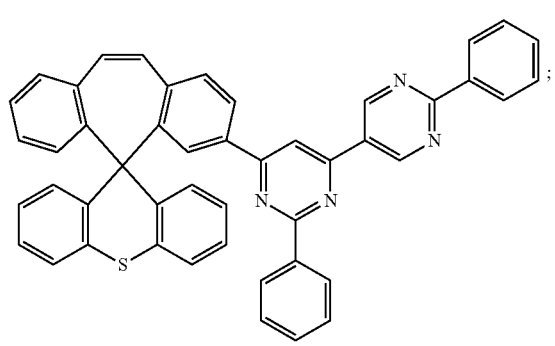
Compound 116
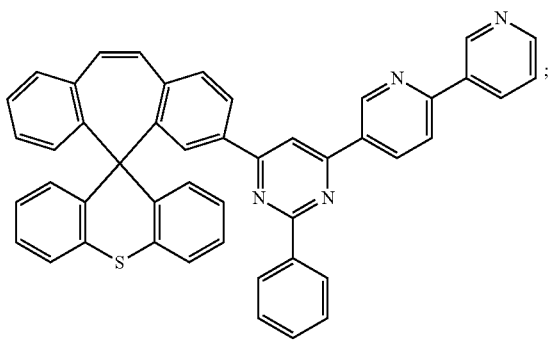
Compound 117
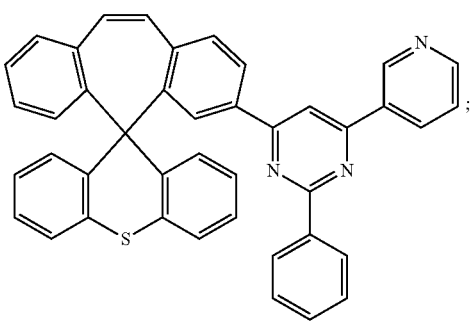
Compound 118
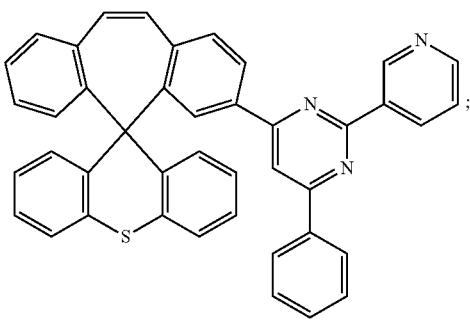
Compound 119
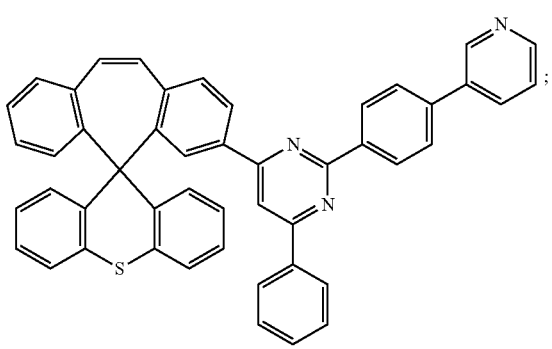

Compound 120
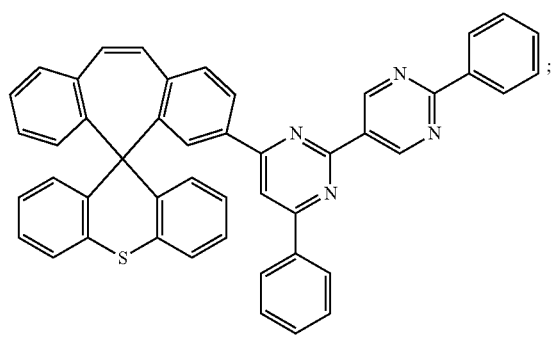
Compound 121
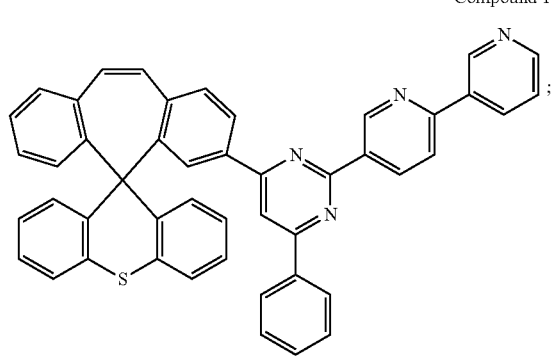
Compound 122
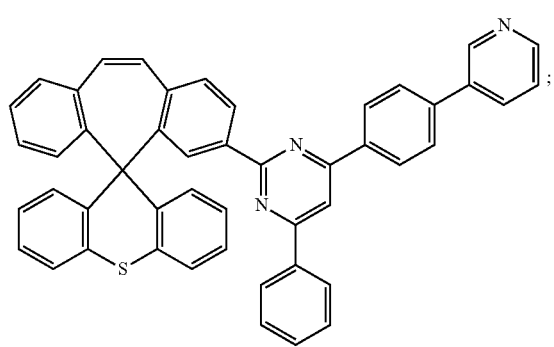
Compound 123
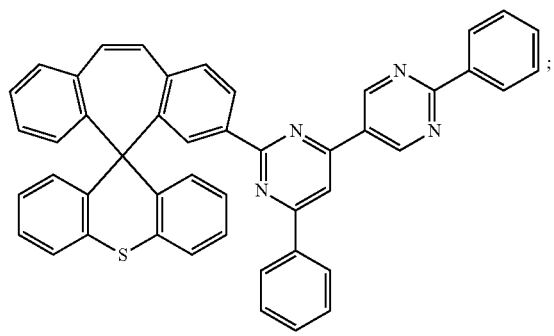
Compound 124
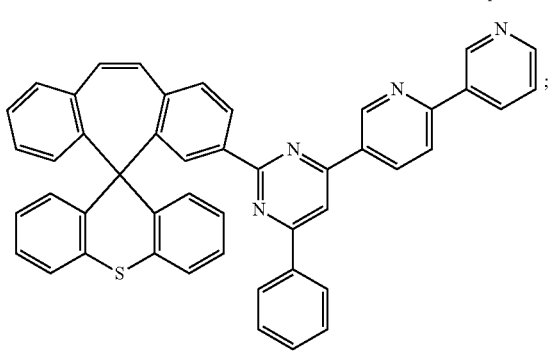
Compound 125
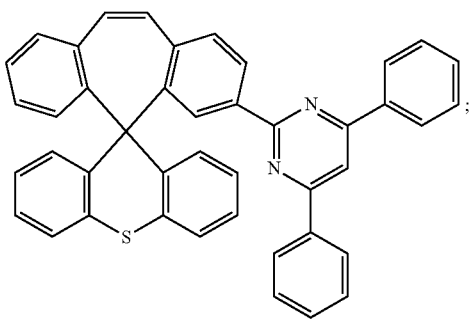
Compound 126
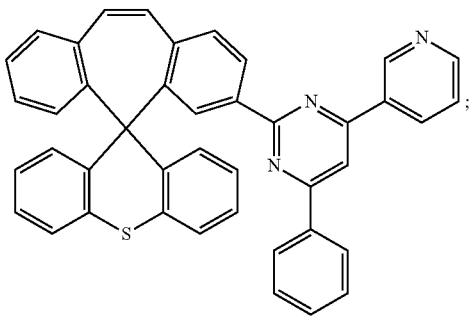
Compound 127
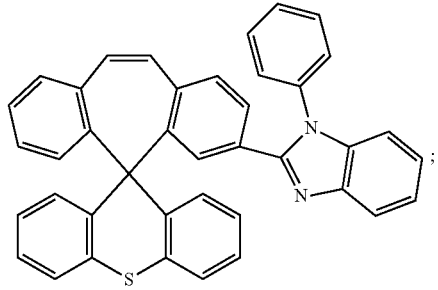

Compound 128
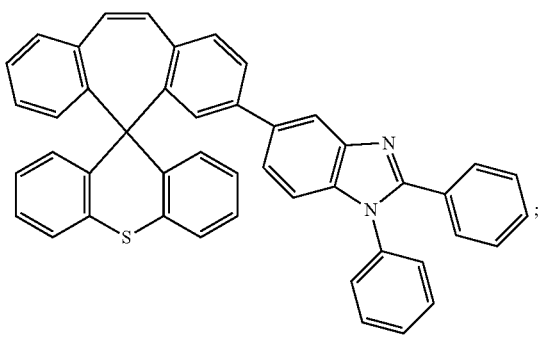
Compound 129
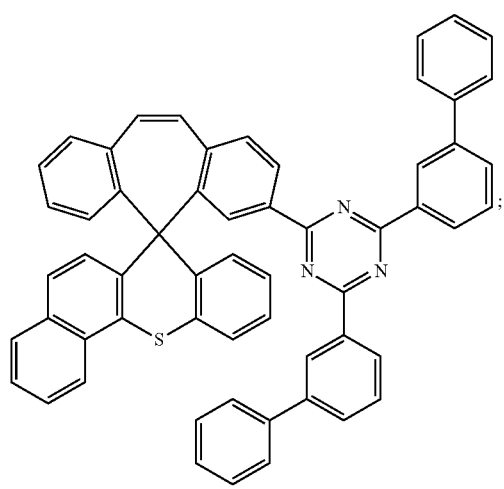
Compound 130
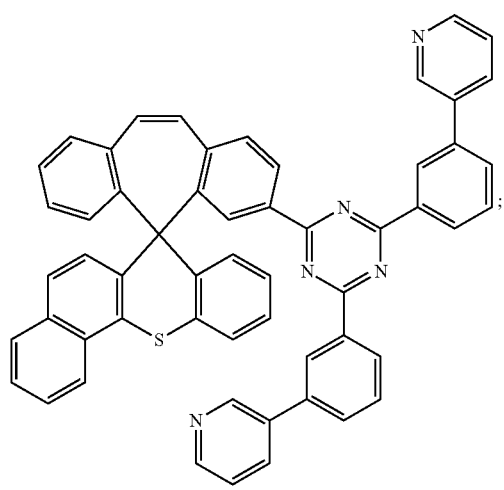
Compound 131
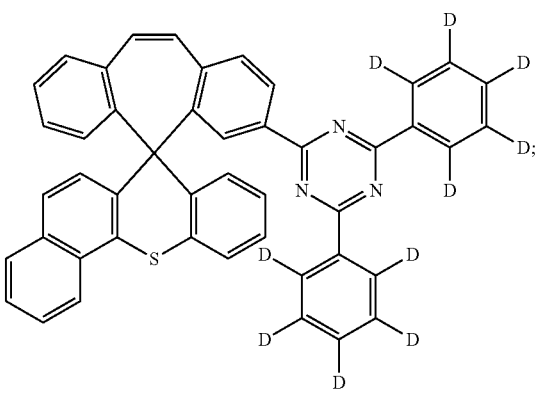
Compound 132
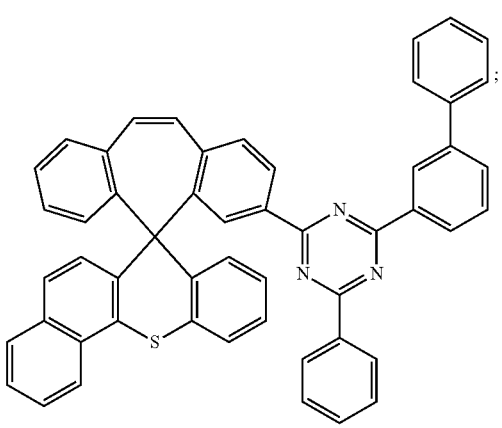
Compound 133
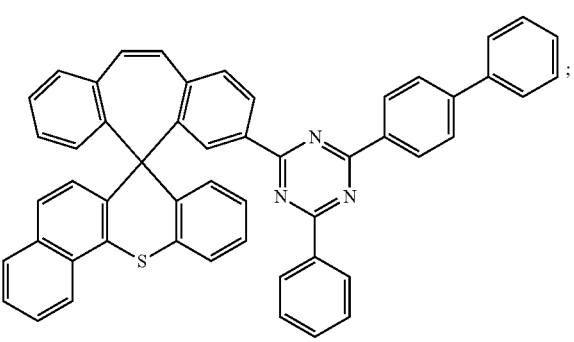
Compound 134
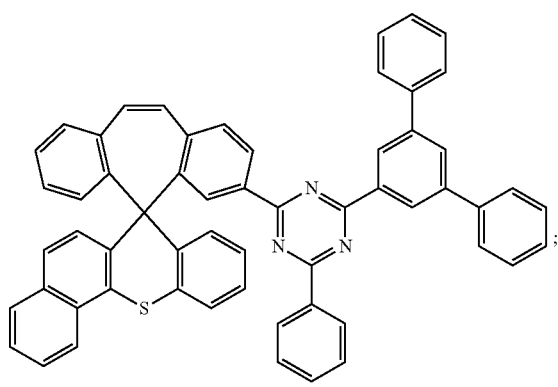

Compound 135
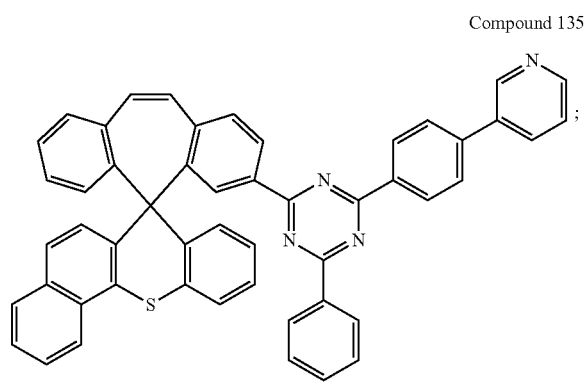
Compound 136
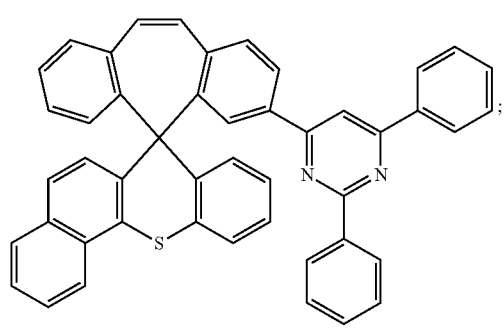
Compound 137
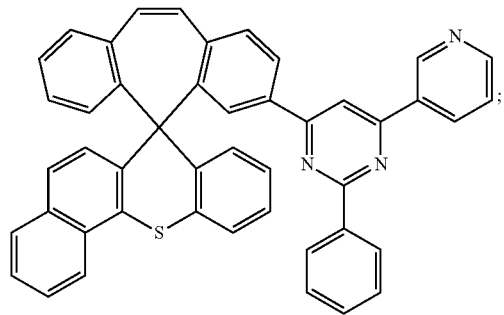
Compound 138
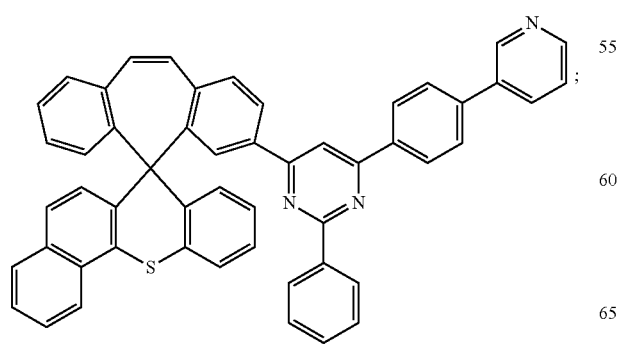
Compound 139
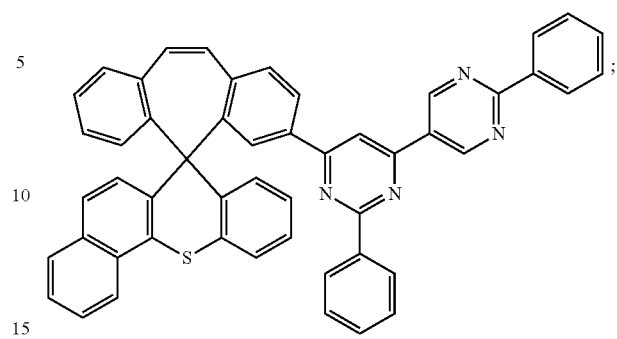
Compound 140
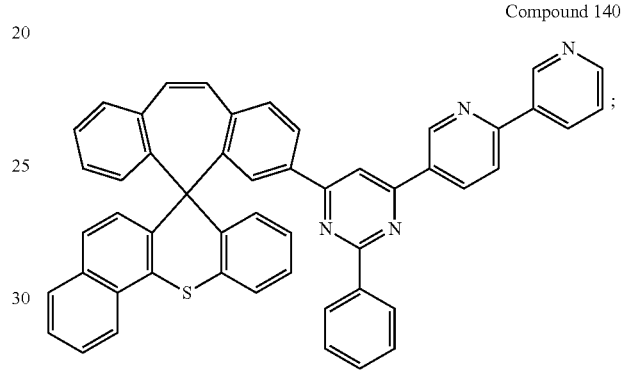
Compound 141
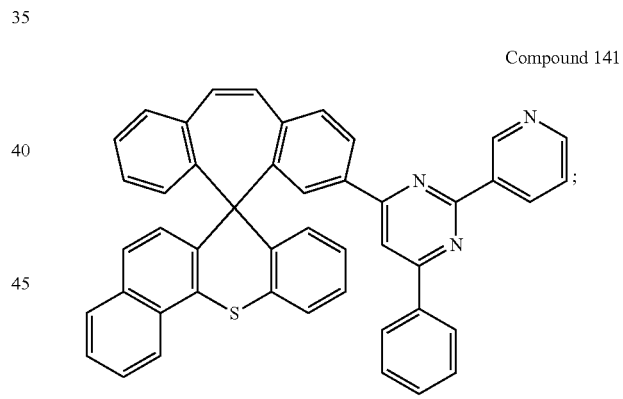
Compound 142
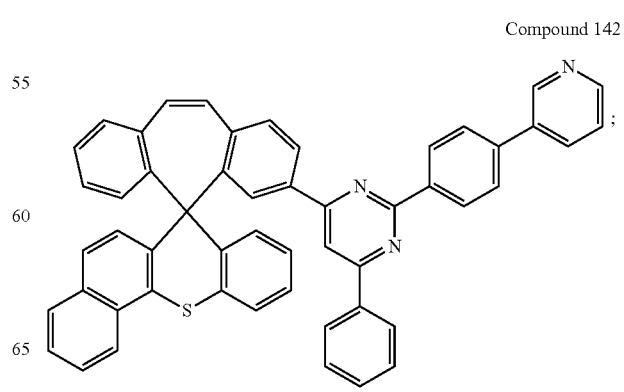

Compound 143
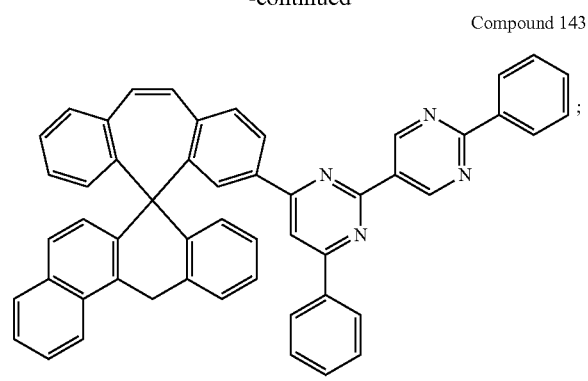
Compound 147
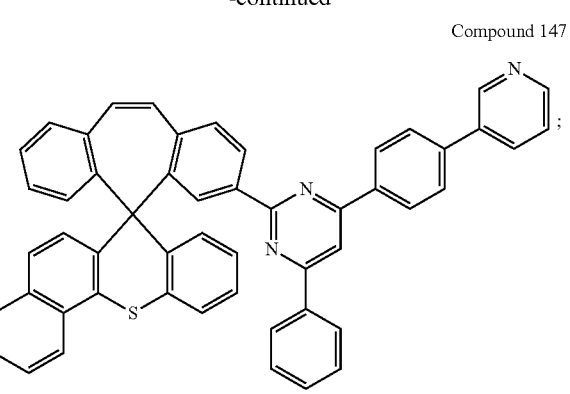
Compound 144
Compound 148
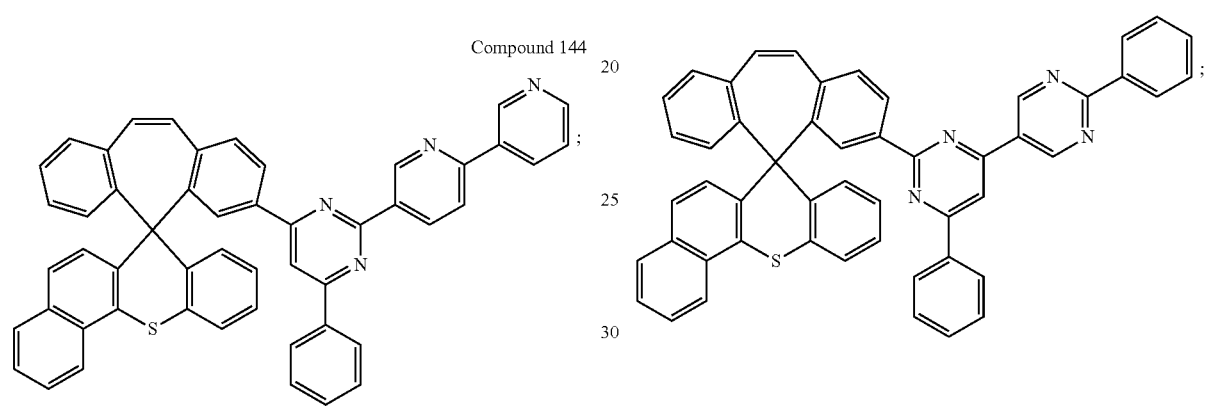
Compound 145
Compound 149
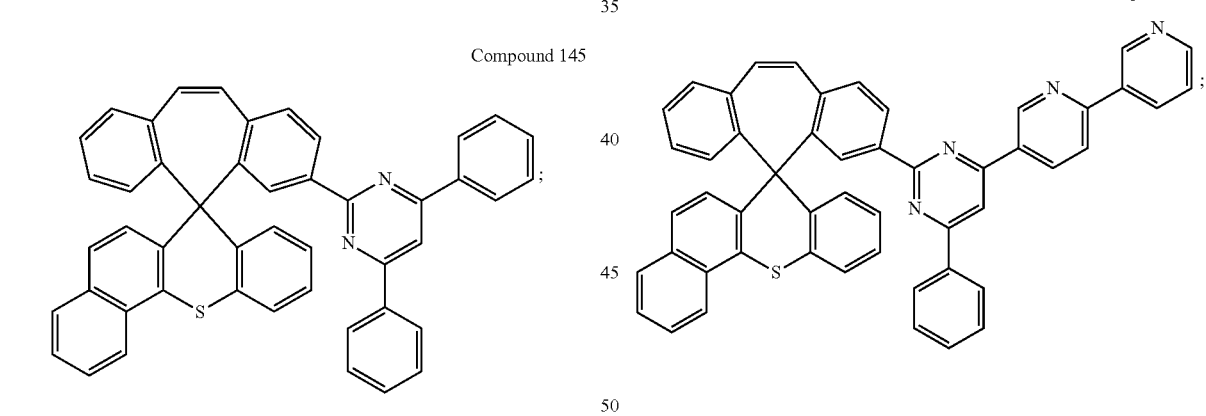
Compound 146
Compound 150
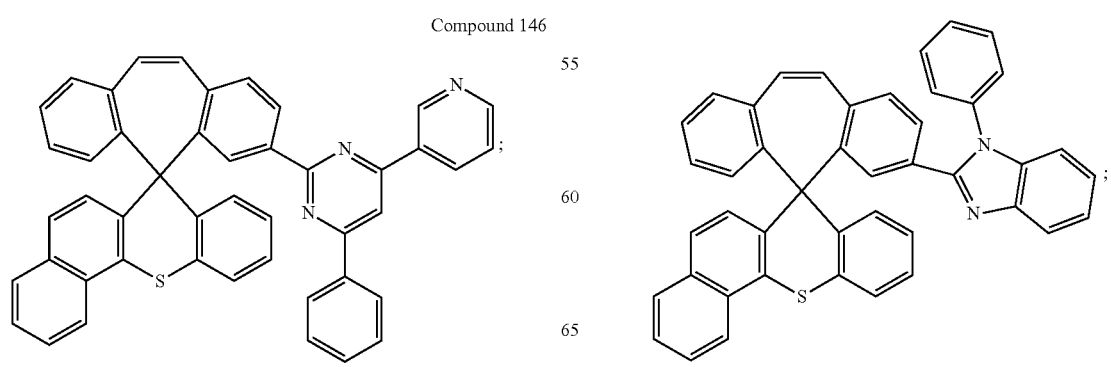

Compound 151
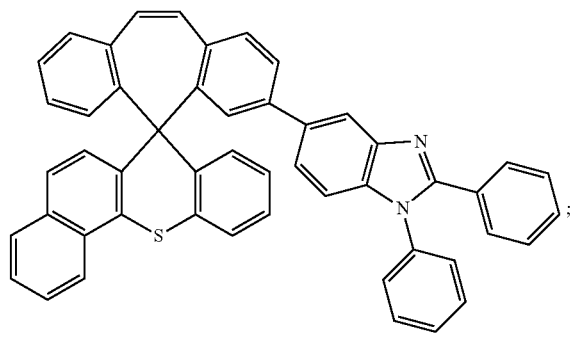
Compound 155
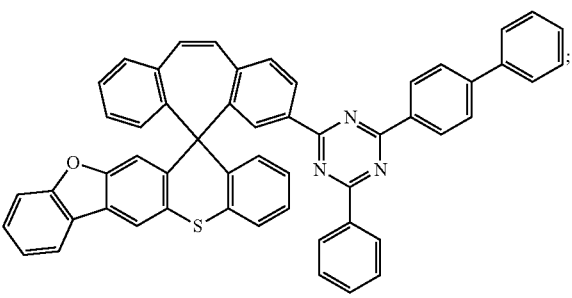
Compound 152
Compound 156
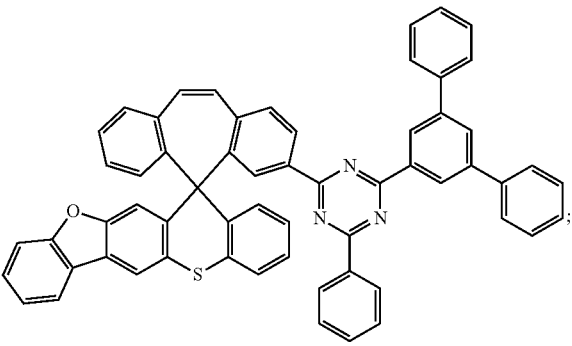
Compound 153
Compound 157
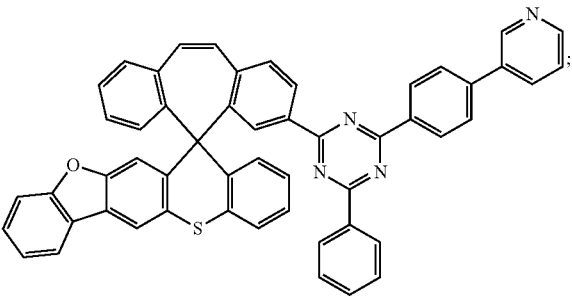
Compound 154
Compound 158
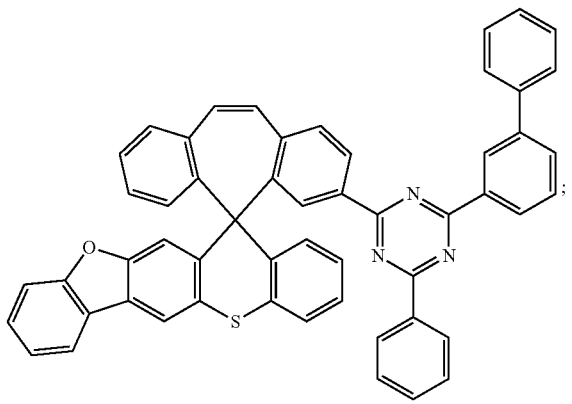

Compound 159
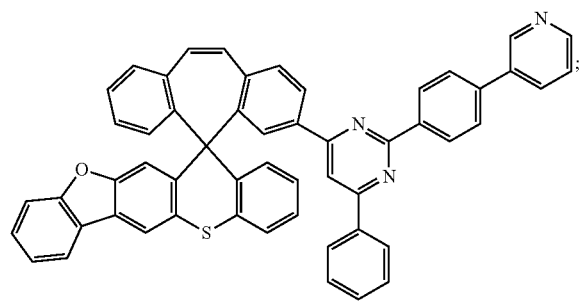
Compound 164
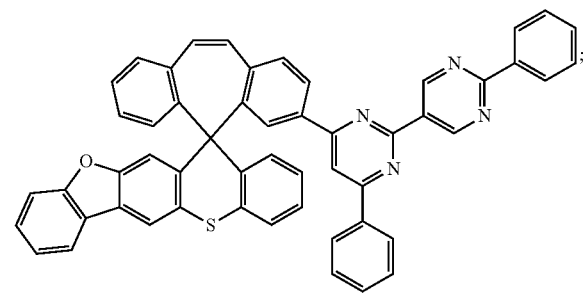
Compound 160
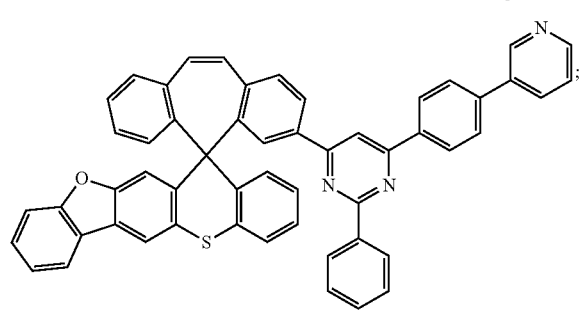
Compound 165
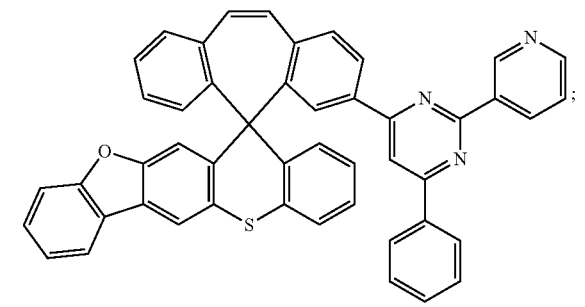
Compound 161
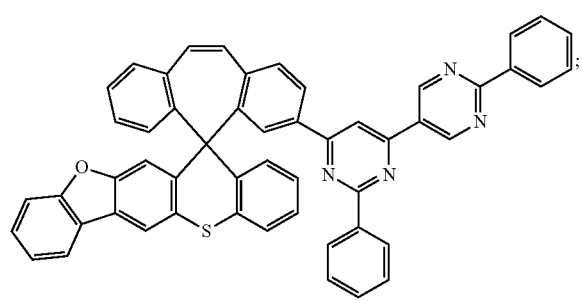
Compound 166
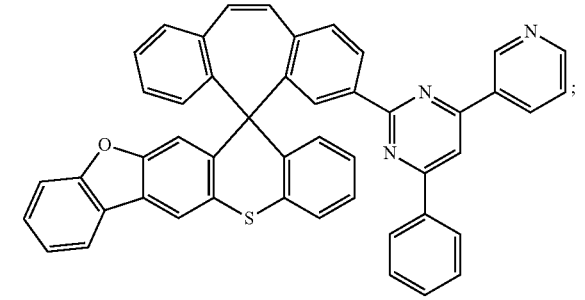
Compound 162
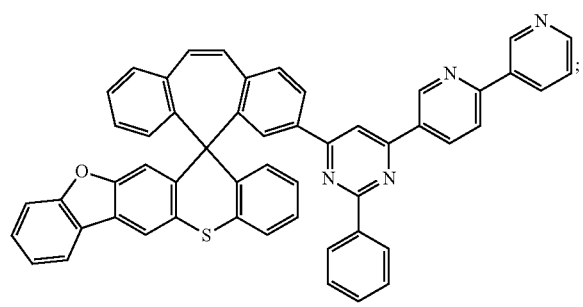
Compound 167
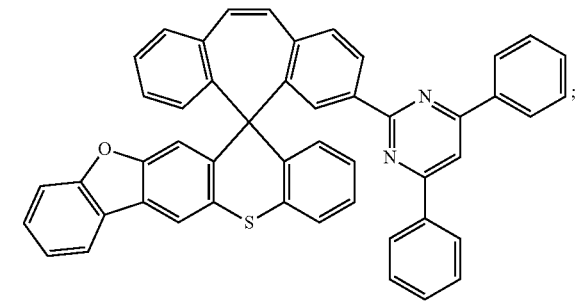
Compound 163
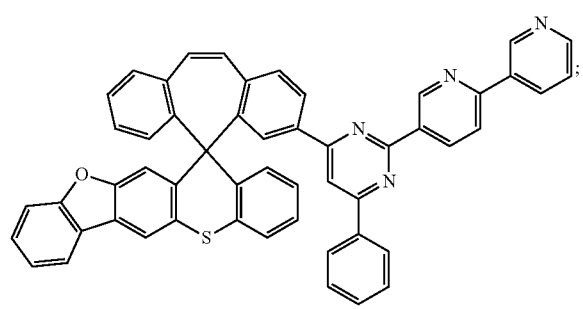
Compound 168
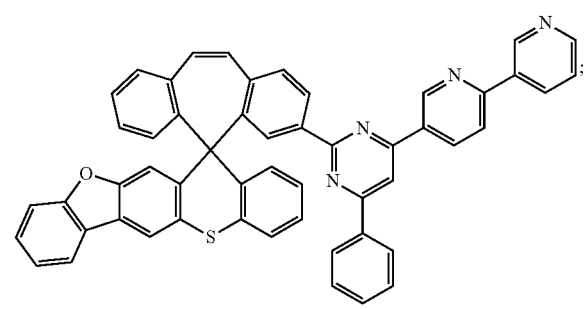

Compound 169
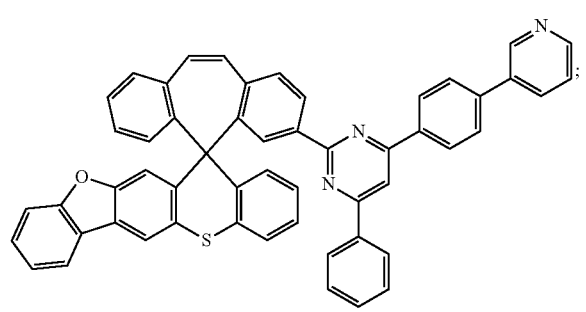
Compound 170
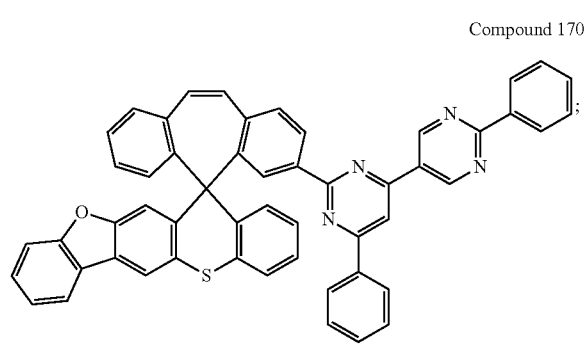
Compound 171
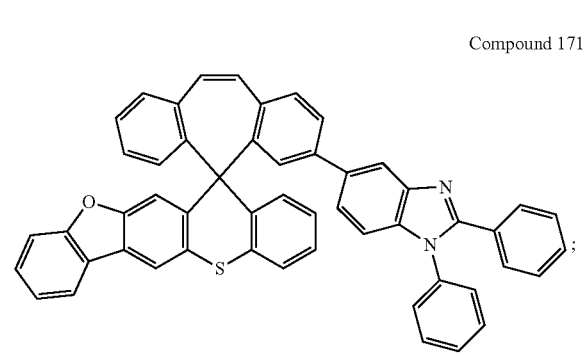
Compound 172
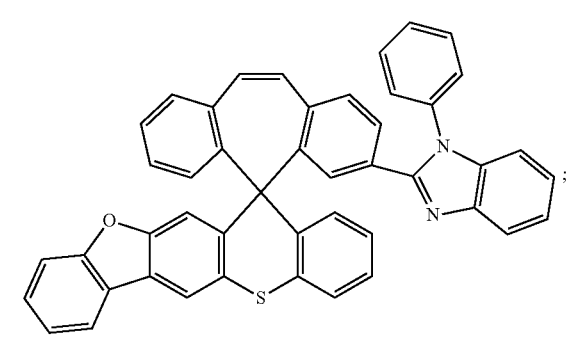
Compound 173
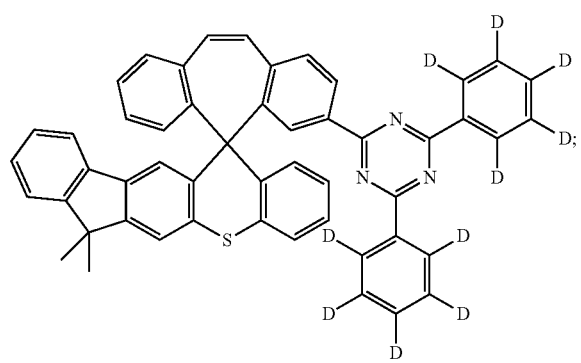
Compound 174
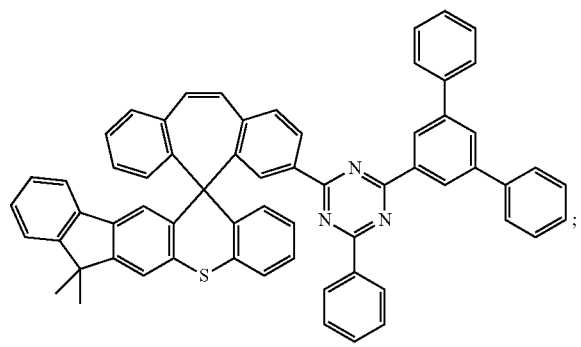
Compound 175
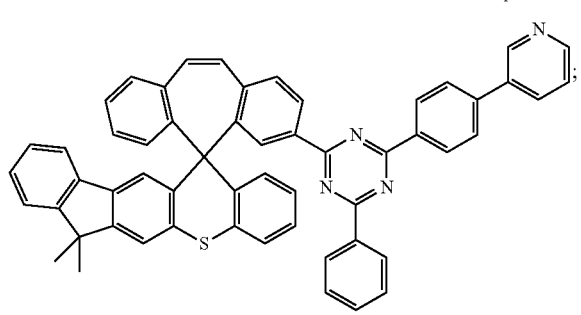
Compound 176
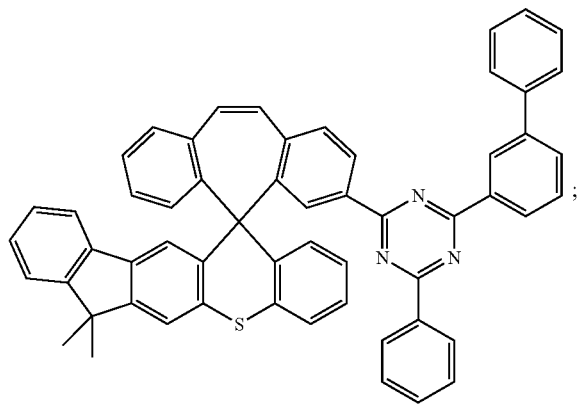

Compound 177
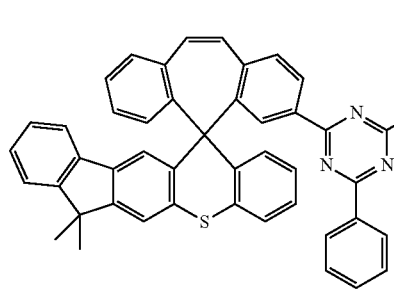
Compound 178
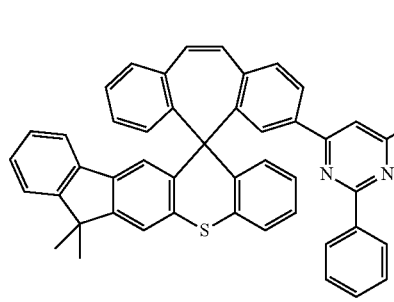
Compound 179
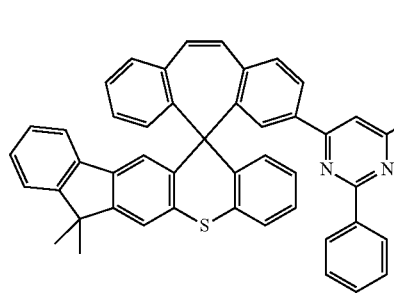
Compound 180
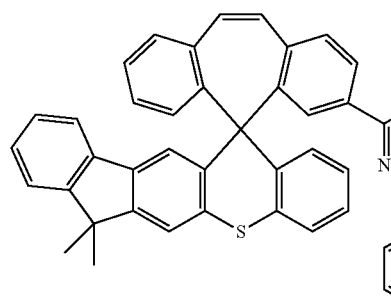
Compound 181
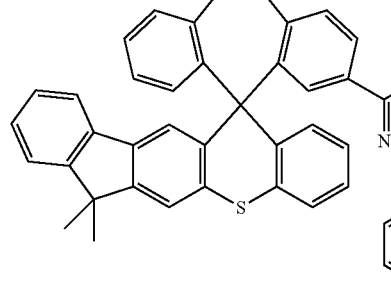
Compound 182
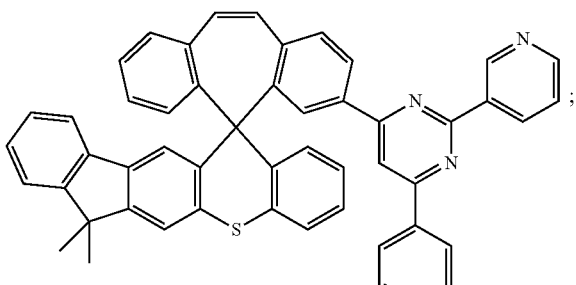
Compound 183
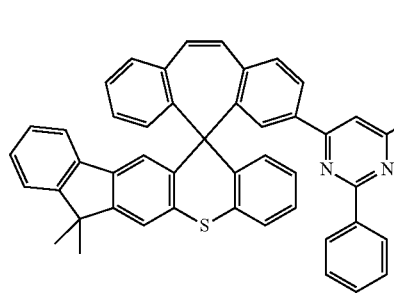
Compound 184
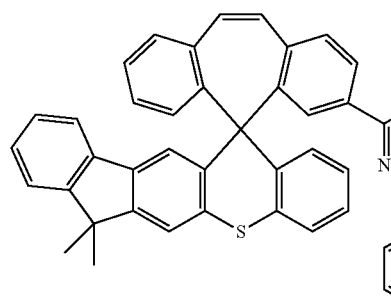
Compound 185
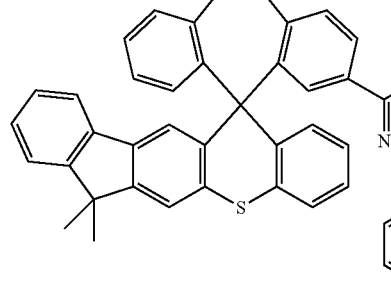

Compound 186
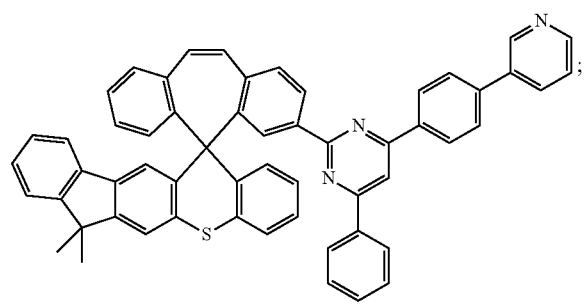
Compound 187
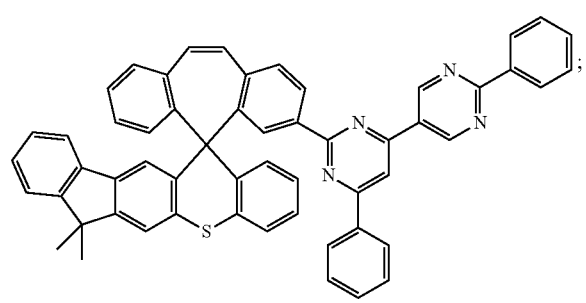
Compound 188
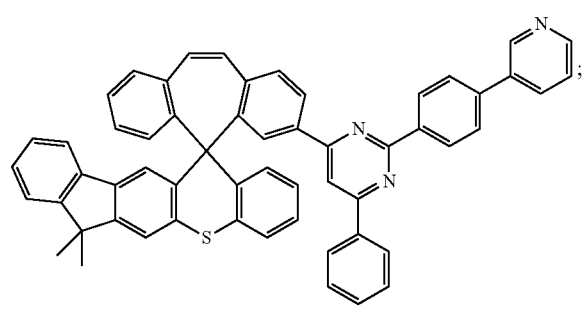
Compound 189
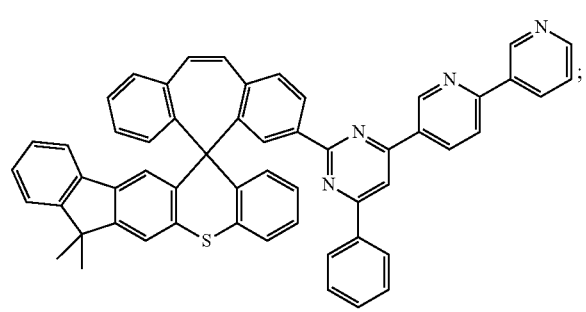
Compound 190
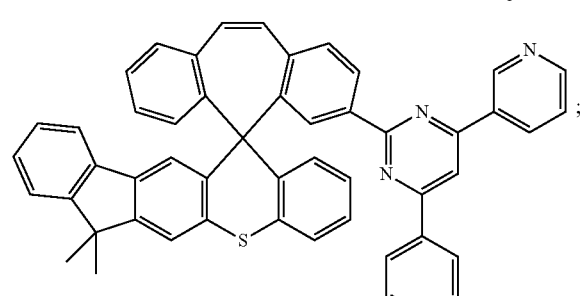
Compound 191
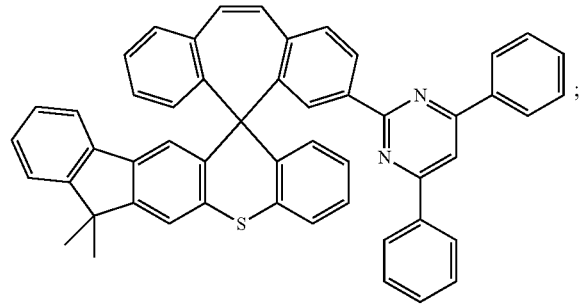
Compound 192
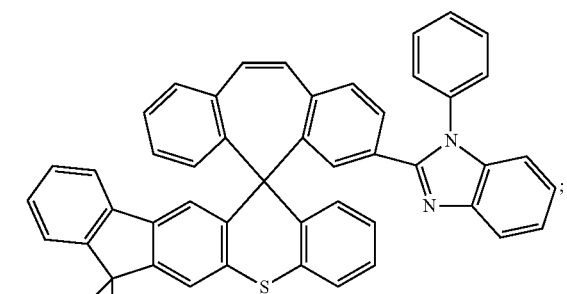
Compound 193
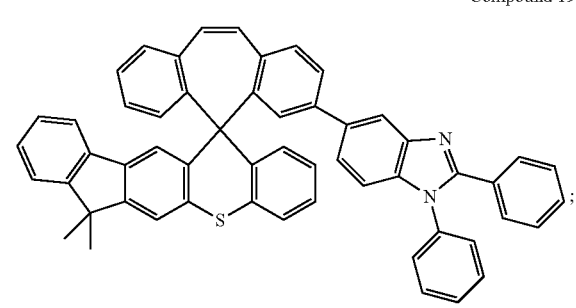
Compound 194
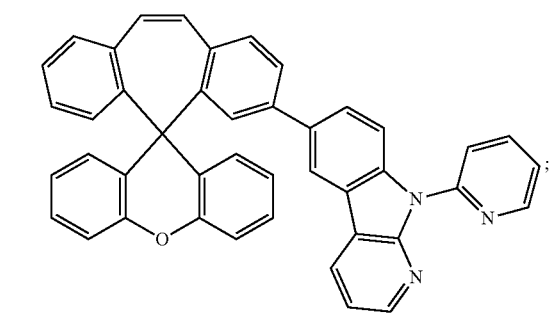
Compound 195
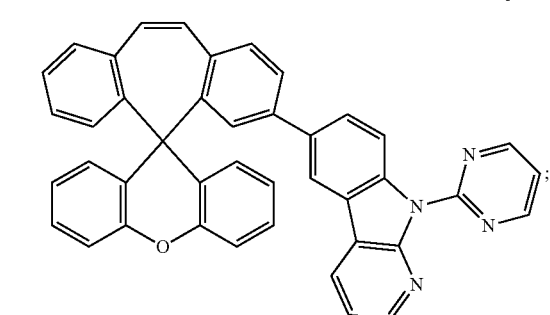

Compound 196
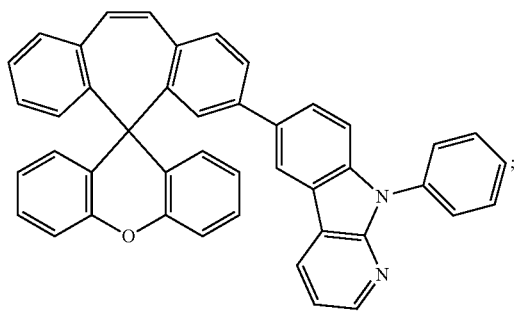
Compound 197
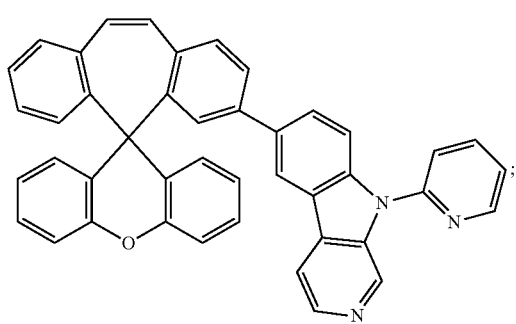
Compound 198
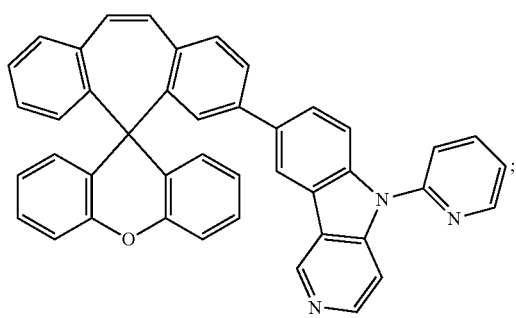
Compound 199
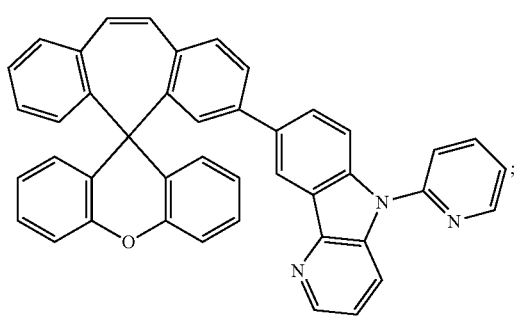
Compound 200
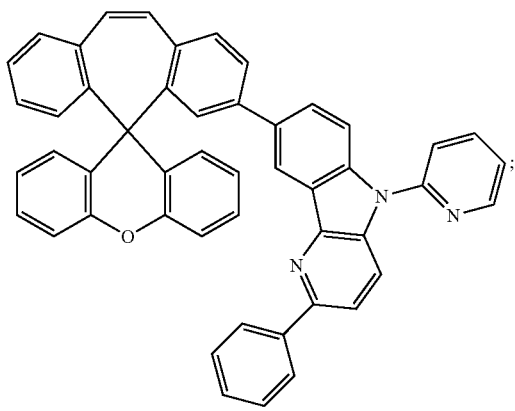
Compound 201
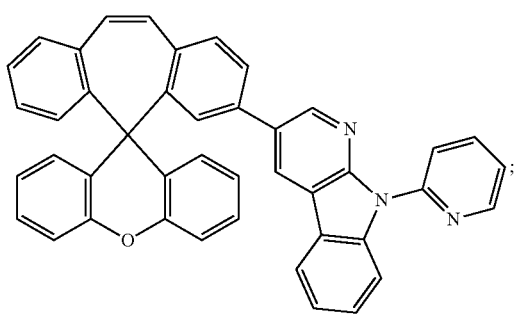
Compound 202
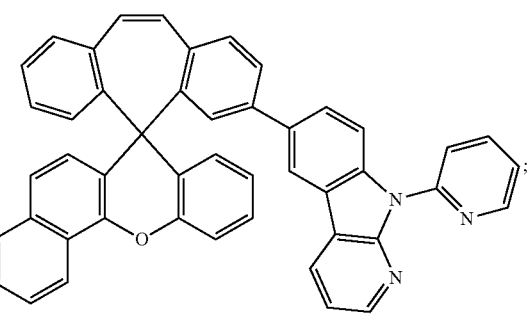
Compound 203
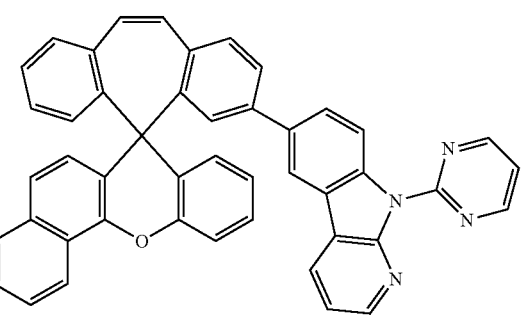

Compound 204
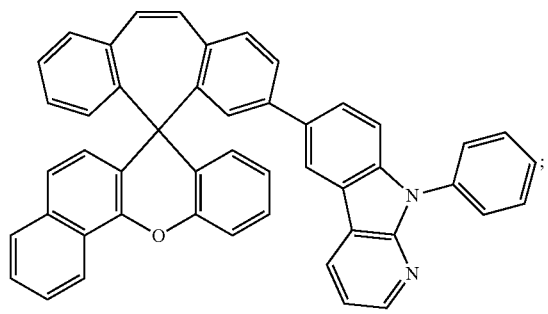
Compound 205
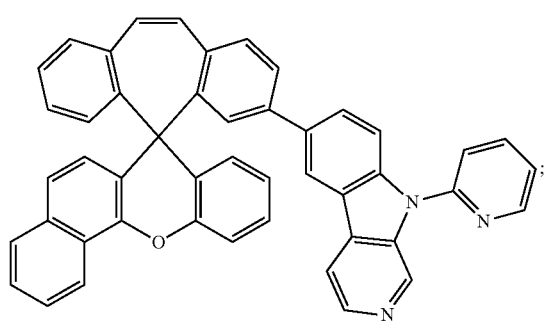
Compound 206
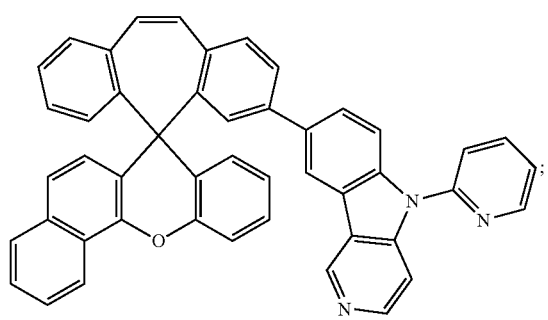
Compound 207
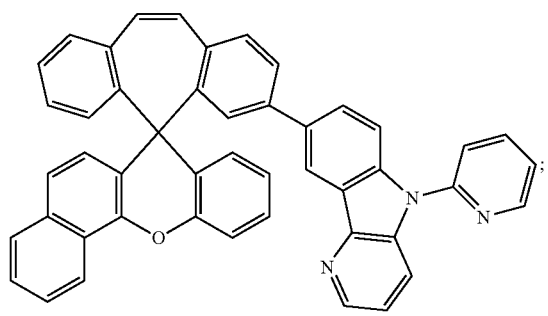
Compound 208
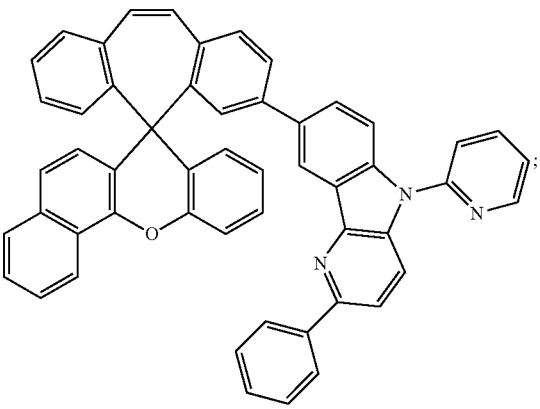
Compound 209
Compound 210
Compound 211
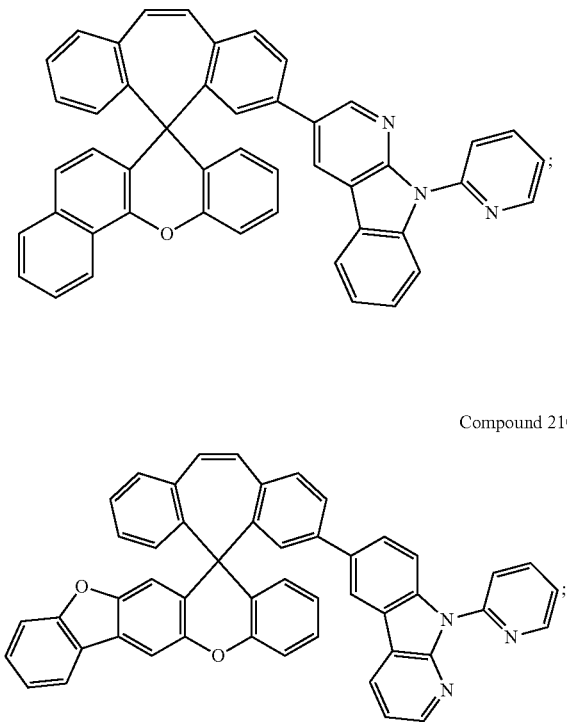

Compound 212
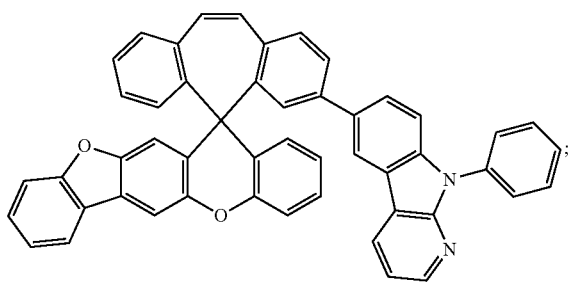
Compound 217
Compound 213
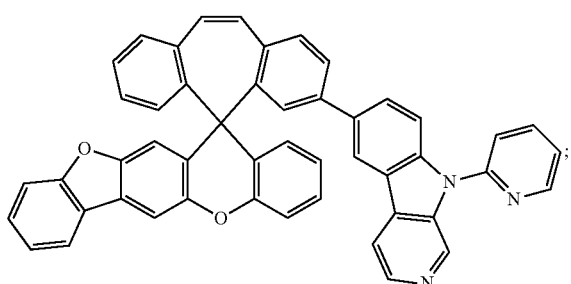
Compound 218
Compound 214
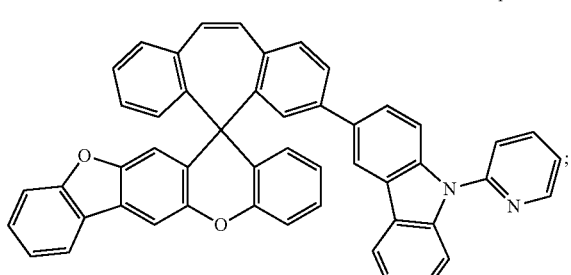
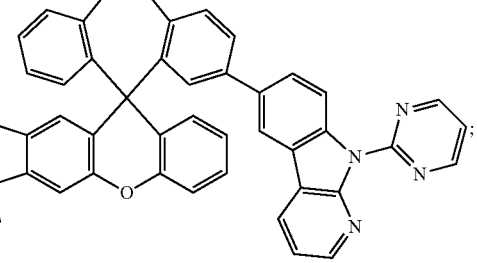
Compound 219
Compound 215
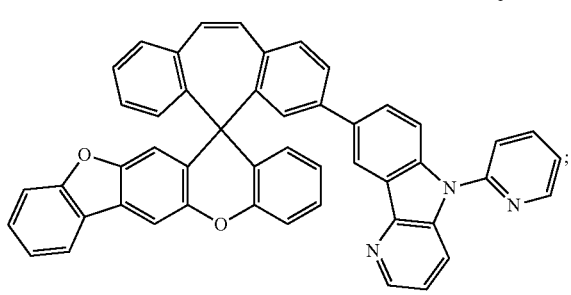
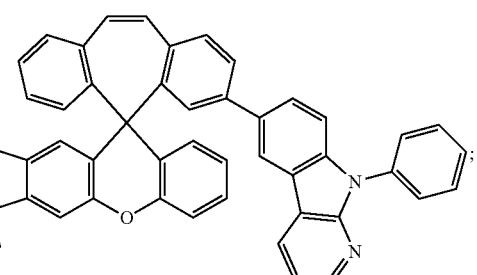
Compound 220
Compound 216
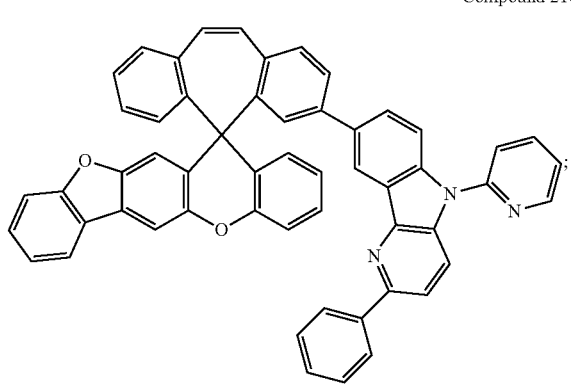
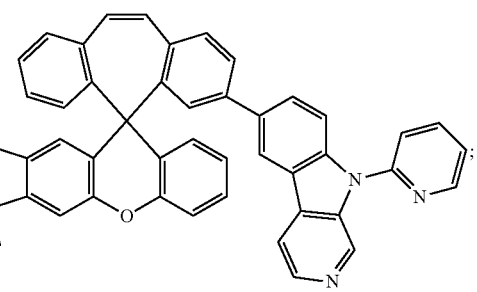
Compound 221

Compound 222
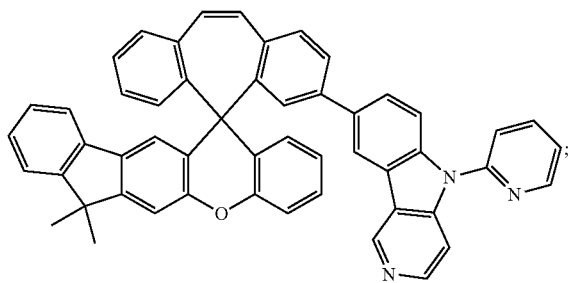
Compound 223
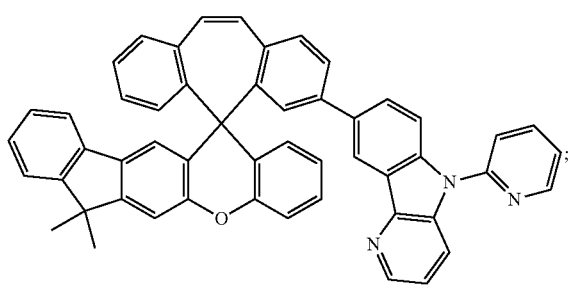
Compound 224
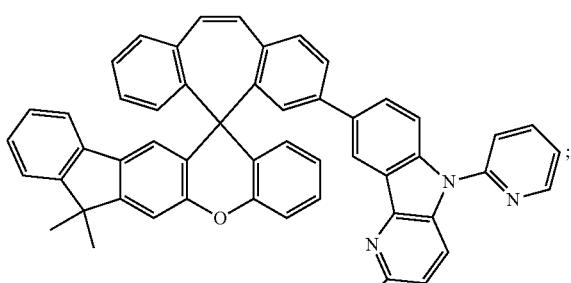
Compound 225
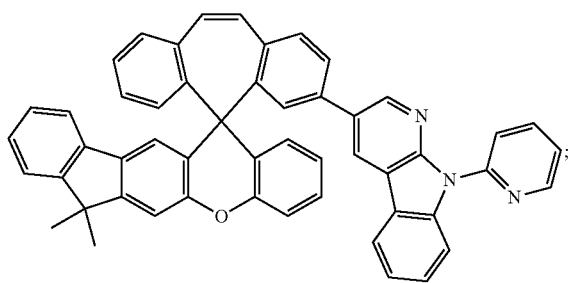
Compound 226
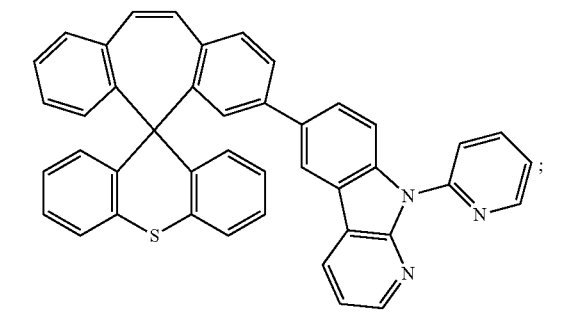
Compound 227
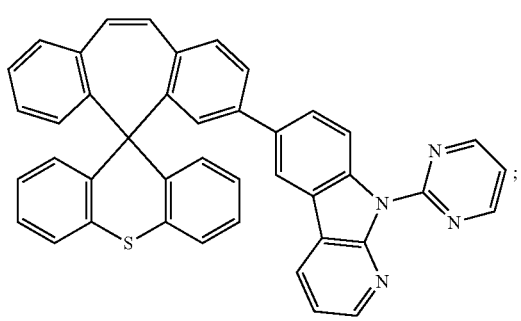
Compound 228
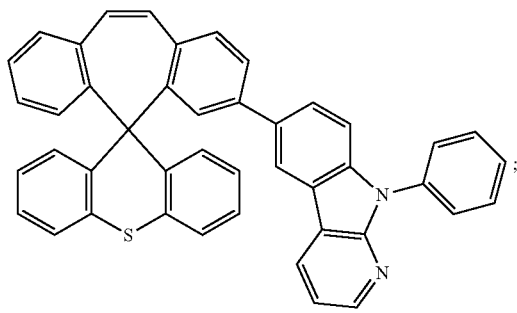
Compound 229
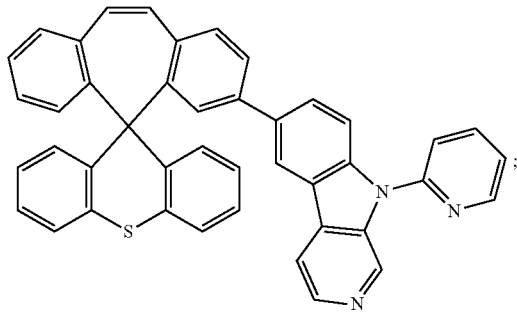
Compound 230
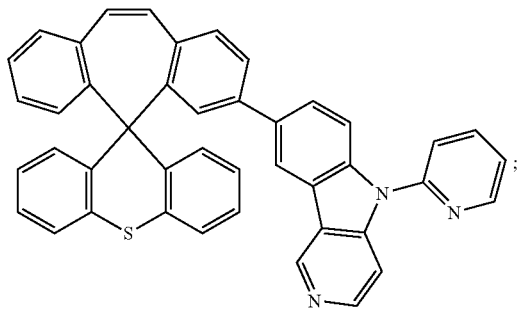

Compound 231
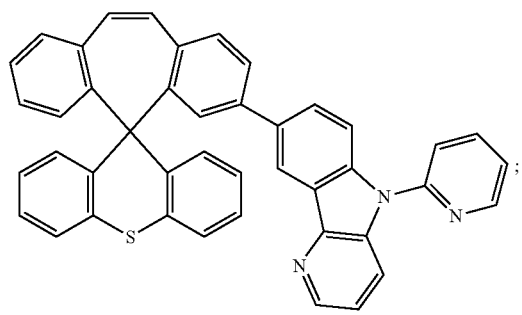
Compound 232
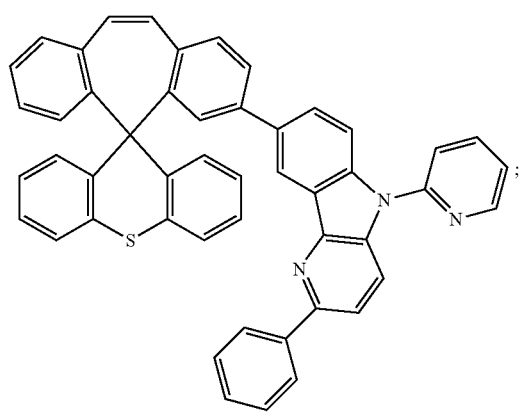
Compound 233
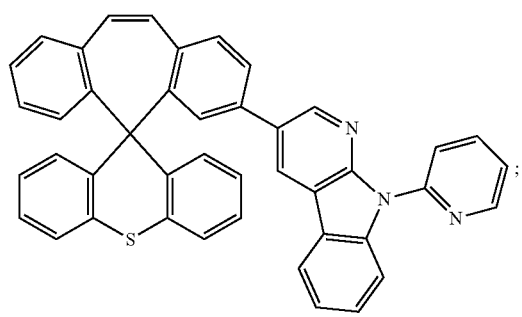
Compound 234
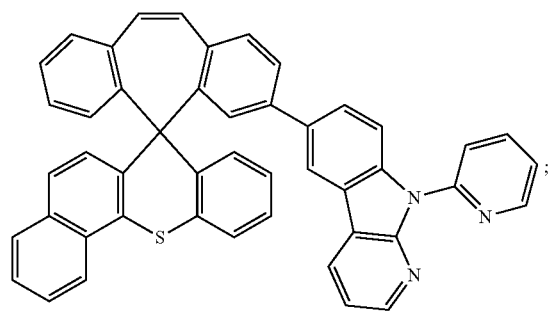
Compound 235
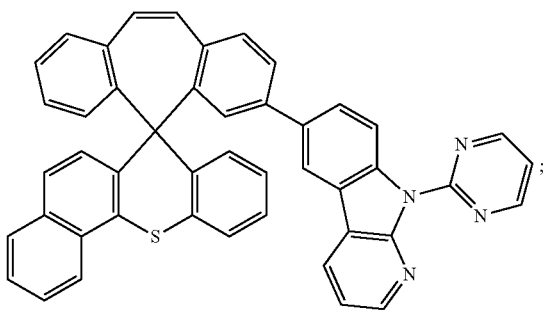
Compound 236
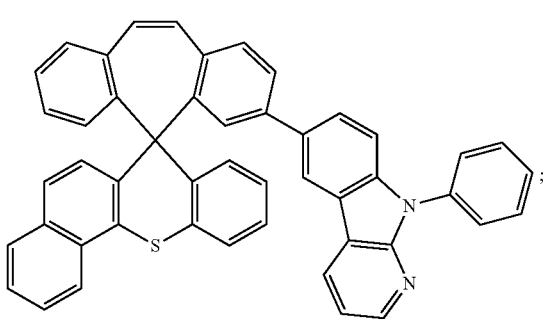
Compound 237
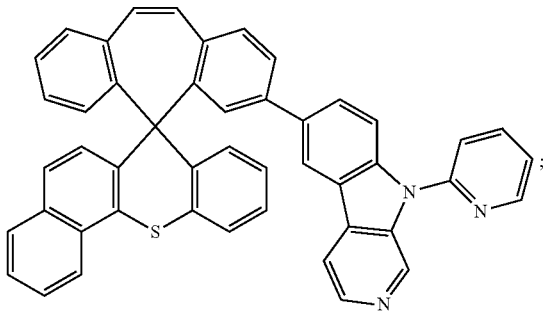
Compound 238
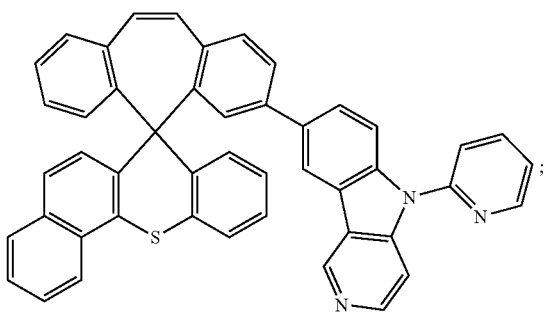

Compound 239
Compound 240
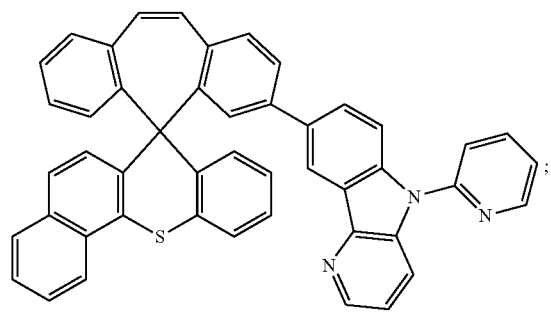
Compound 243
Compound 244
Compound 245
Compound 246
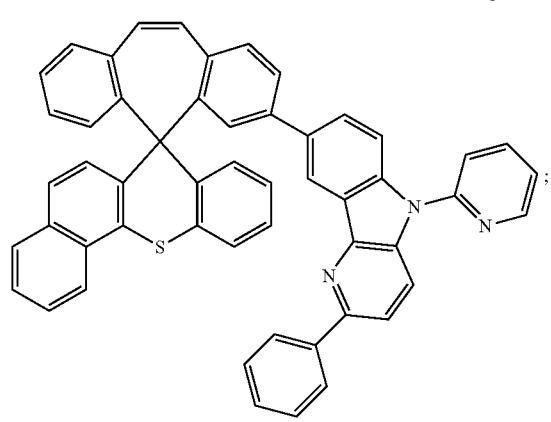
Compound 241
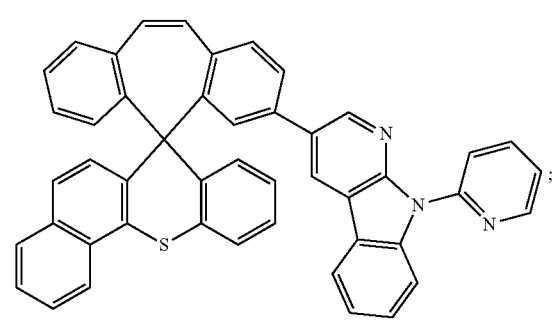
Compound 242
Compound 247
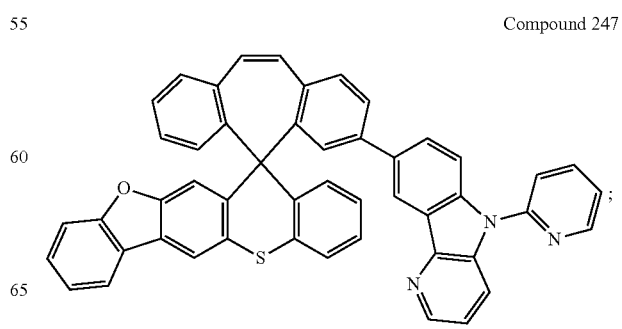

Compound 248
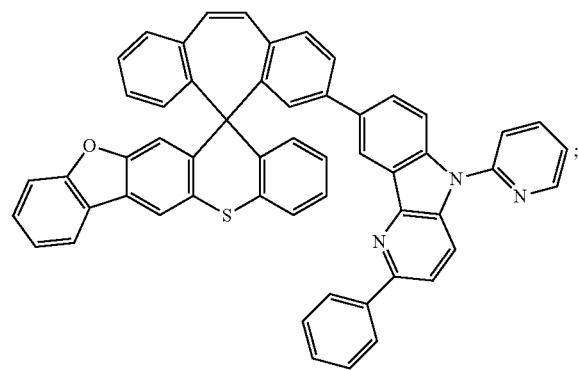
Compound 249
Compound 250
Compound 251
Compound 252
Compound 253
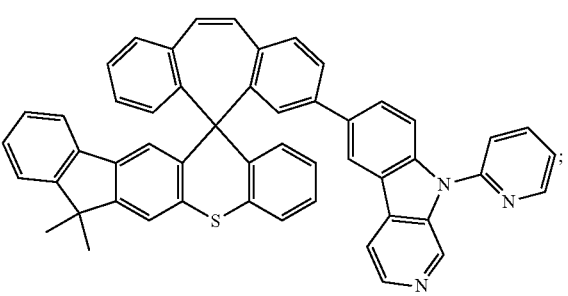
Compound 254
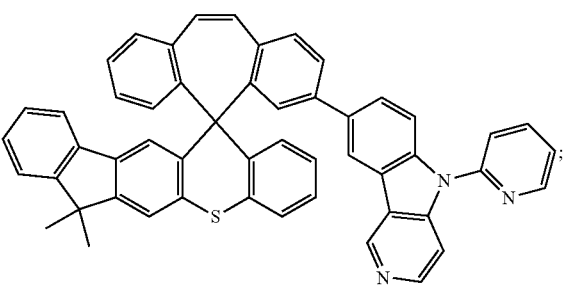
Compound 255
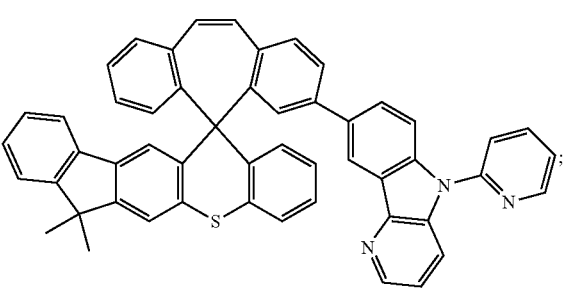
Compound 256
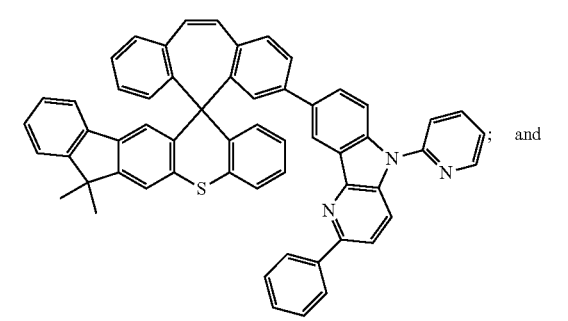
and
Compound 257
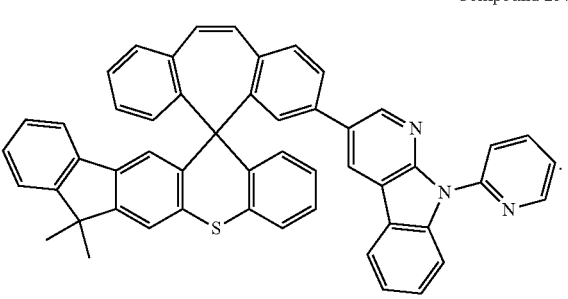
The present invention also provides an organic electronic device, comprising a first electrode, a second electrode, and an organic layer disposed between the first electrode and the second electrode. The organic layer comprises the novel compound as described above.

Preferably, the organic electronic device is an organic light emitting device (OLED). More preferably, the novel compound of the present invention may be used as an electron transport material or a hole blocking layer.

Specifically, the organic light emitting device may comprise:
a hole injection layer formed on the first electrode;
a hole transport layer formed on the hole injection layer;
an emission layer formed on the hole transport layer;
an electron transport layer formed on the emission layer;
an electron injection layer formed between the electron transport layer and the second electrode.

In one embodiment, the organic layer may be the electron transport layer, i.e., the electron transport layer comprises the novel compound as stated above.

Preferably, the hole injection layer may be a two-layered structure, i.e., the OLED comprises a first hole injection layer and a second hole injection layer disposed between the first electrode and the hole transport layer.

Preferably, the hole transport layer may be a two-layered structure, i.e., the OLED comprises a first hole transport layer and a second hole transport layer disposed between the two-layered hole injection layer and the emission layer.

Preferably, the electron transport layer is made of the novel compound such as Compounds 1 to 257. The OLEDs using the novel compound as the electron transport material can have an improved efficiency compared to commercial OLEDs using known electron transport material, such as 2-(4-(9,10-di(naphthalen-2-yl)anthracen-2-yl)phenyl)-1-phenyl-1H-benzo[d]imidazole; bis(2-methyl-8quinolinolato)(p-phenylphenolato) aluminum; and 2-(4-biphenylyl)-5-(4-tert-butylphenyl)-1,3,4-oxadiazole (PBD), as the electron transport material.

Preferably, the OLED comprises a hole blocking layer formed between the electron transport layer and the emission layer, to block holes overflow from the emission layer to the electron transport layer. Said hole blocking layer may be made of the foresaid novel compound, 2,9-dimethyl-4,7-diphenyl-1,10-phenanthroline (BCP) or 2,3,5,6-tetramethyl-phenyl-1,4-(bis-phthalimide) (TMPP), but it is not limited thereto. In another embodiment, the organic layer may be the hole blocking layer, i.e., the hole blocking layer comprises the novel compound as stated above.

Preferably, the OLED comprises an electron blocking layer formed between the hole transport layer and the emission layer, to block electrons overflow from the emission layer to the hole transport layer. Said electron blocking layer may be made of 9,9'-[1,1'-biphenyl]-4,4'-diylbis-9H-carbazole(CBP) or 4,4',4"-tri(N-carbazolyl)-triphenylamine (TCTA), but it is not limited thereto.

In the presence of such a hole blocking layer and/or an electron blocking layer in an OLED, the OLED has a higher luminous efficiency compared to a typical OLED.

Said first and second hole transport layers may be made of, for example, but not limited to: $N^1,N^{1'}$-(biphenyl-4,4'-diyl)bis($N^1$-(naphthalen-1-yl)-$N^4,N^{4'}$-diphenylbenzene-1,4-diamine); or $N^4,N^{4'}$-di(naphthalen-1-yl)-$N^4,N^{4'}$-diphenylbiphenyl-4,4'-diamine (NPB).

Said first and second hole injection layers may be made of, for example, but not limited to, polyaniline or polyethylenedioxythiophene.

Said emission layer can be made of an emission material including a host and a dopant. The host of the emission material is, for example, but not limited to, 9-(4-(naphthalen-1-yl)phenyl)-10-(naphthalen-2-yl) anthracene.

For red OLEDs, the dopant of the emission material is, for example, but not limited to: organometallic compounds of iridium (II) having perylene ligands, fluoranthene ligands or periflanthene ligands. For green OLEDs, the dopant of the emission material is, for example, but not limited to: diaminofluorenes; diaminoanthracenes; or organometallic compounds of iridium (II) having phenylpyridine ligands. For blue OLEDs, the dopant of the emission material is, for example, but not limited to: diaminofluorenes; diaminoanthracenes; diaminopyrenes; or organic metallic compounds of iridium (II) having phenylpyridine ligands. With various host materials of the emission layer, the OLED can emit lights in red, green or blue.

Said electron injection layer may be made of an electron injection material, for example, but not limited to (8-oxidonaphthalen-1-yl)lithium(II).

Said first electrode is, for example, but not limited to, an indium-doped tin oxide electrode.

Said second electrode has a work function lower than that of the first electrode. The second electrode is, for example, but not limited to, an aluminum electrode, an indium electrode, or a magnesium electrode.

Other objectives, advantages and novel features of the invention will become more apparent from the following detailed description when taken in conjunction with the accompanying drawings.

BRIEF DESCRIPTION OF THE DRAWINGS

FIGS. 2 to 18 are respectively $^1$H nuclear magnetic resonance (NMR) spectra of Compounds 1 to 17.

DETAILED DESCRIPTION OF THE PREFERRED EMBODIMENTS

Figure 1:
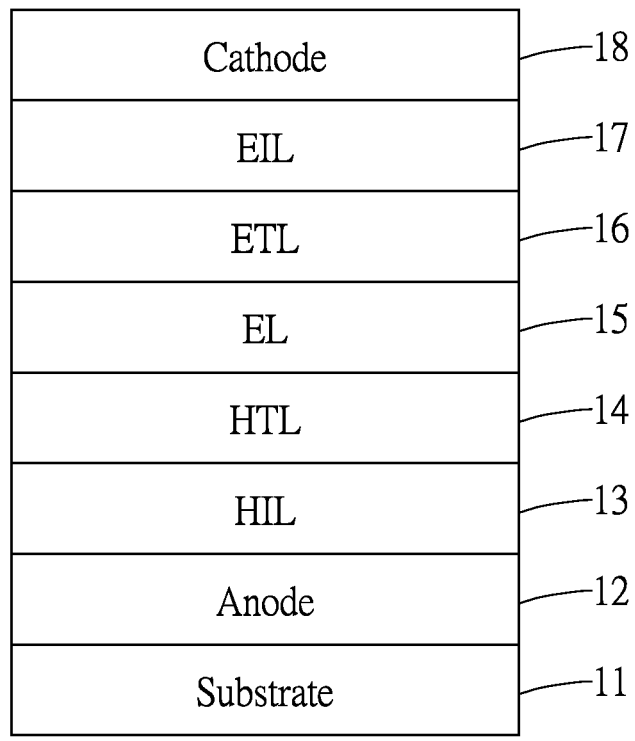
FIG. 1 illustrates a schematic cross-sectional view of an OLED.

Hereinafter, one skilled in the arts can easily realize the advantages and effects of a novel compound and an organic light emitting device using the same in accordance with the present invention from the following examples. It should be understood that the descriptions proposed herein are just preferable examples only for the purpose of illustrations, not intended to limit the scope of the invention. Various modifications and variations could be made in order to practice or apply the present invention without departing from the spirit and scope of the invention.

Synthesis of Intermediate A1

Intermediate A1 used for preparing a novel compound was synthesized by the following steps. The synthesis pathway of the Intermediate A1 was summarized in Scheme A1.

Scheme A1

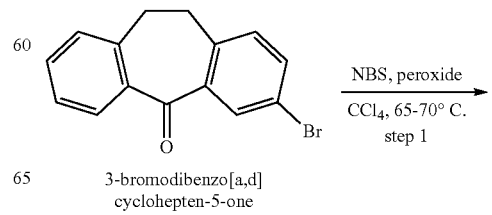

3-bromodibenzo[a,d]
cyclohepten-5-one

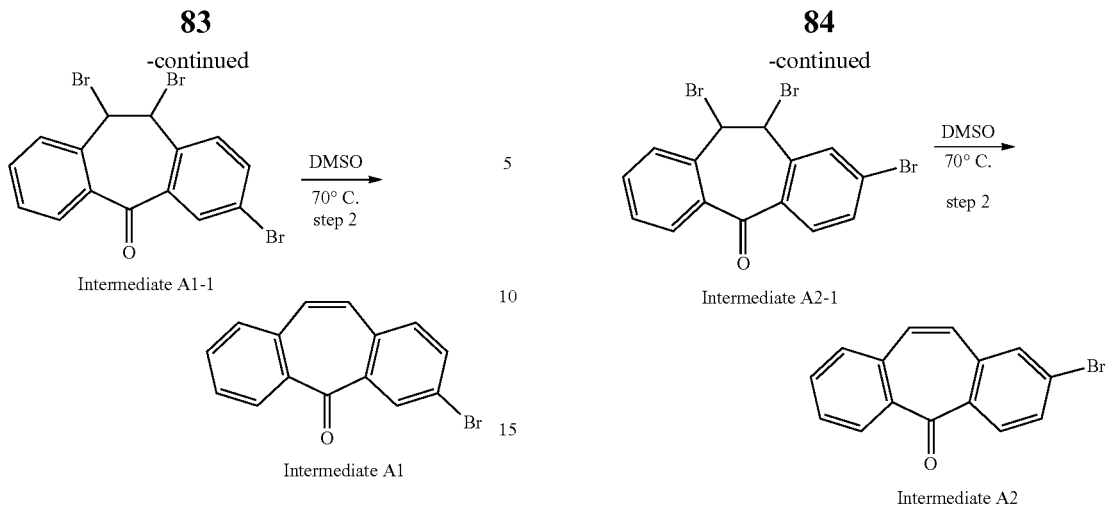

Step 1: Synthesis of Intermediate A1-1

A mixture of 3-bromodibenzo[a,d]cyclohepten-5-one (CAS No. 3973-53-3) (86 g, 1.0 eq), N-bromosuccinimide (NBS) (106 g, 2 eq), benzyl peroxide (0.7 g, 0.01 eq) in carbon tetrachloride ($CCl_4$) (5 times of starting materials) was heated to 65° C. to 70° C. The reaction progress was monitored by high performance liquid chromatography (HPLC). After completion of the reaction, the precipitate was separated by filtration and washed with $CH_3OH$, which was then purified by recrystallization. The purified product was concentrated to dryness, whereby a white solid product was obtained in an amount of 123 g and a yield of 92.3%.

The solid product was identified as Intermediate A1-1 by field desorption mass spectroscopy (FD-MS) analysis. FD-MS analysis: $C_{15}H_9Br_3O$: theoretical value of 444.94 and observed value of 444.94.

Step 2: Synthesis of Intermediate A1

Intermediate A1-1 (1.0 eq) in dimethyl sulfoxide(DMSO) (w/v=1/3 to the reactants) was heated to 70° C. The reaction was monitored by HPLC. After completion of the reaction, the reaction mixture was quenched with ice water. The precipitate was separated by filtration and then purified by column chromatography on silica gel. Intermediate A1 was obtained as pale yellow solid in 93% yield.

The solid product was identified as Intermediate A1 by FD-MS analysis. FD-MS analysis $C_{15}H_9BrO$: theoretical value of 285.14 and observed value of 285.14.

Synthesis of Intermediate A2

Intermediate A2 used for preparing a novel compound was synthesized in a similar manner as Intermediate A1 through steps 1 and 2, except that the starting material 3-bromodibenzo[a,d]cyclohepten-5-one was replaced by 2-bromodibenzo[a,d]cyclohepten-5-one (CAS No. 198707-82-3). The synthesis pathway of Intermediate A2 was summarized in Scheme A2. All intermediates were analyzed according to the methods as described above, and the results were listed in Table 1.

Scheme A2

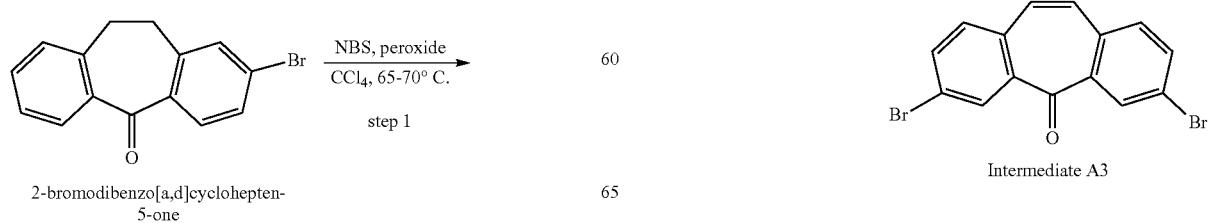

Synthesis of Intermediate A3

Intermediate A3 used for preparing a novel compound was synthesized in a similar manner as Intermediate A1 through steps 1 and 2, except that the starting material 3-bromodibenzo[a,d]cyclohepten-5-one was replaced by 3,7-dibromodibenzo[a,d]cyclohepten-5-one (CAS No. 226946-20-9). The synthesis pathway of Intermediate A3 was summarized in Scheme A3. All intermediates were analyzed as described above, and the results were listed in Scheme A3

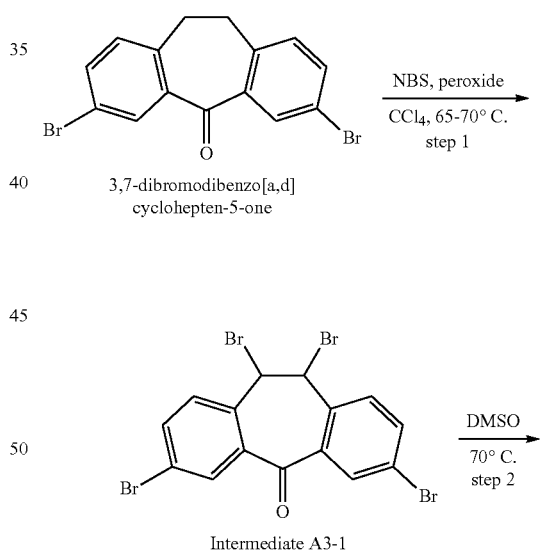

TABLE 1 chemical structures, yields, formulae, and mass ($M^+$) analyzed by FD-MS of intermediates.

| Intermediate | A1-1 | A1 |
|---|---|---|
| Chemical Structure | | |
| Yield | 92.3% | 93% |
| Formula | $C_{15}H_9Br_3O$ | $C_{15}H_9BrO$ |
| Mass($M^+$) | 444.94 | 285.14 |
| Intermediate | A2-1 | A2 |
| Chemical Structure | | |
| Yield | 91.5% | 87% |
| Formula | $C_{15}H_9Br_3O$ | $C_{15}H_9BrO$ |
| Mass($M^+$) | 444.94 | 285.14 |
| Intermediate | A3-1 | A3 |
| Chemical Structure | | |
| Yield | 93.7% | 90% |
| Formula | $C_{15}H_8Br_4O$ | $C_{15}H_8Br_2O$ |
| Mass($M^+$) | 523.84 | 364.03 |

Modifications of Intermediates A1 to A3

In addition to the Intermediates A1 to A3, one person skilled in the art can adopt other starting materials and successfully synthesize other desired intermediates through a reaction mechanism similar to Schemes A1 to A3. Applicable modifications of Intermediates A1 to A3 may be, for example, but not limited to, Intermediates A4 to A15 as follows.

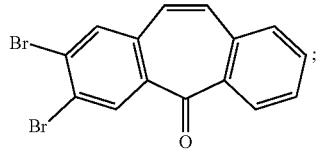

Intermediate A4

-continued

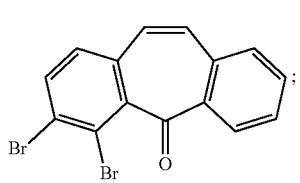

Intermediate A5

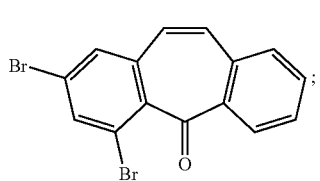

Intermediate A6

-continued

Intermediate A7
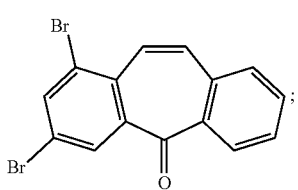

Intermediate A8
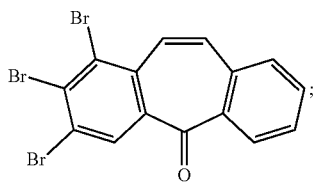

Intermediate A9
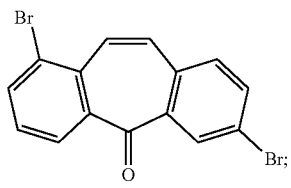

Intermediate A10
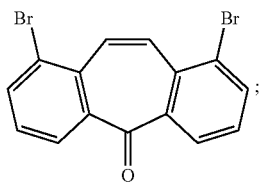

Intermediate A11
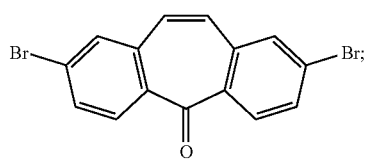

Intermediate A12
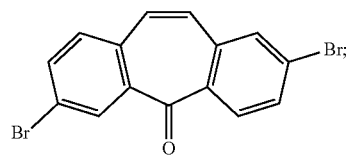

Intermediate A13
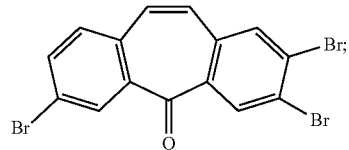

Intermediate A14
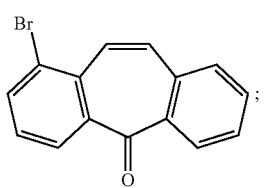

Intermediate A15
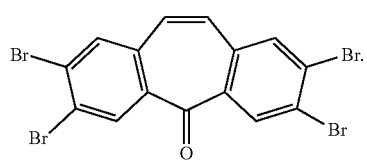

Synthesis of Intermediates B1 to B4

Intermediates B1 to B4 were synthesized by reacting 1-fluoro-2-nitrobenzene and phenol derivatives. A general synthesis pathway for Intermediate Bn was summarized in Scheme B-1. In the following Scheme B-1, "Reactant An" may be any one of Reactants A1 to A4 as listed in Table 2-1, and "Intermediate Bn" may be any one of Intermediates B1 to B4.

Scheme B-1

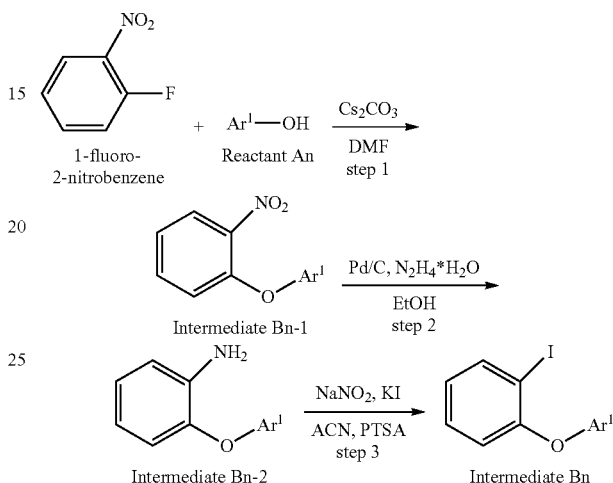

According to Scheme B-1, each of Intermediates B1 to B4 was synthesized by Steps 1 to 3 as follows.

Step 1: Synthesis of Intermediate Bn-1

The mixture of $Ar^1$—OH (referred Reactant An, 1 eq.), 1-fluoro-2-nitrobenzene (50 g, 1 eq.), and cesium carbonate ($Cs_2CO_3$) (230.9 g, eq.) in DMF (2080 ml, 0.17M) was stirred at 90° C. under an argon atmosphere. After the completion of the reaction, DMF was distilled out. The residue was quenched with water, extracted with ethyl acetate (EA) and dried over magnesium sulfate, followed by concentration under reduced pressure after filtration. The crude mixture was purified by silica-gel column chromatography, and then identified as Intermediate Bn-1 by FD-MS analysis. Take Intermediate B1-1 as an example, FD-MS analysis: $C_{12}H_9NO_3$: theoretical value of 215.2 and observed value of 215.2.

Step 2: Synthesis of Intermediate Bn-2

The mixture of intermediate Bn-1 (1 eq.), 5% Pd/C (10 g, 0.015 eq) in $C_2H_5OH$ (680 ml, 0.5M) was stirred at 70° C. Hydrazine monohydrate ($N_2H_4*H_2O$) (31.6 g, 2 eq.) was then slowly added to the mixture. After the completion of the reaction, the solution was filtered through a pad of Celite, followed by concentration under reduced pressure to obtain the product. The product was identified as intermediate Bn-2 by FD-MS analysis. Take Intermediate B1-2 as an example, FD-MS analysis: $C_{12}H_{11}NO$: theoretical value of 185.22 and observed value of 185.22.

Step 3: Synthesis of Intermediate Bn

The mixture of intermediate Bn-2 (1 eq.), p-toluenesulfonic acid monohydrate (PTSA*$H_2O$) (172.5 g, 3 eq) in acetonitrile (ACN)(224 ml, 1.3 M) was cooled to 5° C. by using an ice bath. Sodium nitrite ($NaNO_2$)(41.7 g, 2 eq.) in 240 ml water was added dropwise. After the addition was finished, the mixture was kept at 5° C. 1 hr. The resulting diazonium salt was treated slowly with potassium iodide (KI) (100 g, 2 eq.) in 300 ml water. After the completion of the reaction, the residue was extracted with EA and the combined organic layer was washed with a 10% $Na_2SO_{3(aq)}$ and then dried over $Na_2SO_4$. The organic layer was concentrated under reduced pressure after filtration. The crude mixture was purified by silica-gel column chromatography to obtain intermediate Bn.

The chemical structure of $Ar^1$—OH used for synthesizing Intermediate Bn, i.e., Intermediates B1 to B4, the yield, and the chemical structures of the products obtained in Steps 1 to 3 were listed in Table 2-1. All Intermediates Bn, including Intermediates B1 to B4, were analyzed by FD-MS, and the results were listed in Table 2-1.

TABLE 2-1

Reactant An used for preparing Intermediates B1 to B4, and the chemical structures, yields, formulae, and mass analyzed by FD-MS of Intermediates B1 to B4.

| Reactant An | Intermediate Bn-1 | |
|---|---|---|
| Chemical Structure | Chemical Structure | Yield (%) |
| 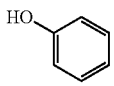<br>Reactant A1 | 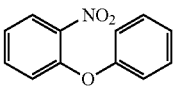 [SMILES: O=[N+]([O-])c1ccccc1Oc1ccccc1]<br>Intermediate B1-1 | 89.2% |
| 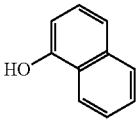<br>Reactant A2 | 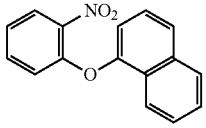 [SMILES: O=[N+]([O-])c1ccccc1Oc1cccc2ccccc12]<br>Intermediate B2-1 | 92% |
| 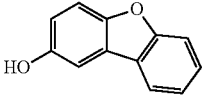 [SMILES: Oc1ccc2oc3ccccc3c2c1]<br>Reactant A3 | 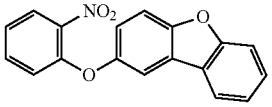 [SMILES: O=[N+]([O-])c1ccccc1Oc1ccc2oc3ccccc3c2c1]<br>Intermediate B3-1 | 91.6% |
| 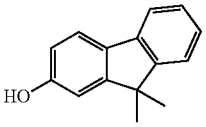 [SMILES: CC1(C)c2ccccc2-c2ccc(O)cc21]<br>Reactant A4 | 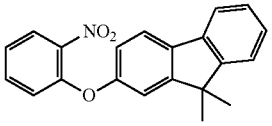 [SMILES: CC1(C)c2ccccc2-c2ccc(Oc3ccccc3[N+](=O)[O-])cc21]<br>Intermediate B4-1 | 93% |

| Intermediate Bn-2 | | Intermediate Bn | |
|---|---|---|---|
| Chemical Structure | Yield (%) | Chemical Structure | Yield (%)/ Formula/ Mass ($M^+$) |
| 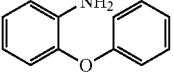<br>Intermediate B1-2 | 95.7% | 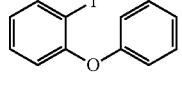<br>Intermediate B1 | 78.2%/ $C_{12}H_9IO$/ 296.1 |
| 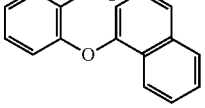<br>Intermediate B2-2 | 95.3% | 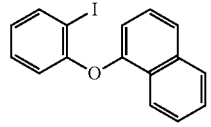 [SMILES: Ic1ccccc1Oc1cccc2ccccc12]<br>Intermediate B2 | 83%/ $C_{16}H_{11}IO$/ 346.16 |

TABLE 2-1-continued

Reactant An used for preparing Intermediates B1 to B4, and the chemical structures, yields, formulae, and mass analyzed by FD-MS of Intermediates B1 to B4.

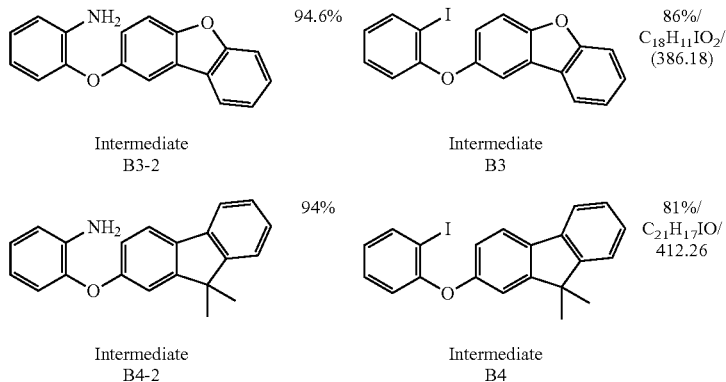

| | | |
|---|---|---|
| Intermediate B3-2 | 94.6% | Intermediate B3 — 86% / $C_{18}H_{11}IO_2$ / (386.18) |
| Intermediate B4-2 | 94% | Intermediate B4 — 81% / $C_{21}H_{17}IO$ / 412.26 |

Synthesis of Intermediate B5 to B8

Unlike Intermediates B1 to B4, Intermediates B5 to B8 were synthesized by reacting 2-bromobenzenethiol and aryl iodide. Another general synthesis pathway for Intermediate Bn was summarized in Scheme B-2. In the following Scheme B-2, "Reactant An" may be any one of Reactants A5 to A8 as listed in Table 2-2 or the like, and "Intermediate Bn" may be any one of Intermediates B5 to B8.

Scheme B-2

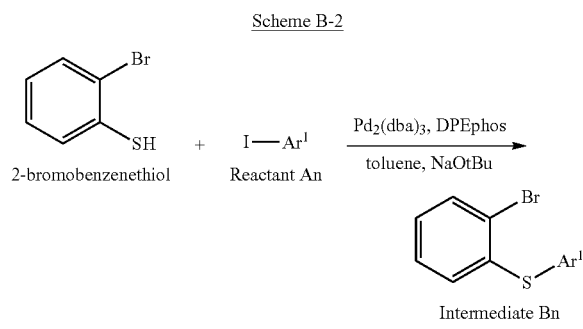

According to the Scheme B-2, a mixture of tris(dibenzylideneacetone)dipalladium(0) ($Pd_2(dba)_3$)(0.5% eq), bis[(2-diphenylphosphino)phenyl] ether (DPEphos) (0.01 eq), and sodium tert-butoxide (NaOtBu) (1.5 eq) was added to a screw-cap vial followed by toluene and a stir bar. I—Ar¹ (referred Reactant An, 1 eq.) and 2-bromobenzenethiol (1.05 eq) were added. The vial was sealed and the mixture was stirred at 100° C. for 1 h. The crude mixture was filtered through a pad of Celite and the filtrate was concentrated. The residue was purified by filtration through a short column of silica gel and eluted with heptane to give Intermediate Bn.

The chemical structure of Ar¹—I used for synthesizing Intermediate Bn, i.e., Intermediates B5 to B8, the chemical structures of the Intermediate Bn, and the yield were listed in Table 2-2. All Intermediates Bn, including Intermediates B5 to B8, were analyzed by FD-MS, and the results were listed in Table 2-2.

Table 2-2: Reactant An used for preparing Intermediates B5 to B8, and the chemical structures, yields, formulae, and mass analyzed by FD-MS of Intermediates B5 to B8.

| Reactant An Chemical Structure | Intermediate B Chemical Structure | Yield | Formula/ Mass (M⁺) |
|---|---|---|---|
| 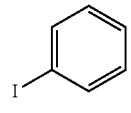 Reactant A5 | 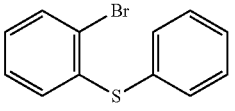 [SMILES: Brc1ccccc1Sc1ccccc1] Intermediate B5 | 85.6% | $C_{12}H_9BrS$ / 265.17 |
| 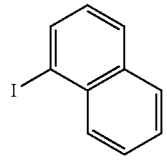 Reactant A6 | 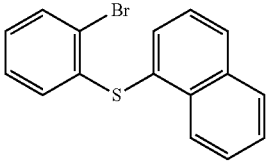 [SMILES: Brc1ccccc1Sc1cccc2ccccc12] Intermediate B6 | 83.7% | $C_{16}H_{11}BrS$ / 315.23 |

| Reactant An Chemical Structure | Intermediate B Chemical Structure | Yield | Formula/ Mass (M+) |
|---|---|---|---|
| 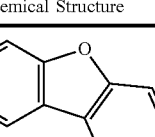 Reactant A7 | 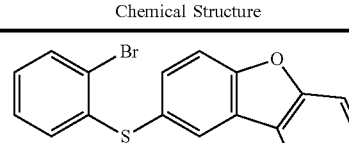 Intermediate B7 | 80.5% | $C_{18}H_{11}BrOS$/ 355.25 |
| 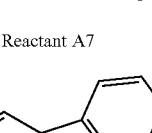 Reactant A8 | 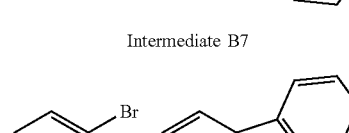 Intermediate B8 | 88% | $C_{21}H_{17}BrS$/ 381.33 |

Modifications of Intermediates B1 to B4

In addition to the Intermediates B1 to B4, one person skilled in the art can adopt any halonitrobenzenes other than 1-fluoro-2-nitrobenzene and any phenol derivatives other than Reactants A1 to A4 to successfully synthesize other desired Intermediate Bn through a reaction mechanism similar to Scheme B-1. Applicable modifications of Intermediates B1 to B4 may be, for example, but not limited to, Intermediates B9 to B20 as follows.

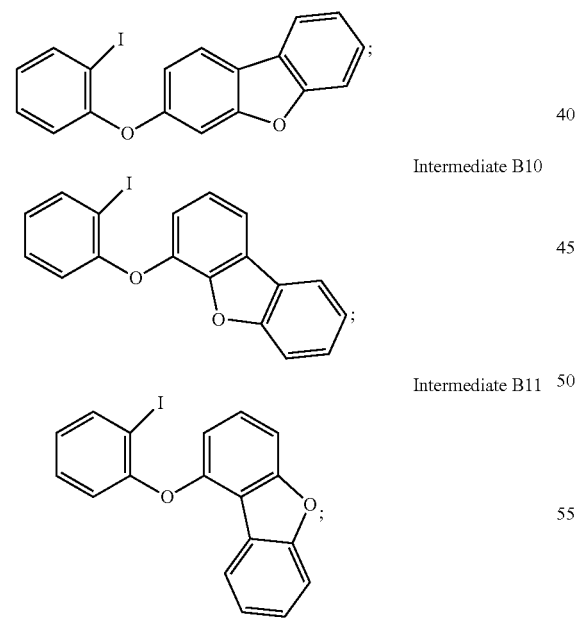

Intermediate B9

Intermediate B10

Intermediate B11

Intermediate B12

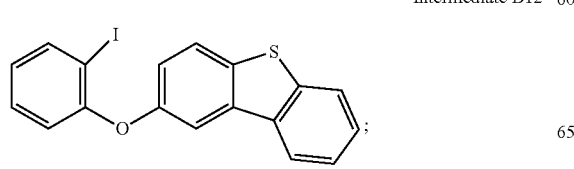

-continued

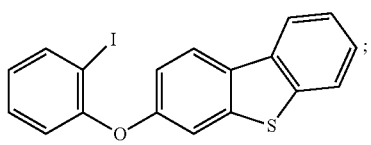

Intermediate B13

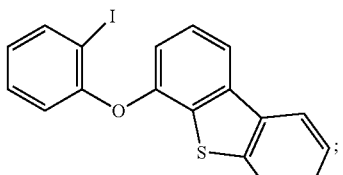

Intermediate B14

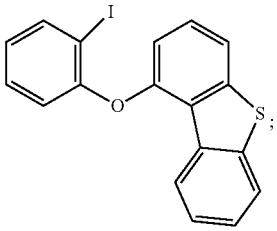

Intermediate B15

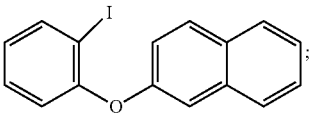

Intermediate B16

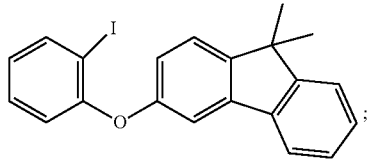

Intermediate B17

Intermediate B18

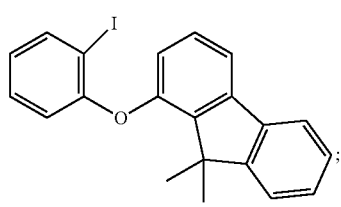

Intermediate B19

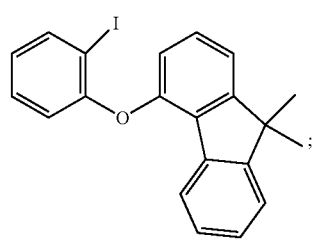

Intermediate B20

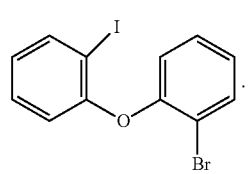

Modifications of Intermediates B5 to B8

In addition to the Intermediates B5 to B8, one person skilled in the art can adopt any halobenzenethiols other than 2-bromonzenethiol and any aryl iodidesother other than Reactants A5 to A8 to successfully synthesize other desired Intermediate Bn through a reaction mechanism similar to Scheme B-2. Applicable modifications of Intermediates B5 to B8 may be, for example, but not limited to, Intermediates B21 to B36 as follows.

Intermediate B21

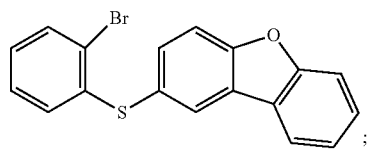

Intermediate B22

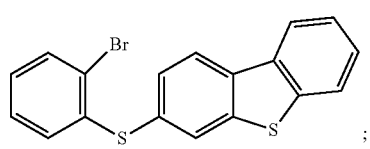

Intermediate B23

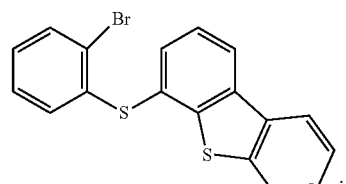

Intermediate B24

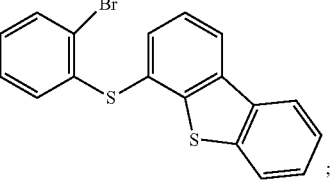

Intermediate B25

Intermediate B26

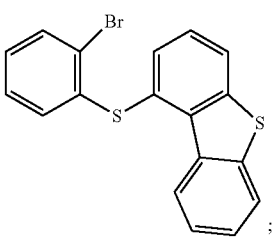

Intermediate B27

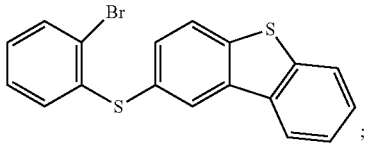

Intermediate B28

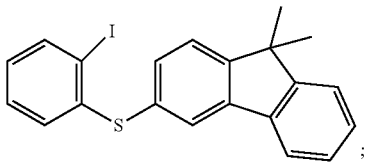

Intermediate B29

Intermediate B30

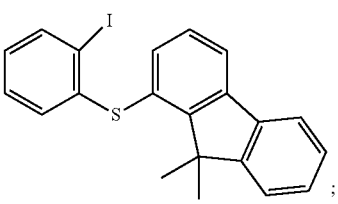

Intermediate B31

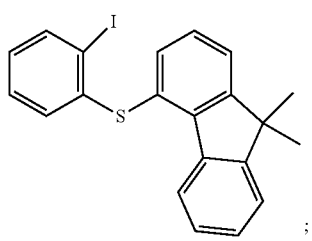

Intermediate B32

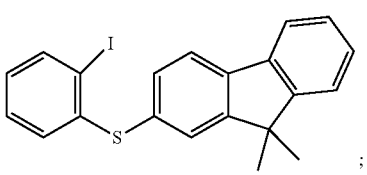

Intermediate B33

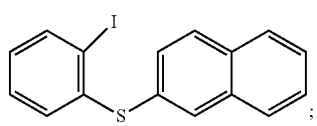

Intermediate B34

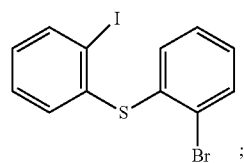

Intermediate B35

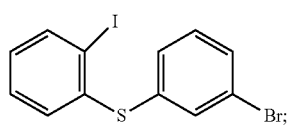

Intermediate B36

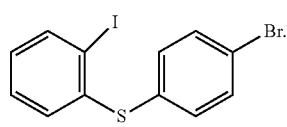

Synthesis of Intermediate Cn

The foresaid Intermediates B1 to B36, especially Intermediates B1 to B8, could be further adopted to synthesize Intermediate Cn. A general synthesis pathway for Intermediate Cn was summarized in Scheme C-1. In the following Scheme C-1, "Intermediate An" may be any one of foresaid Intermediates A1 to A15 or the like, "Intermediate Bn" may be any one of foresaid Intermediates B1 to B36 or the like, and "Intermediate Cn" may be any one of Intermediates C1 to C10 as listed in Table 3-1 or the like. Intermediates C1 to C10 were each synthesized by the following steps.

Scheme C-1

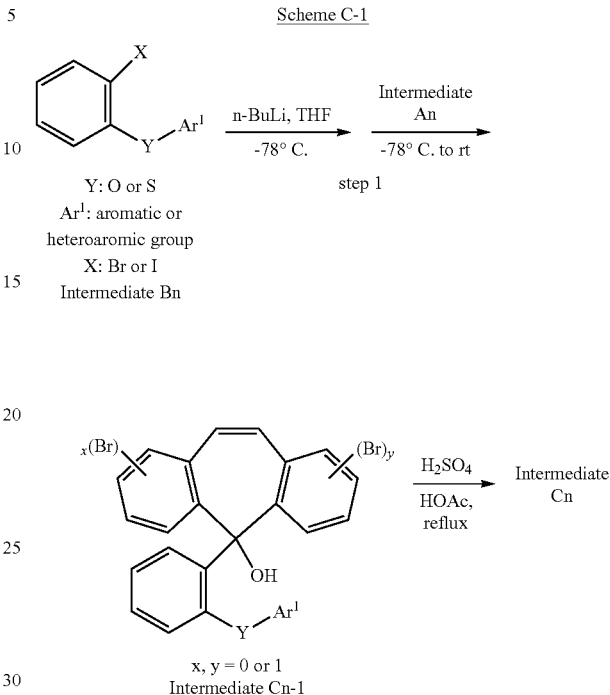

Step 1: Synthesis of Intermediate Cn-1

Intermediate Bn (1.0 eq) was dissolved in 120 mL of anhydrous tetrahydrofuran (THF) (0.4M), and cooled to −78° C. n-Butyllithium (n-BuLi)(2.5 M, 1.0 eq) was slowly added to the above cooled solution, and the reaction mass was stirred for 1 h. After 1 h of stirring, Intermediate An (0.7 eq) was added to the reaction solution and stirred for additional 3 h at 25° C. After the completion of the reaction, it was quenched by saturated solution of ammonium chloride, and extracted with organic solvent. The organic layer was separated, concentrated, and recrystallized with petroleum ether to obtain a white solid product.

The white solid product was analyzed by FD-MS, and the result was listed in Table 3-1. The chemical structures of Intermediates Cn-1 were listed in Table 3-1.

Step 2: Synthesis of Intermediate Cn

The foresaid Intermediate Cn-1 (1.0 eq), acetic acid (w/v=1/3 to the reactants) and $H_2SO_4$ (5 drops) were mixed, and then stirred at 110° C. for 6 h. The solvent was then removed under reduced pressure, and the residue was purified with column chromatography. The residual mass was recrystallized with toluene to obtain a white solid product.

The solid product was identified by FD-MS analysis. The chemical structures, yields, formulae, and mass analyzed by FD-MS of Intermediates C1 to C10 were listed in Table 3-1.

TABLE 3-1

Intermediates An and Bn used for preparing Intermediates C1 to C10, chemical structures of Intermediates Cn-1, and chemical structures of Intermediates Cn, yields, formulae, and mass analyzed by FD-MS of Intermediates C1 to C10.

| Intermediate An | Intermediate Bn | Intermediate Cn-1 Chemical Structure | Yield (%) | Intermediate Cn Chemical Structure/ Formula/ Mass (M+) | Yield (%) |
|---|---|---|---|---|---|
| A1 | B1 | Intermediate C1-1/ C$_{27}$H$_{19}$BrO$_2$/ 455.34 | 86 | Intermediate C1/ C$_{27}$H$_{17}$BrO/ 437.33 | 86 |
| A3 | B1 | Intermediate C2-1 | 84 | Intermediate C2/ C$_{27}$H$_{16}$Br$_2$O/ 516.22 | 86 |
| A1 | B2 | Intermediate C3-1 | 85 | Intermediate C3 | 89 |
| A1 | B3 | Intermediate C4-1 | 92 | Intermediate C4 | 93 |

TABLE 3-1-continued

Intermediates An and Bn used for preparing Intermediates C1 to C10, chemical structures of Intermediates Cn-1, and chemical structures of Intermediates Cn, yields, formulae, and mass analyzed by FD-MS of Intermediates C1 to C10.

| Intermediate An | Intermediate Bn | Intermediate Cn-1 Chemical Structure | Yield (%) | Intermediate Cn Chemical Structure/ Formula/ Mass (M+) | Yield (%) |
|---|---|---|---|---|---|
| A1 | B4 | 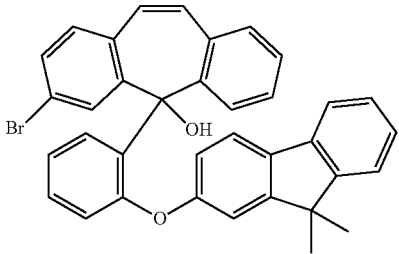 [SMILES: CC1(C)c2ccccc2-c2ccc(Oc3ccccc3C3(O)c4ccccc4C=Cc4ccc(Br)cc43)cc21]<br>Intermediate C5-1 | 80 | 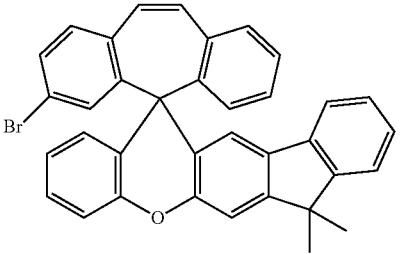<br>Intermediate C5 | 87 |
| A1 | B5 | 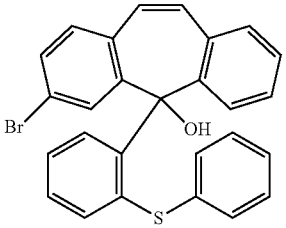 [SMILES: OC1(c2ccccc2Sc2ccccc2)c2ccccc2C=Cc2ccc(Br)cc21]<br>Intermediate C6-1 | 85 | 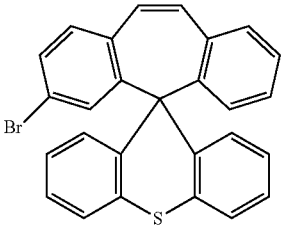<br>Intermediate C6 | 80 |
| A2 | B5 | 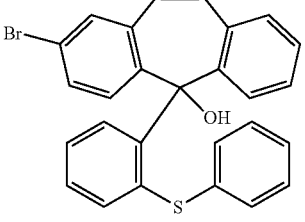<br>Intermediate C7-1 | 77 | 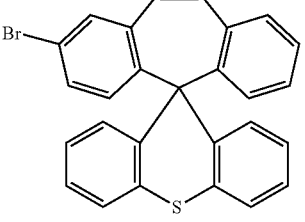<br>Intermediate C7 | 92 |
| A1 | B6 | 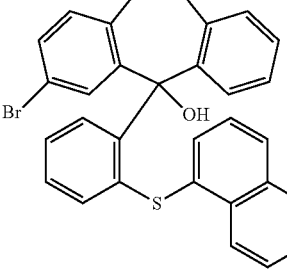<br>Intermediate C8-1 | 80 | 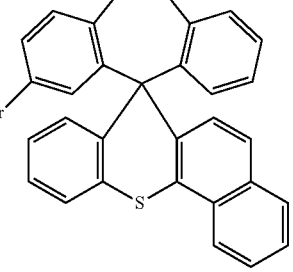<br>Intermediate C8 | 84 |

TABLE 3-1-continued

Intermediates An and Bn used for preparing Intermediates C1 to C10, chemical structures of Intermediates Cn-1, and chemical structures of Intermediates Cn, yields, formulae, and mass analyzed by FD-MS of Intermediates C1 to C10.

| Intermediate An | Intermediate Bn | Intermediate Cn-1 Chemical Structure | Yield (%) | Intermediate Cn Chemical Structure/ Formula/ Mass (M+) | Yield (%) |
|---|---|---|---|---|---|
| A1 | B7 | 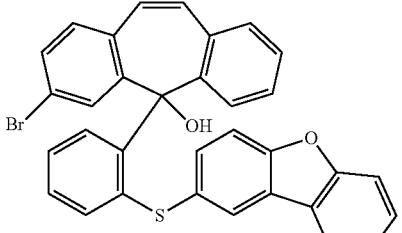 Intermediate C9-1 | 76 | 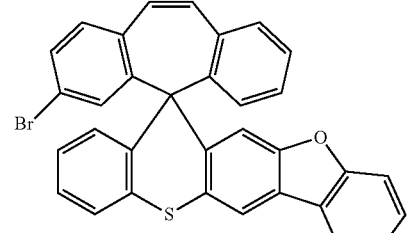 Intermediate C9 | 82 |
| A1 | B8 | 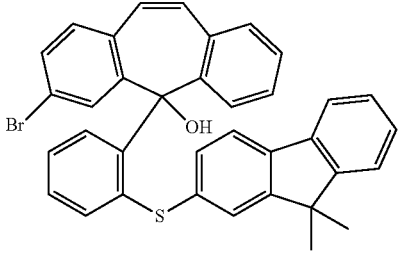 Intermediate C10-1 | 77 | 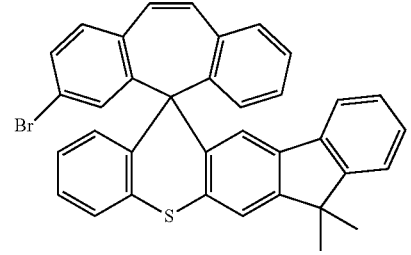 Intermediate C10 | 90 |

Modifications of Intermediates C1 to C10

In addition to the Intermediates C1 to C10, one person skilled in the art can adopt any intermediate An other than Intermediates A1 to A3 and any Intermediate Bn other than Intermediates B1 to B8 to successfully synthesize other desired Intermediate Cn through a reaction mechanism similar to Scheme C-1. Applicable modifications of Intermediates C1 to C10 may be, for example, but not limited to, Intermediates C11 to C50 as follows.

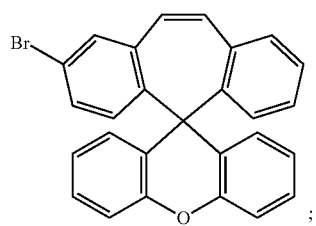

Intermediate C11

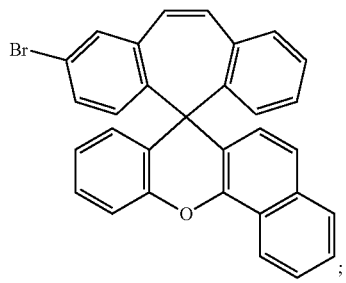

Intermediate C12

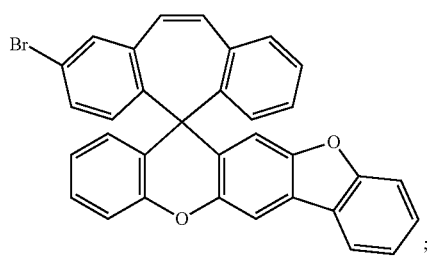

Intermediate C13

Intermediate C14
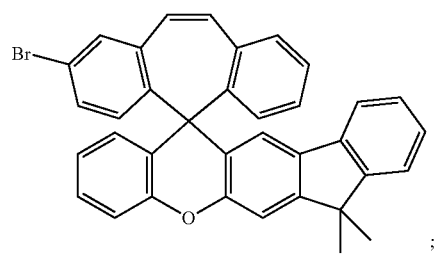
;
Intermediate C15
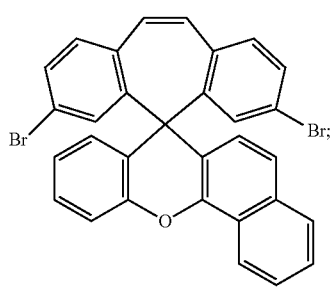
;
Intermediate C16
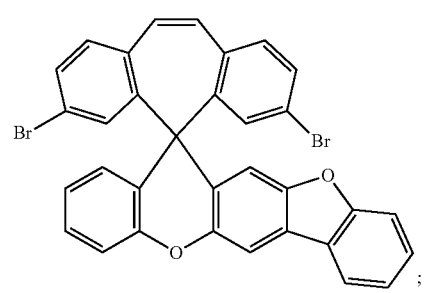
;
Intermediate C17
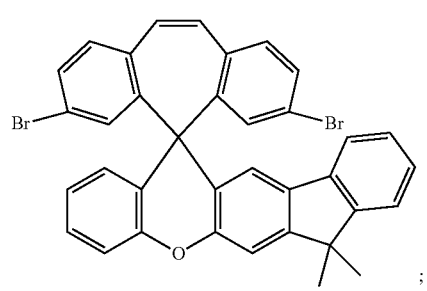
;
Intermediate C18
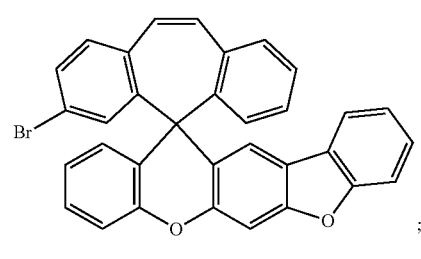
;
Intermediate C19
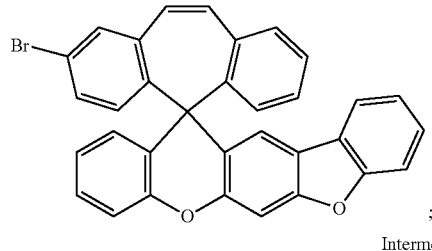
;
Intermediate C20
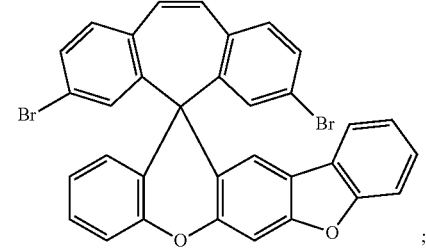
;
Intermediate C21
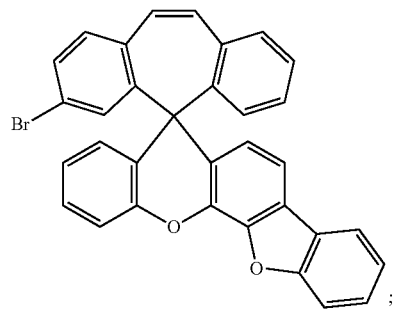
;
Intermediate C22
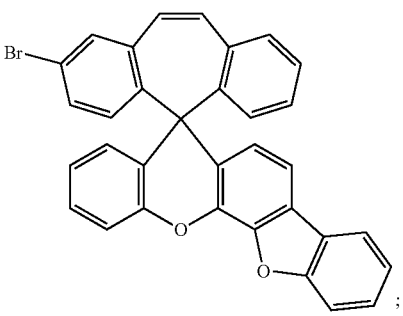
;
Intermediate C23
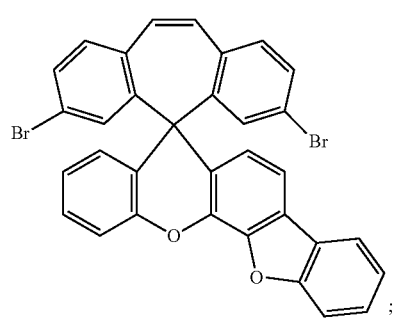
;

Intermediate C24
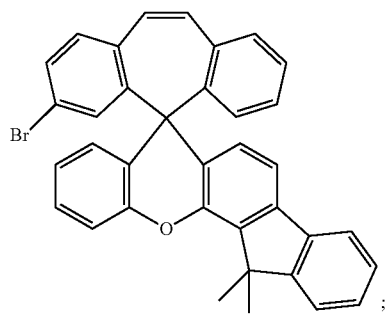
Intermediate C25
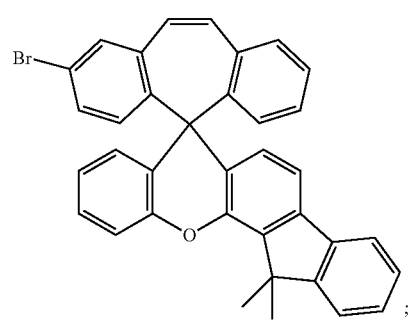
Intermediate C26
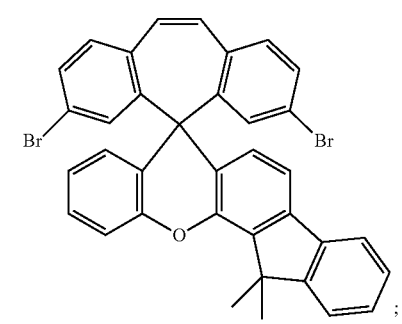
Intermediate C27
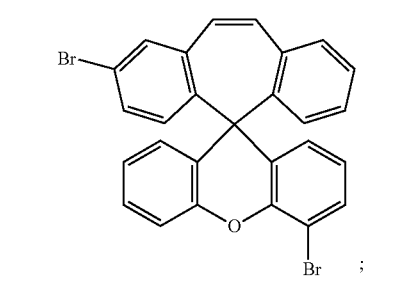
Intermediate C28
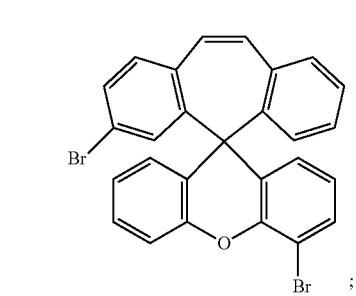
Intermediate C29
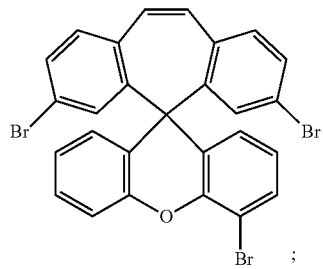
Intermediate C30
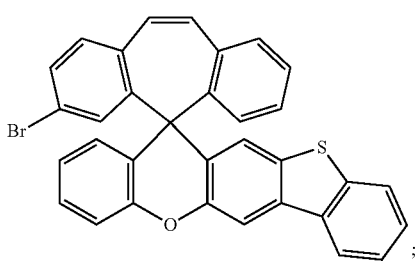
Intermediate C31
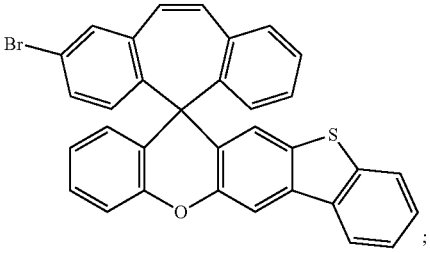
Intermediate C32
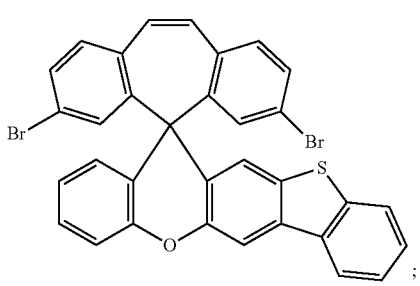
Intermediate C33
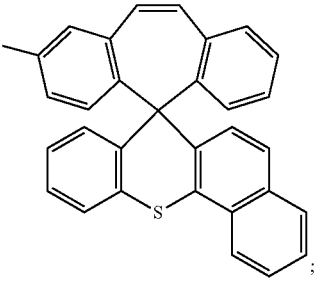

-continued
Intermediate C34
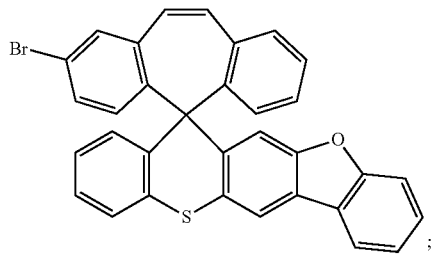
Intermediate C35
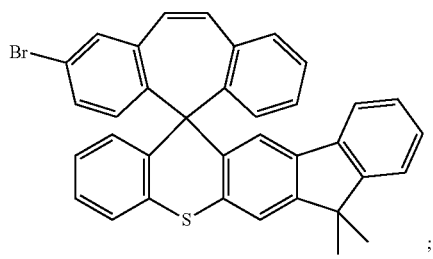
Intermediate C36
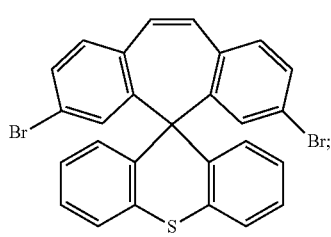
Intermediate C37
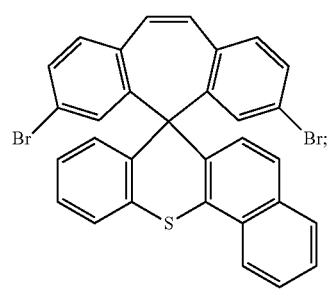
Intermediate C38
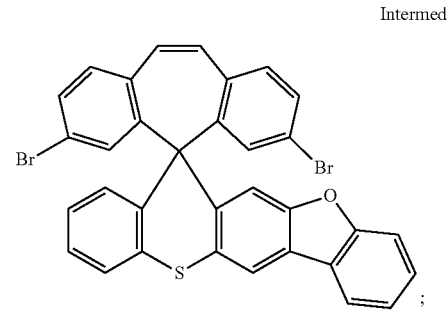
-continued
Intermediate C39
Intermediate C40
Intermediate C41
Intermediate C42
Intermediate C43
Intermediate C44

-continued

Intermediate C45

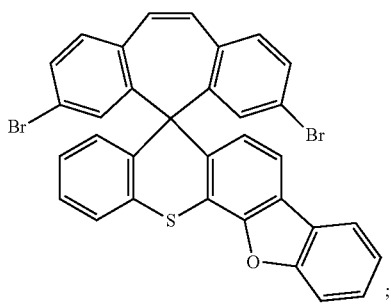

Intermediate C46

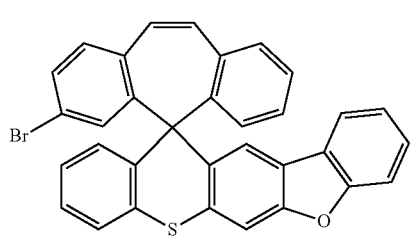

Intermediate C47

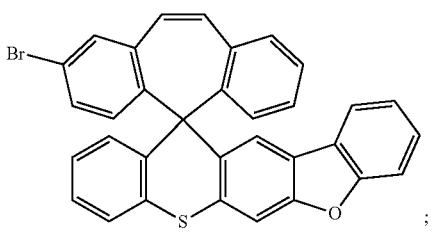

Intermediate C48

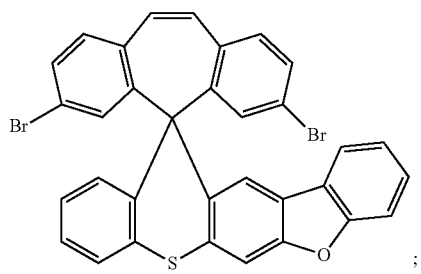

Intermediate C49

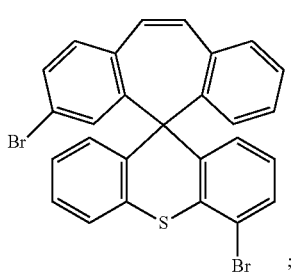

-continued

Intermediate C50

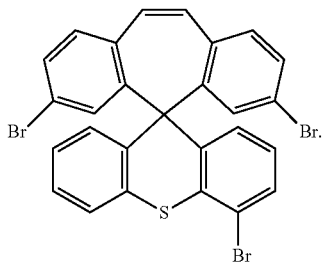

Synthesis of Intermediate Cn-B

The foresaid Intermediate Cn could be further modified into an Intermediate Cn-B through Miyaura borylation reaction. "Intermediate Cn-B" was directed to a compound derived from Intermediate Cn whose bromo group was replaced by (pinacolato)boron group. A synthesis pathway of Intermediate Cn-B was summarized in Scheme C1-B. Intermediate Cn-B was synthesized by the following steps.

Scheme C1-B

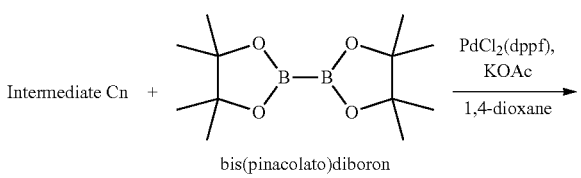

bis(pinacolato)diboron

Intermediate Cn-B

A mixture of bis(pinacolato)diboron (1.2 eq), Intermediate Cn (1.0 eq), 1,1-bis(diphenylphosphino)-ferrocene dichloropalladium (II) (PdCl$_2$(dppf)) (0.015 eq), and potassium acetate (KOAc) (3.0 eq) in 1,4-dioxane (0.3 M) was stirred at 110° C. for 8 hours under nitrogen atmosphere. After cooling to room temperature, the solvent was then removed under reduced pressure, and the residue was purified via column chromatography to obtain a pale yellow solid product.

The pale yellow solid product was identified by FD-MS analysis. The chemical structures, yields, formulae, and mass analyzed by FD-MS of Intermediates Cn-B were listed in Table 3-2.

TABLE 3-2

Intermediate Cn used for preparing Intermediate Cn-B and chemical structures, yields, formulae, and mass analyzed by FD-MS of Intermediates Cn-B.

| Intermediate Cn | | Intermediate Cn-B | | |
| --- | --- | --- | --- | --- |
| Chemical Structure | Yield (%) | Chemical Structure | Yield (%) | Formula/ Mass (M+) |
| Intermediate C1 | 86 | Intermediate C1-B | 96 | $C_{33}H_{29}BO_3$/ 484.39 |
| Intermediate C3 | 89 | Intermediate C3-B | 95 | $C_{37}H_{31}BO_3$/ 534.45 |
| Intermediate C4 | 93 | Intermediate C4-B | 93 | $C_{39}H_{31}BO_4$/ 574.47 |
| Intermediate C5 | 87 | Intermediate C5-B | 92 | $C_{42}H_{37}BO_3$/ 600.55 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| Intermediate C6 | 80 | Intermediate C6-B | 96 | $C_{33}H_{29}BO_2S$ / 500.46 |
| Intermediate C7 | 92 | Intermediate C7-B | 94 | $C_{33}H_{29}BO_2S$ / 500.46 |
| Intermediate C8 | 84 | Intermediate C8-B | 90 | $C_{37}H_{31}BO_2S$ / 550.52 |
| Intermediate C9 | 82 | Intermediate C9-B | 94 | $C_{39}H_{31}BO_3S$ / 590.54 |

TABLE 3-2-continued

Intermediate Cn used for preparing Intermediate Cn-B and chemical structures, yields, formulae, and mass analyzed by FD-MS of Intermediates Cn-B.

| Intermediate Cn | | Intermediate Cn-B | | |
|---|---|---|---|---|
| Chemical Structure | Yield (%) | Chemical Structure | Yield (%) | Formula/ Mass (M+) |
| Intermediate C10 | 90 | Intermediate C10-B | 88 | $C_{42}H_{37}BO_2S$ / 616.62 |

Modifications of Intermediate Cn-B

In addition to the Intermediate Cn-B, one person skilled in the art can adopt any one of foresaid Intermediates Cn to undergo a Miyaura borylation reaction to successfully synthesize other desired Intermediate Cn-B.

Synthesis of Novel Compounds

Each of the foresaid Intermediates Cn and Cn-B could be reacted with various reactants to synthesize various claimed novel compounds. The general synthesis pathway of the claimed novel compound was summarized in Scheme I. In the following Scheme I, "Reactant B" may be any one of Reactants B1 to B30 as listed in Table 4, and "Intermediate C" may be any one of the foresaid Intermediates Cn and Cn-B or the like. The compounds were each synthesized by the following steps.

Scheme I

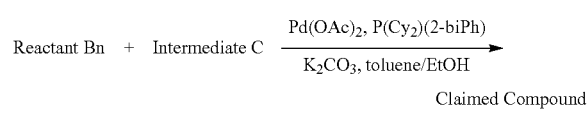

Reactant Bn + Intermediate C $\xrightarrow[K_2CO_3, \text{toluene/EtOH}]{Pd(OAc)_2, P(Cy_2)(2\text{-biPh})}$ Claimed Compound

TABLE 4 chemical structures and CAS No. of Reactants B1 to B30.

| Reactant No. | Reactant B1 | Reactant B2 |
|---|---|---|
| Chemical Structure | (HO)₂B—⌬—CN | pinacol boronate-pyridine |
| CAS No. | [126747-14-6] | [329214-79-1] |

| Reactant No. | Reactant B3 | Reactant B4 |
|---|---|---|
| Chemical Structure | bipyridine-Bpin | NC—⌬—pyridine—Br |
| CAS No. | [1260106-29-3] | [916653-46-8] |

TABLE 4-continued chemical structures and CAS No. of Reactants B1 to B30.

| Reactant No. | Reactant B5 | Reactant B6 |
|---|---|---|
| Chemical Structure | 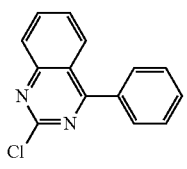 [SMILES: Clc1nc(-c2ccccc2)c2ccccc2n1] |  |
| CAS No. | [29874-83-7] | [29509-91-9] |
| Reactant No. | Reactant B7 | Reactant B8 |
| Chemical Structure | 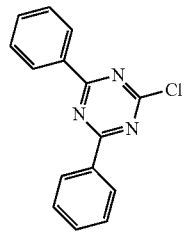 [SMILES: Clc1nc(-c2ccccc2)nc(-c2ccccc2)n1] | 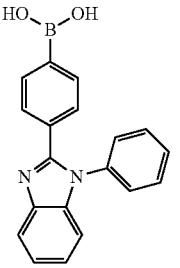 [SMILES: OB(O)c1ccc(-c2nc3ccccc3n2-c2ccccc2)cc1] |
| CAS No. | [3842-55-5] | [952514-79-3] |
| Reactant No. | Reactant B9 | Reactant B10 |
| Chemical Structure | 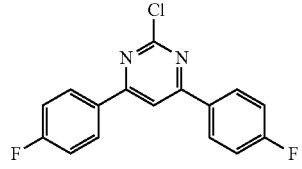 [SMILES: Fc1ccc(-c2cc(-c3ccc(F)cc3)nc(Cl)n2)cc1] | 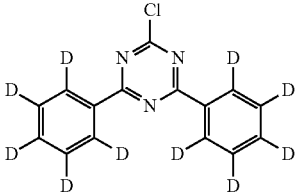 [SMILES: [2H]c1c([2H])c([2H])c(-c2nc(Cl)nc(-c3c([2H])c([2H])c([2H])c([2H])c3[2H])n2)c([2H])c1[2H]] |
| CAS No. | [1588407-97-9] | [1300115-09-6] |
| Reactant No. | Reactant B11 | Reactant B12 |
| Chemical Structure | 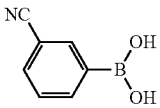 | 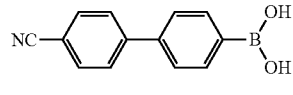 |
| CAS No. | [150255-96-2] | [406482-73-3] |
| Reactant No. | Reactant B13 | Reactant B14 |
| Chemical Structure | 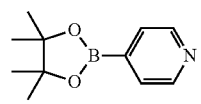 | 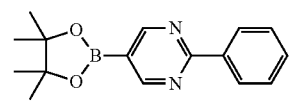 |
| CAS No. | [181219-01-2] | [1319255-85-0] |

TABLE 4-continued chemical structures and CAS No. of Reactants B1 to B30.

| Reactant No. | Reactant B15 | Reactant B16 |
|---|---|---|
| Chemical Structure | | |
| CAS No. | [6484-25-9] | [3114-52-1] |
| Reactant No. | Reactant B17 | Reactant B18 |
| Chemical Structure | | |
| CAS No. | [867044-33-5] | [7089-68-1] |
| Reactant No. | Reactant B19 | Reactant B20 |
| Chemical Structure | | |
| CAS No. | [1616231-57-2] | [1421599-34-9] |
| Reactant No. | Reactant B21 | Reactant B22 |
| Chemical Structure | | |
| CAS No. | [99682-89-0] | [170230-28-1] |

TABLE 4-continued chemical structures and CAS No. of Reactants B1 to B30.

| Reactant No. | Reactant B23 | Reactant B24 |
|---|---|---|
| Chemical Structure | (structure) | (structure) |

| Reactant No. | Reactant B25 | Reactant B26 |
|---|---|---|
| Chemical Structure | (structure) | (structure) |

| Reactant No. | Reactant B27 | Reactant B28 |
|---|---|---|
| Chemical Structure | (structure) | (structure) |

| Reactant No. | Reactant B29 | Reactant B30 |
|---|---|---|
| Chemical Structure | (structure) | (structure) |

A mixture of Intermediate C (1.0 eq), palladium(II) acetate (Pd(OAc)$_2$)(0.01 eq), P(Cy)$_2$(2-biphenyl) (0.04 eq), toluene/ethanol (0.5M, v/v=10/1), potassium carbonate solution (K$_2$CO$_3$) (3.0 M), and Reactant Bn (2.1 eq) was stirred at 100° C. for 12 h under nitrogen atmosphere. After the completion of the reaction, water and toluene were added to the reaction mass. Subsequently, the organic layer was recovered by solvent extraction operation and dried over sodium sulfate. The solvent was then removed from the organic layer under reduced pressure, and the resulting residue was purified by silica gel column chromatography. The obtained residue was recrystallized with toluene to obtain a white solid product as the claimed novel compound.

Figure 2:
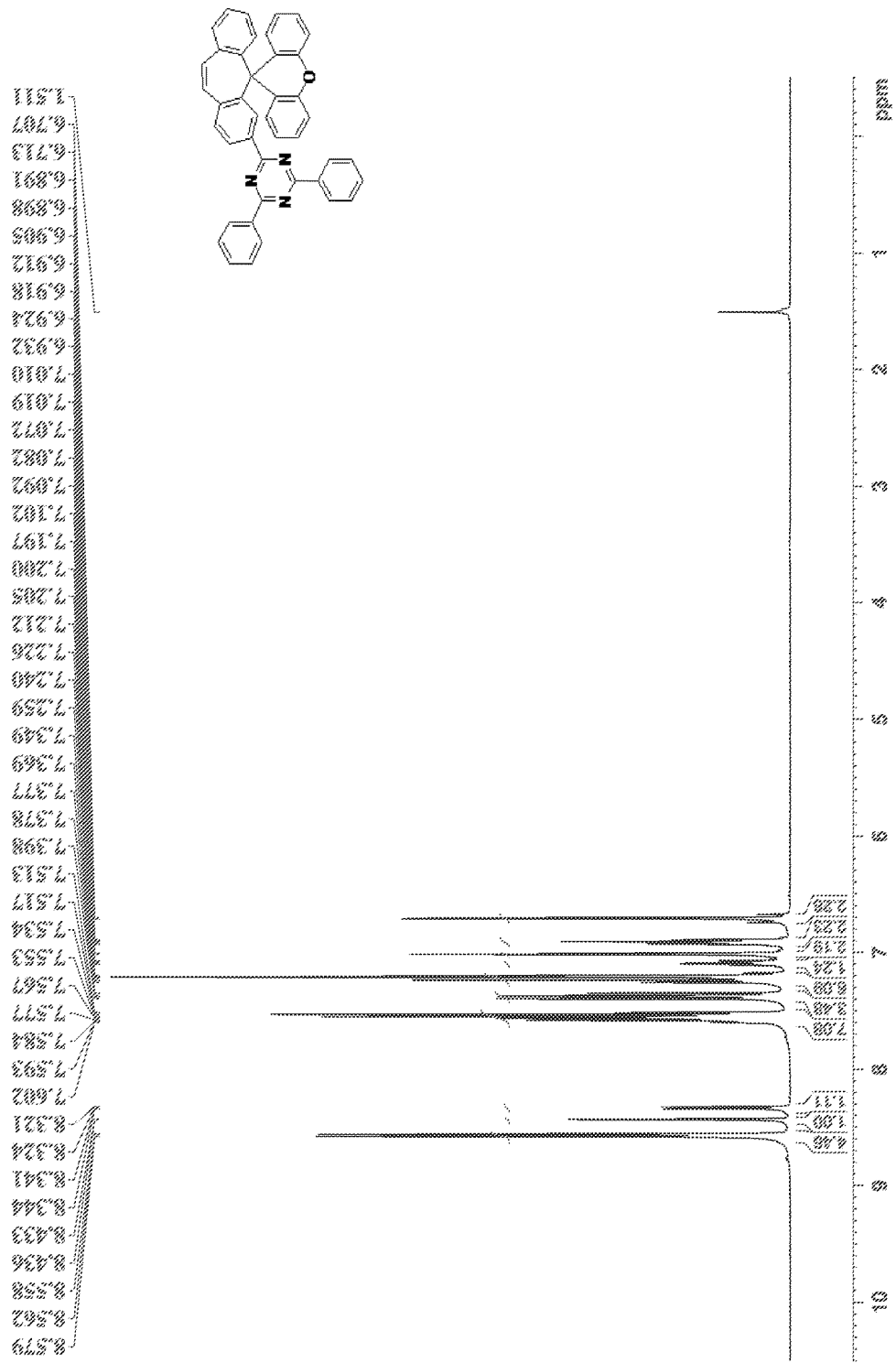
Figure 3:
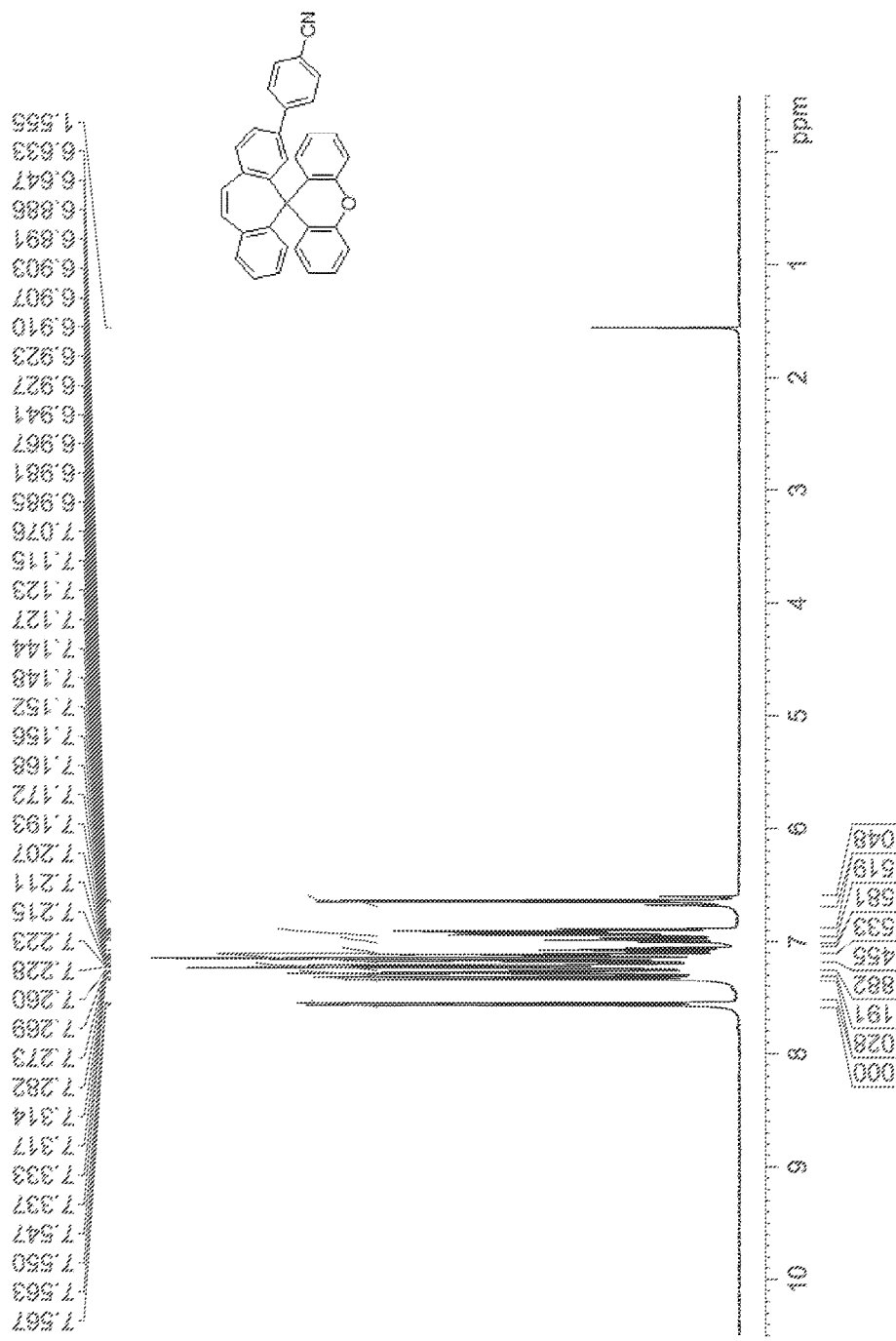
Figure 4:
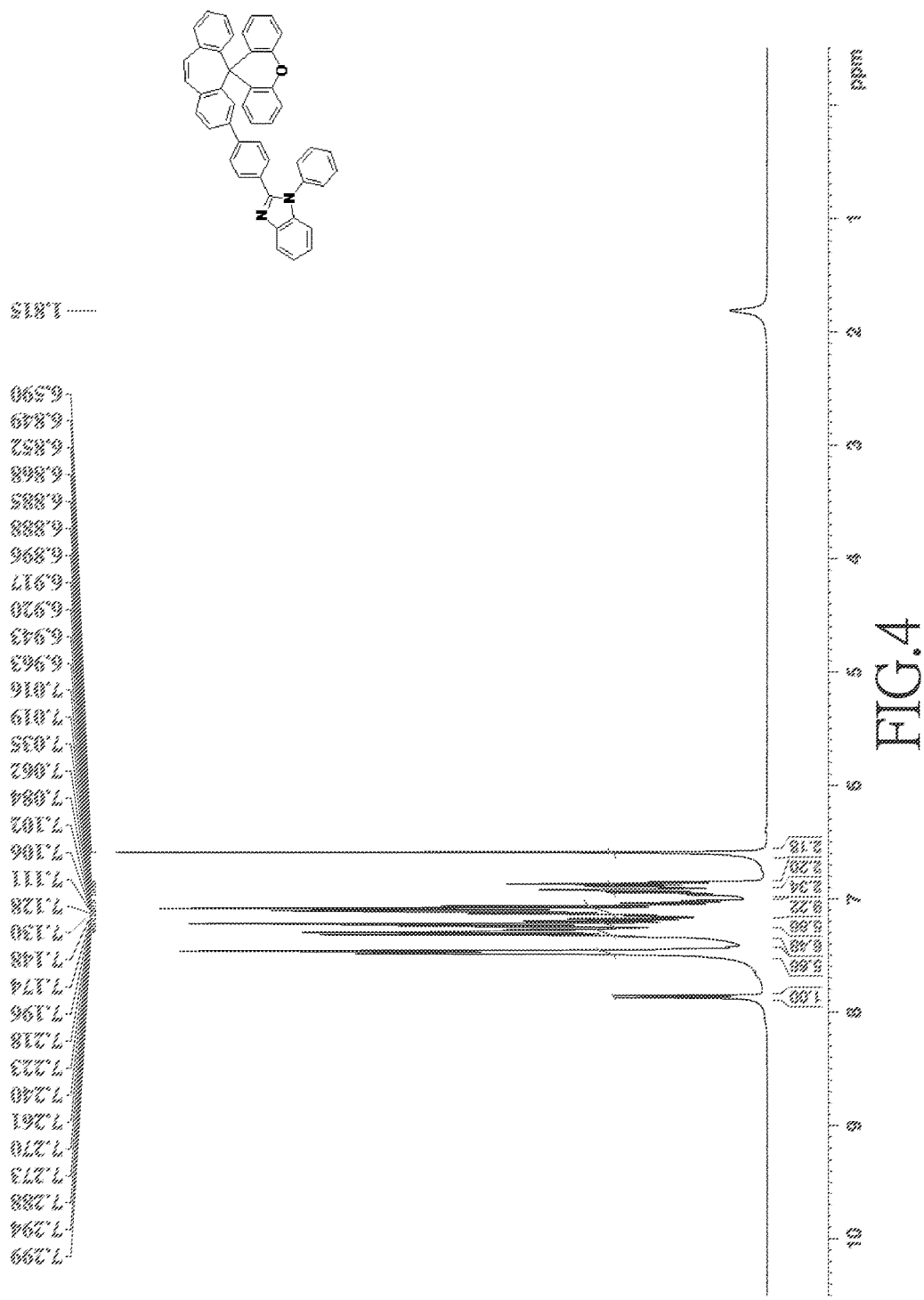
Figure 5:
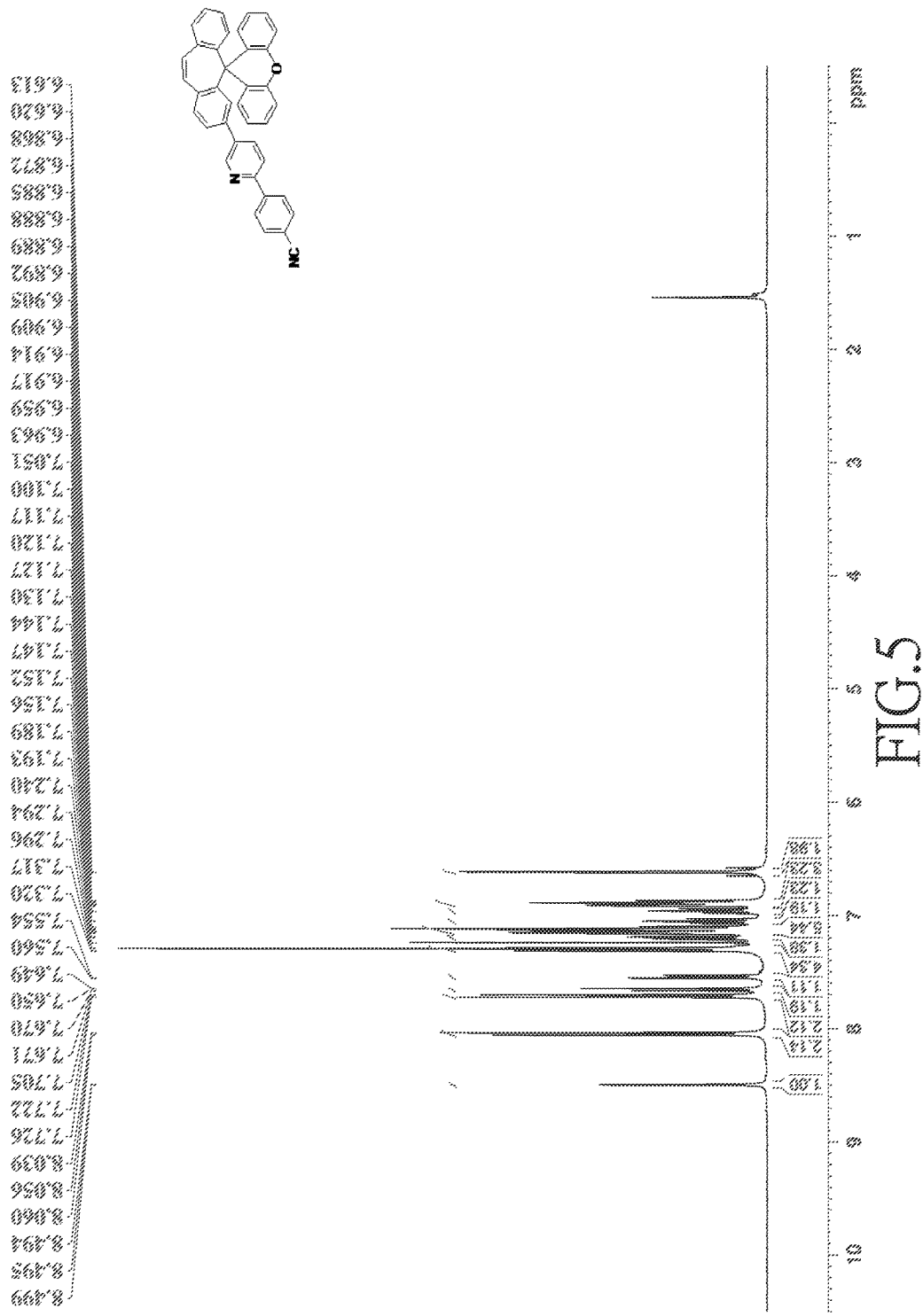
Figure 6:
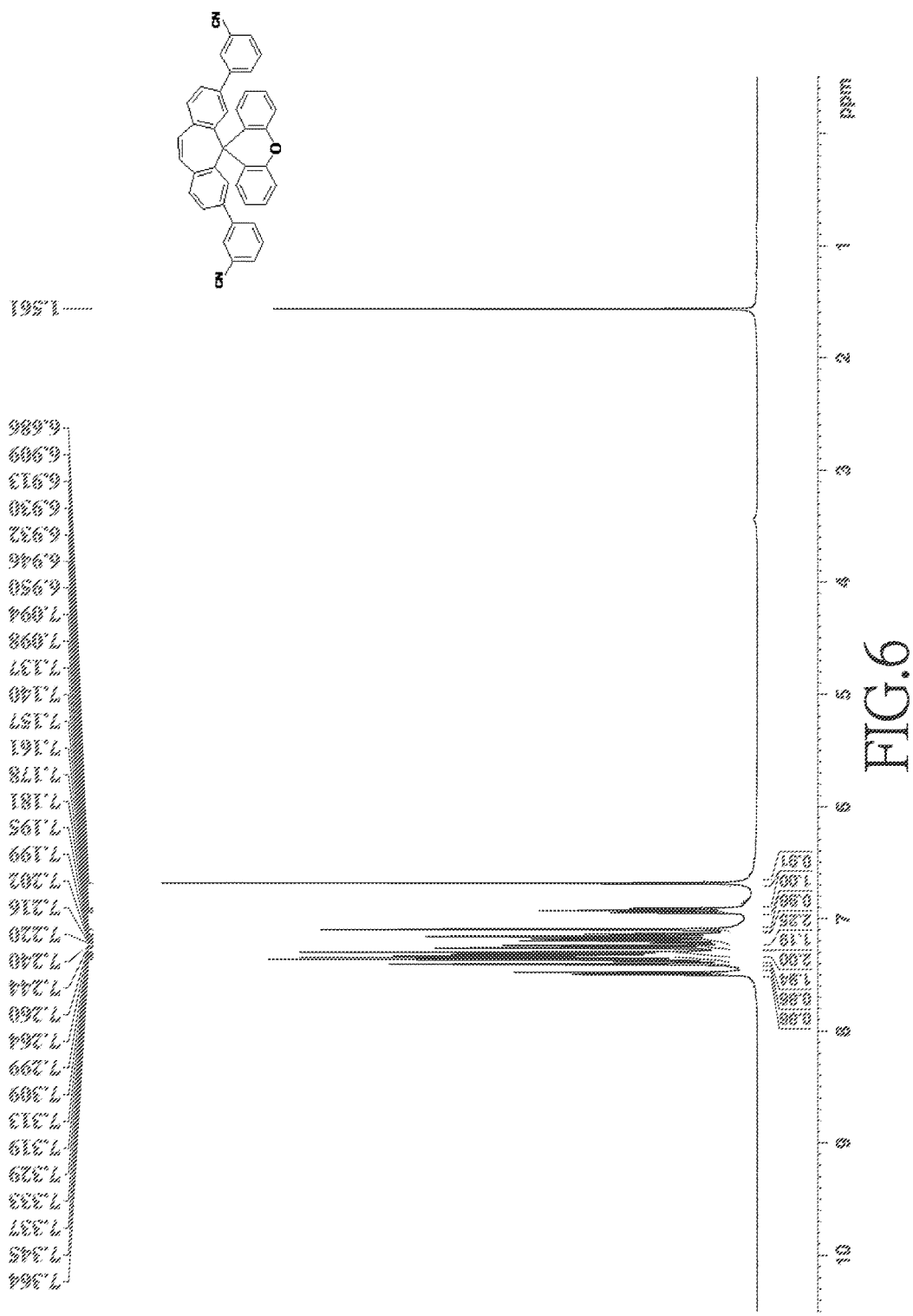
Figure 7:
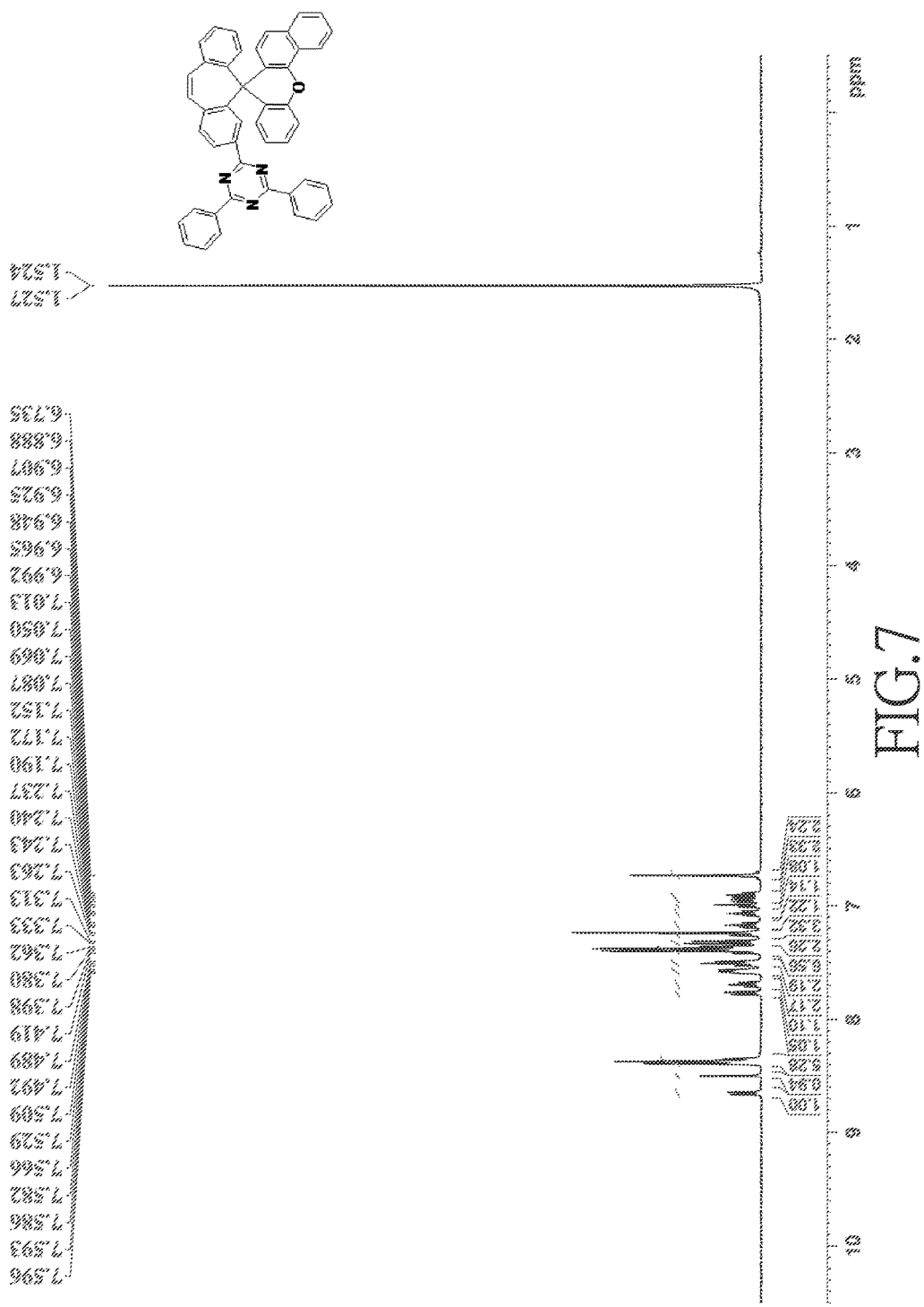
Figure 8:
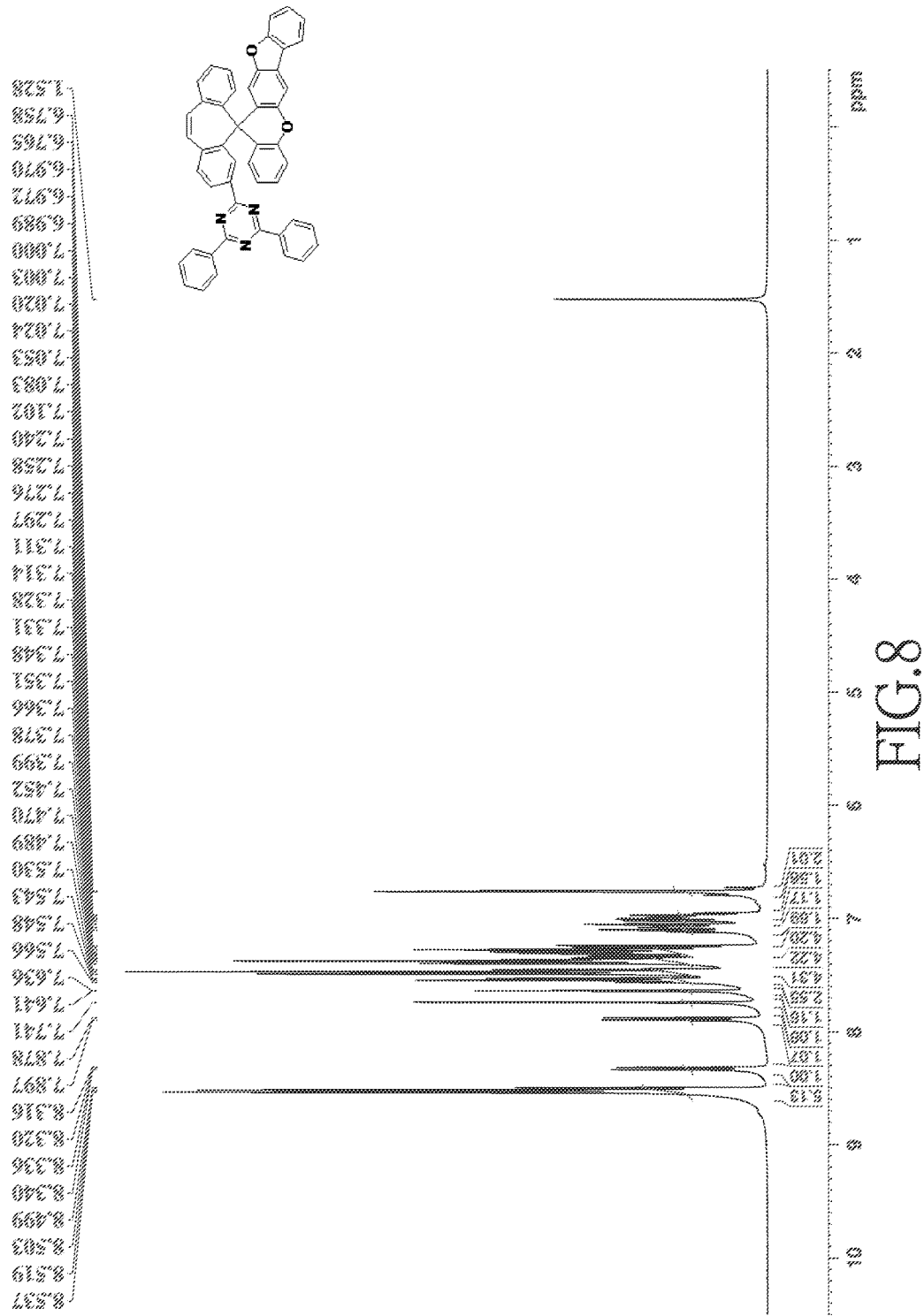
Figure 9:
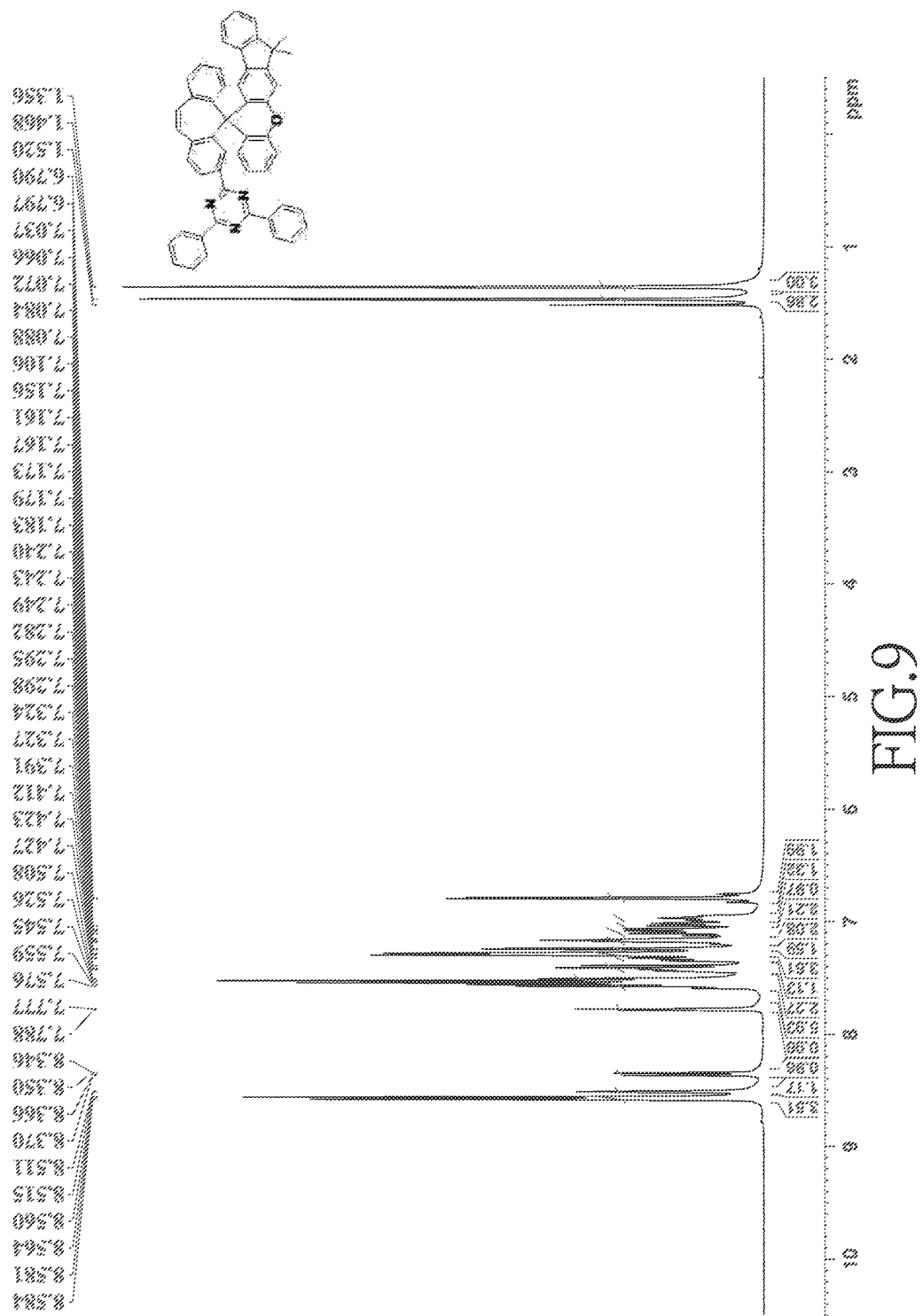
Figure 10:
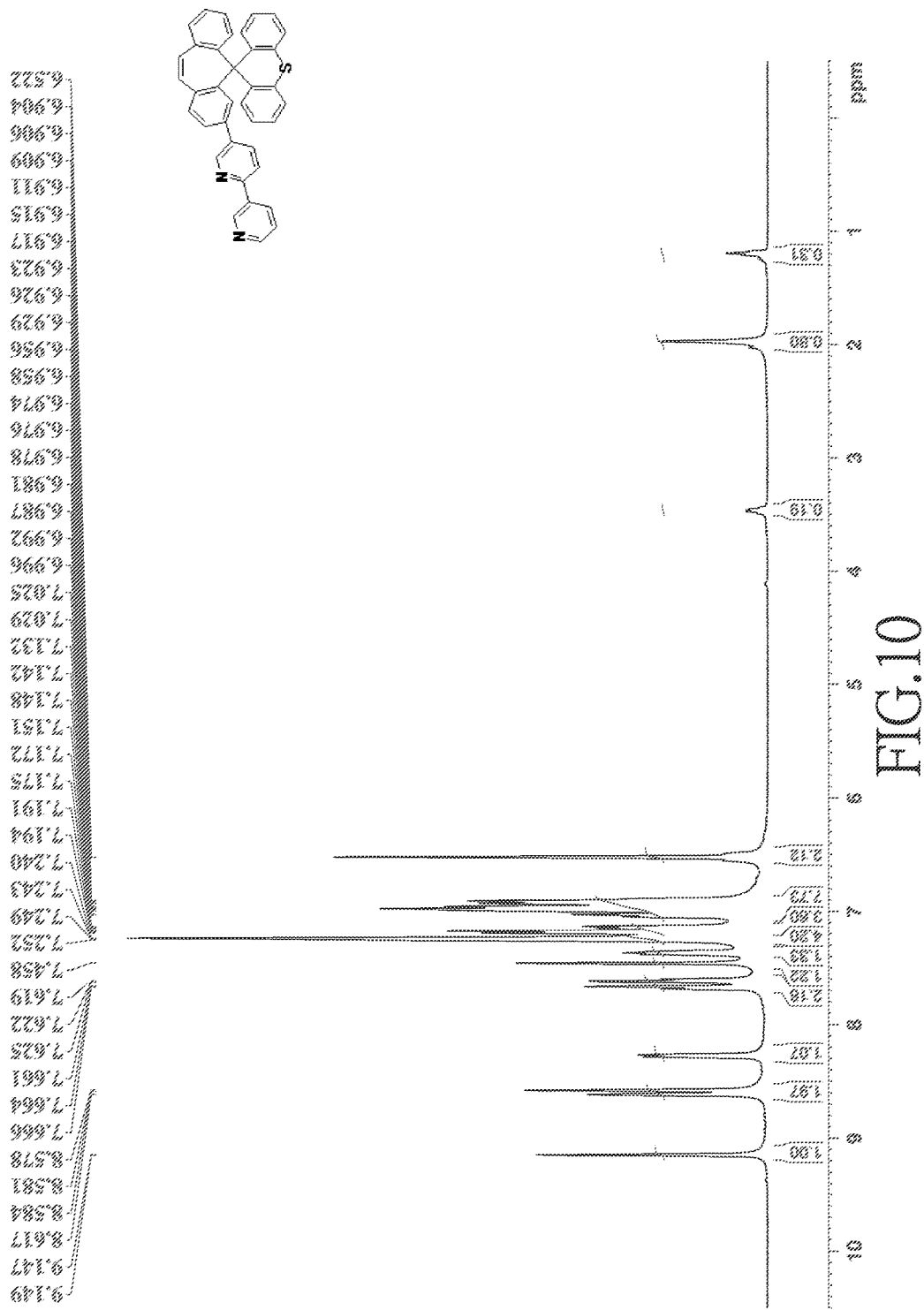
Figure 11:
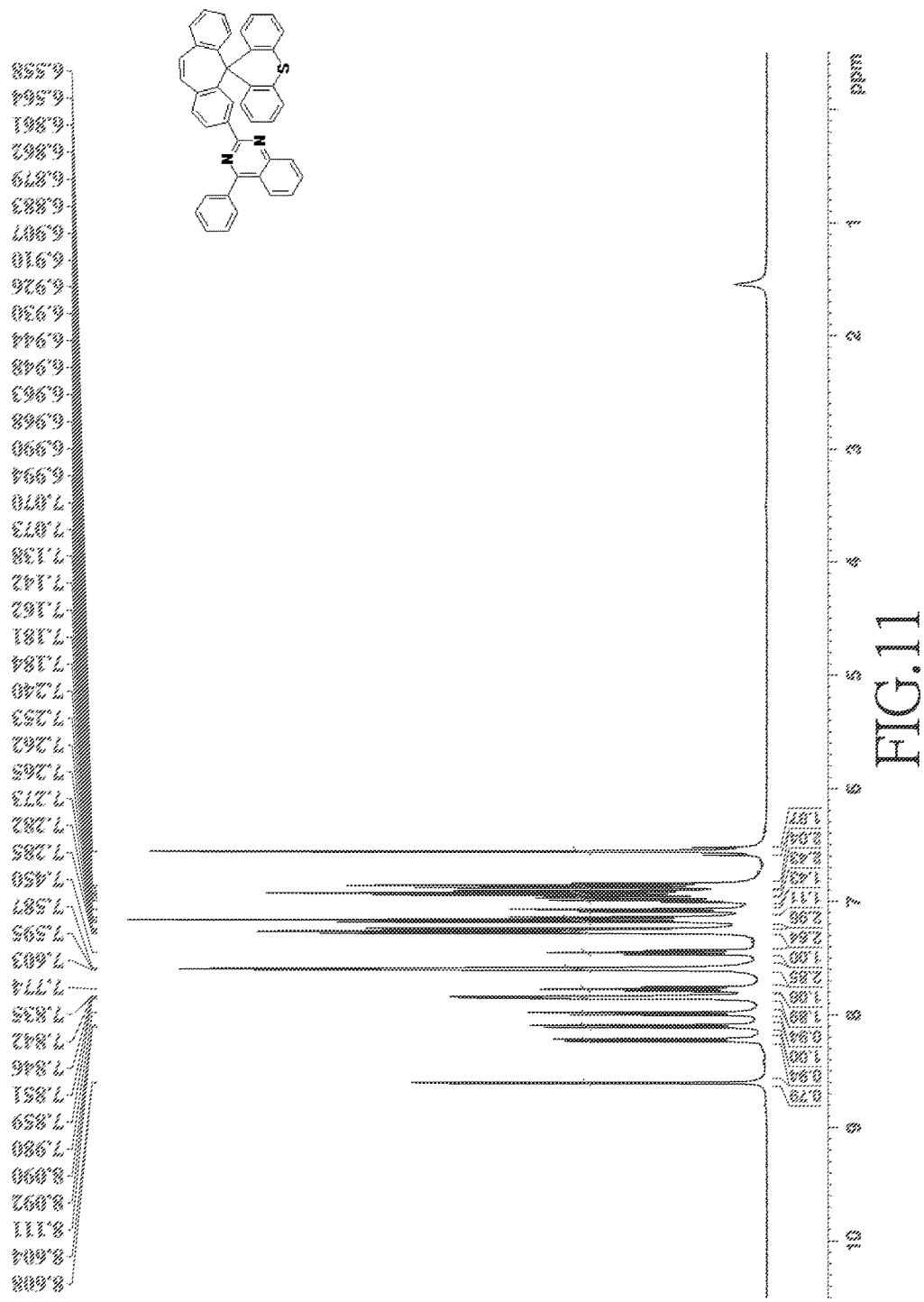
Figure 12:
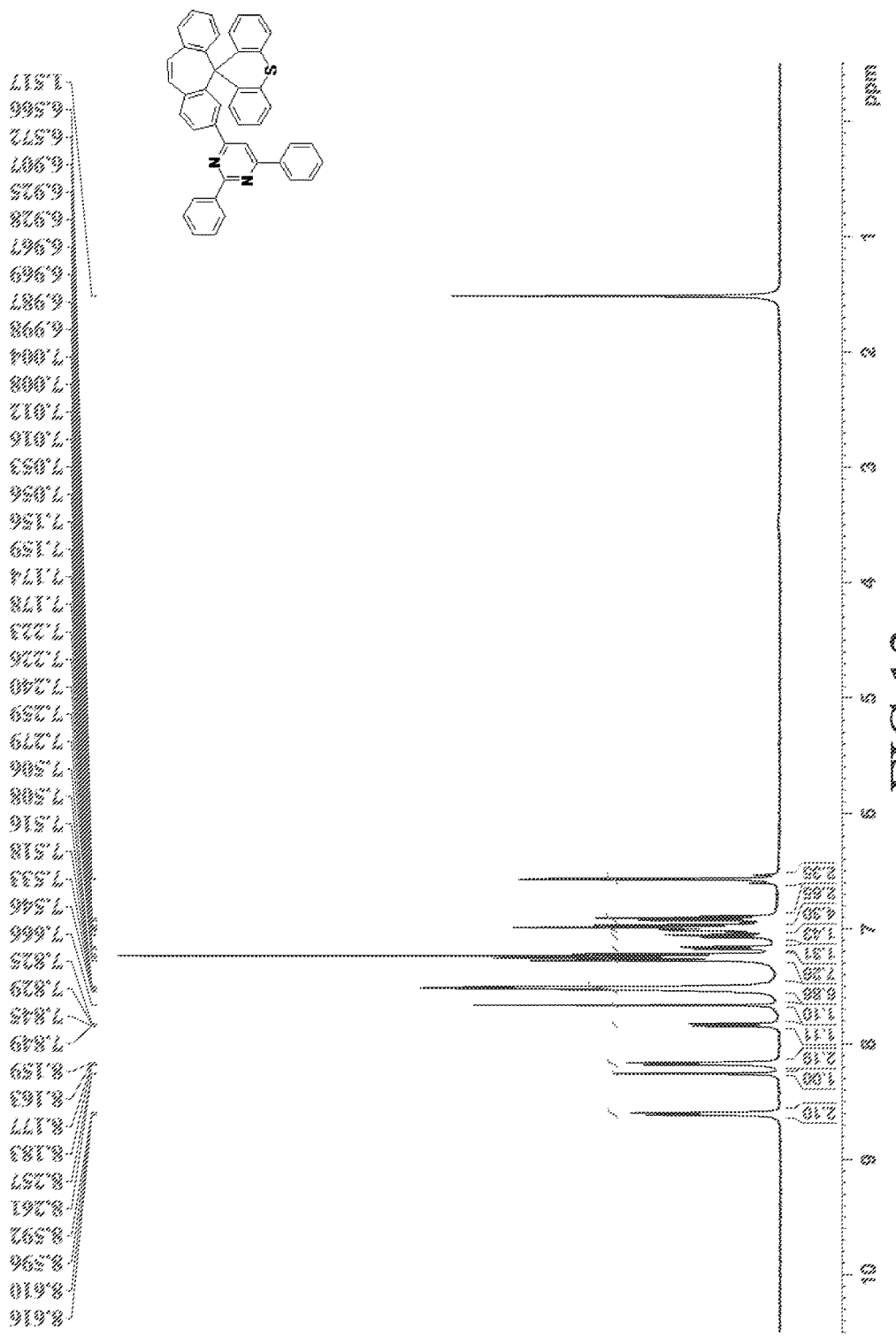
Figure 13:
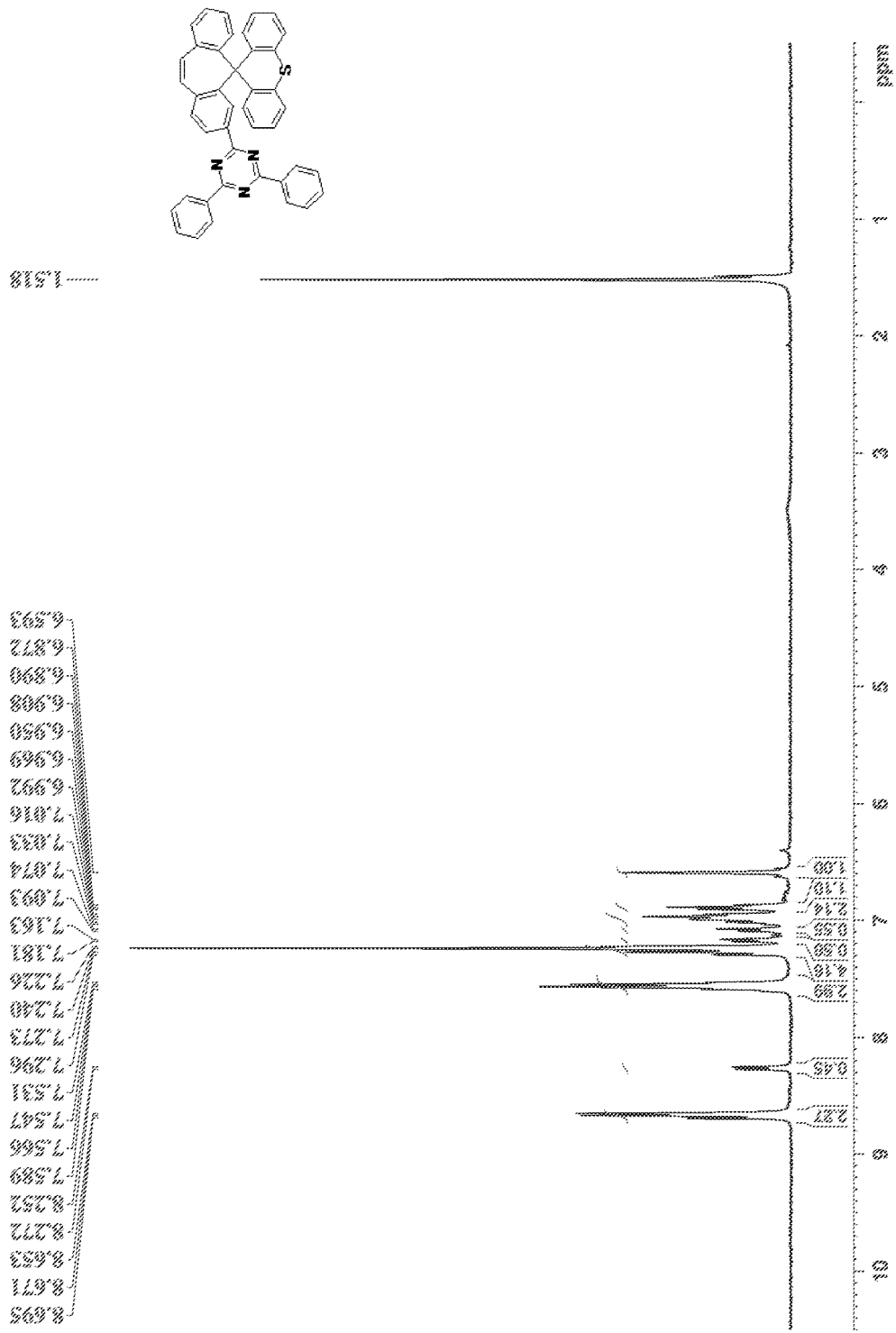
Figure 14:
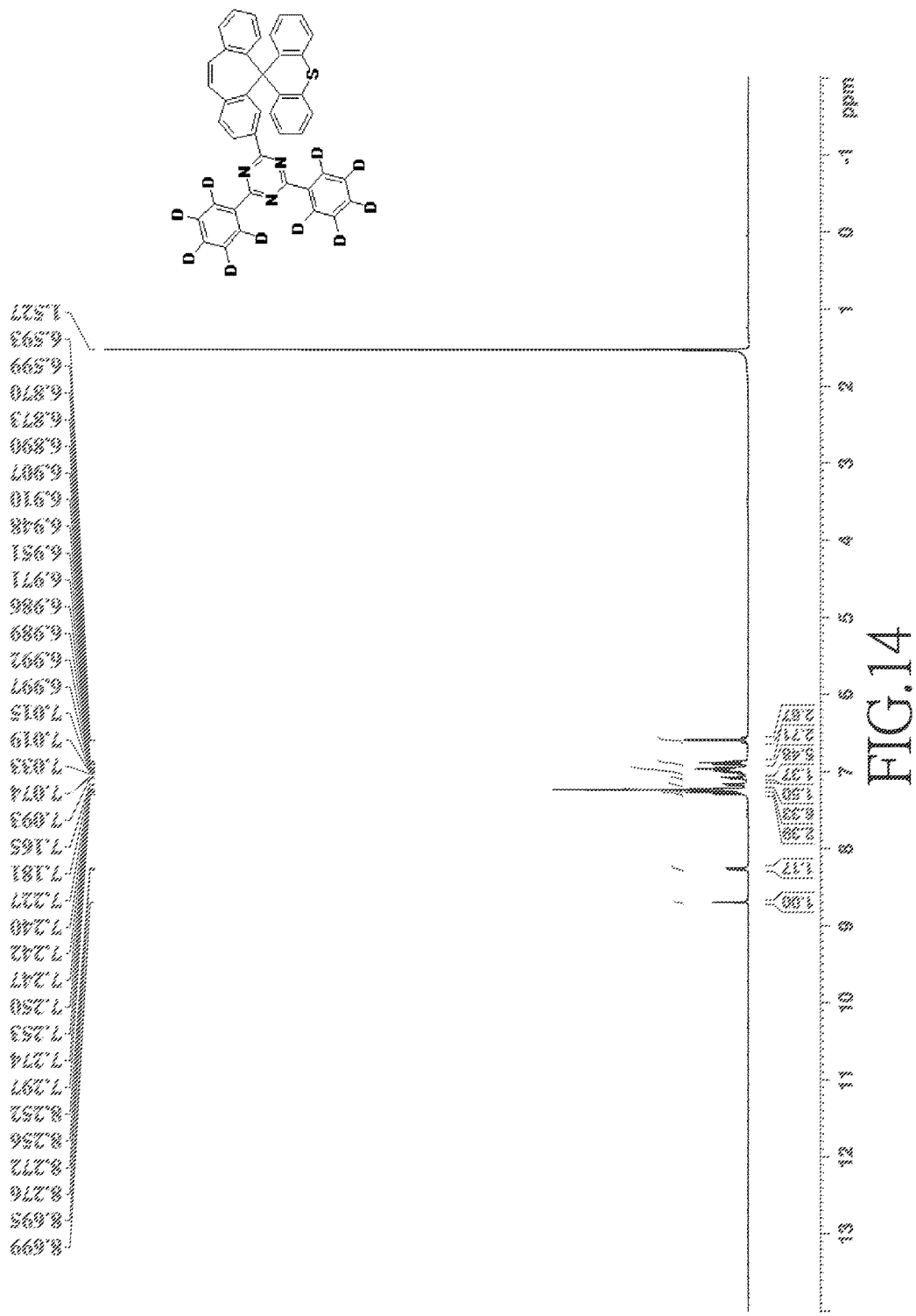
Figure 15:
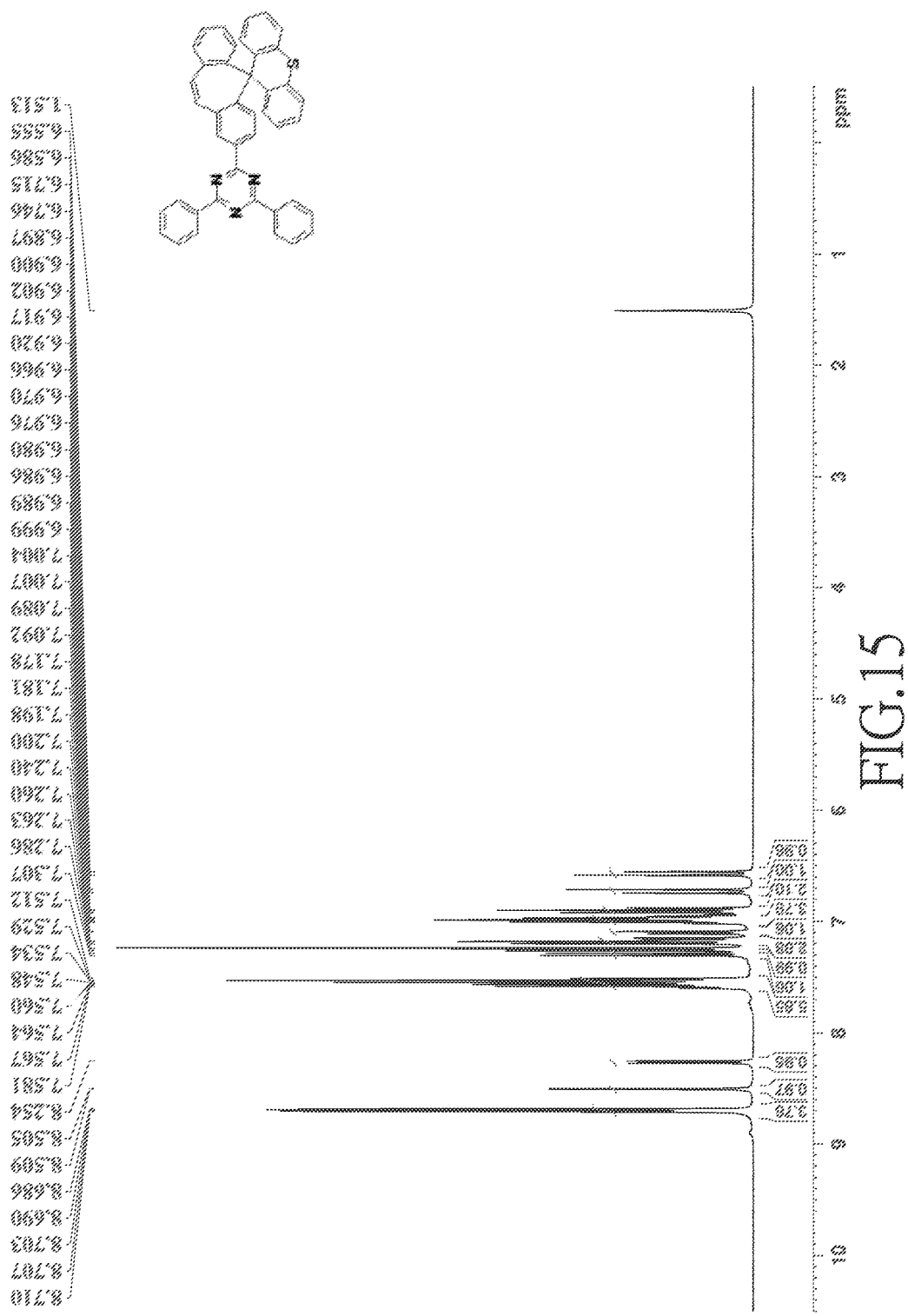
Figure 16:
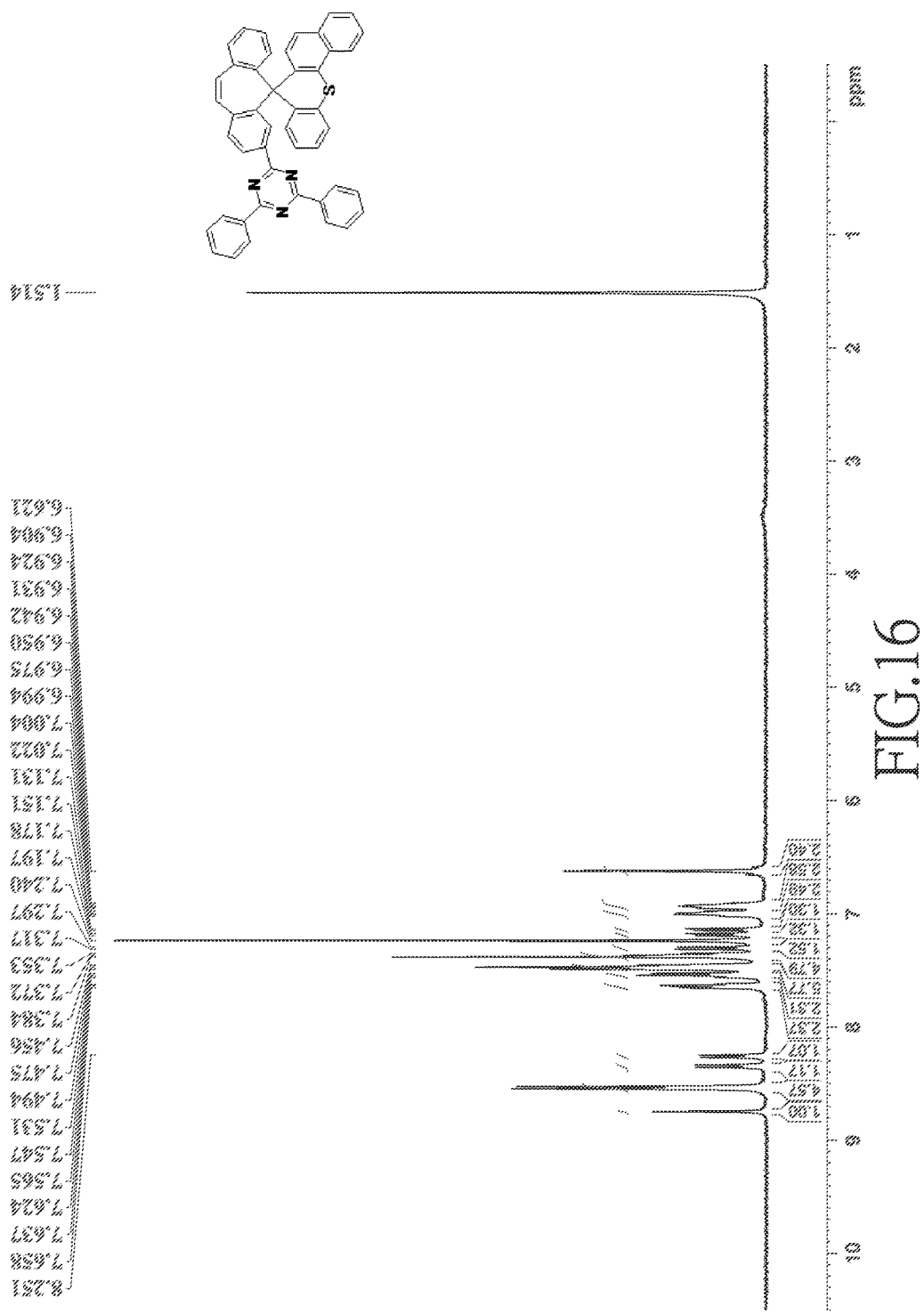
Figure 17:
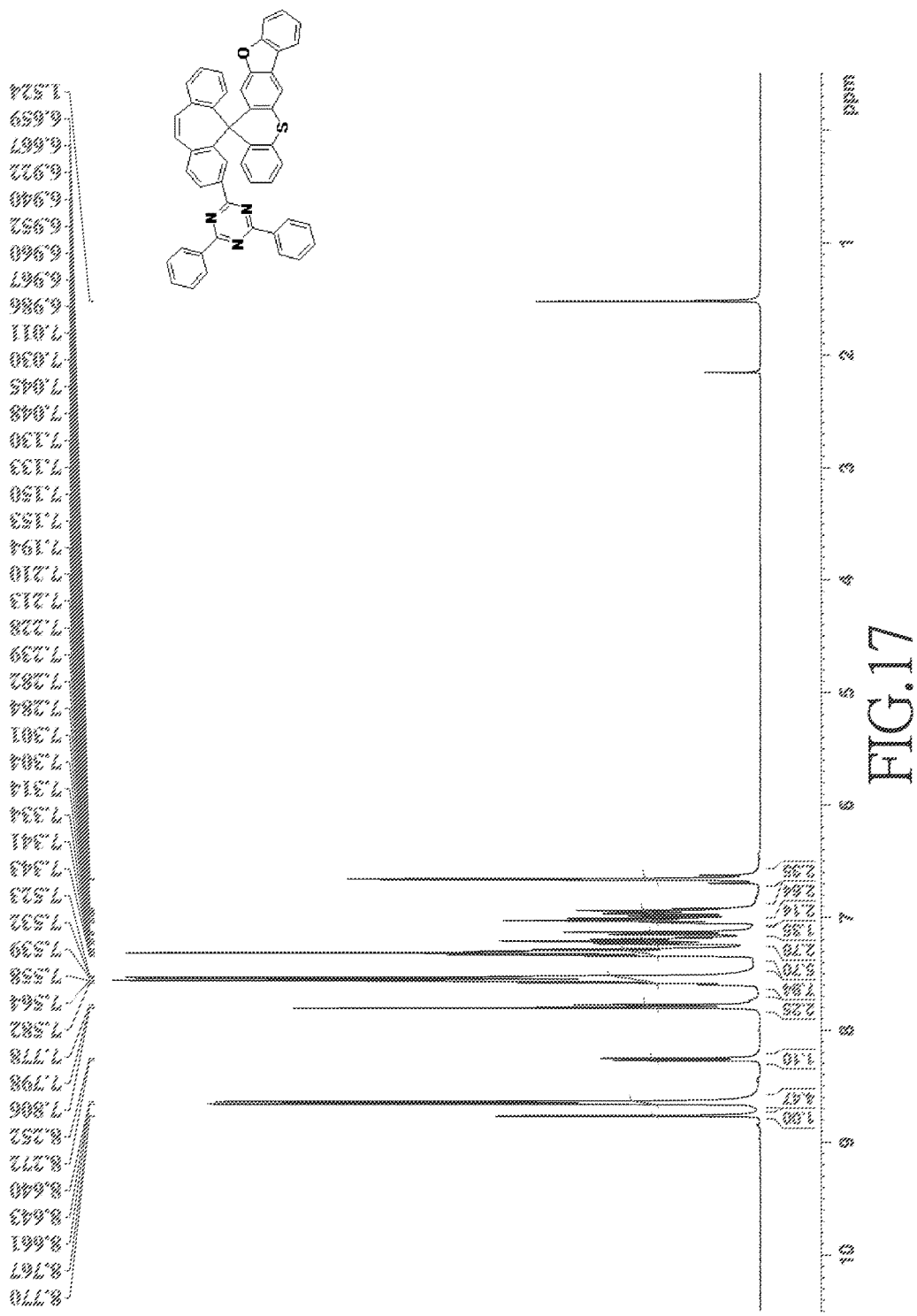

Reactant Bn and Intermediate C adopted to synthesize Compounds 1 to 17 were listed in Table 5. Compounds 1 to 17 were identified by H$^1$-NMR and FD-MS, and the chemical structure, yield, formula and mass of each of Compounds 1 to 17 were also listed in Table 5. According to FIGS. 2 to 18 and the results of FD-MS, the chemical structures of Compounds 1 to 17 were identified as follows.

TABLE 5 reactants and intermediates adopted to prepare Compounds 1 to 17 and their yields, formulae, and FD-MS data.

| Intermediate No. | Reactant No. | Chemical Structure of Claimed Compound | Yield (%) | Formula/ Mass (M+) |
|---|---|---|---|---|
| C1-B | B7 | Compound 1 | 85 | $C_{42}H_{27}N_3O$/ 589.68 |
| C1 | B1 | Compound 2 | 88 | $C_{34}H_{21}NO$/ 459.54 |
| C1 | B8 | Compound 3 | 80 | $C_{46}H_{30}N_2O$/ 626.74 |
| C1-B | B4 | Compound 4 | 73 | $C_{39}H_{24}N_2O$/ 536.62 |

TABLE 5-continued reactants and intermediates adopted to prepare Compounds 1 to 17 and their yields, formulae, and FD-MS data.

| Intermediate No. | Reactant No. | Chemical Structure of Claimed Compound | Yield (%) | Formula/ Mass (M+) |
|---|---|---|---|---|
| C2 | B11 | Compound 5 | 90 | $C_{41}H_{24}N_2O$ / 560.64 |
| C3-B | B7 | Compound 6 | 88 | $C_{46}H_{29}N_3O$ / 639.74 |
| C4-B | B7 | Compound 7 | 80 | $C_{48}H_{29}N_3O_2$ / 679.76 |
| C5-B | B7 | Compound 8 | 78 | $C_{51}H_{35}N_3O$ / 705.84 |

TABLE 5-continued reactants and intermediates adopted to prepare Compounds 1 to 17 and their yields, formulae, and FD-MS data.

| | | Claimed Compound | | |
|---|---|---|---|---|
| Intermediate No. | Reactant No. | Chemical Structure of Claimed Compound | Yield (%) | Formula/ Mass (M+) |
| C6 | B3 | Compound 9 | 76 | $C_{37}H_{24}N_2S$/ 528.66 |
| C6-B | B5 | Compound 10 | 92 | $C_{41}H_{26}N_2S$/ 578.72 |
| C6-B | B6 | Compound 11 | 90 | $C_{43}H_{28}N_2S$/ 604.76 |
| C6-B | B7 | Compound 12 | 91 | $C_{42}H_{27}N_3S$/ 605.75 |

TABLE 5-continued reactants and intermediates adopted to prepare Compounds 1 to 17 and their yields, formulae, and FD-MS data.

| Intermediate No. | Reactant No. | Chemical Structure of Claimed Compound | Yield (%) | Formula/ Mass (M+) |
|---|---|---|---|---|
| C6-B | B10 | Compound 13 | 70 | $C_{42}H_{17}D_{10}N_3S$ / 615.81 |
| C7-B | B7 | Compound 14 | 88 | $C_{42}H_{27}N_3S$ / 605.75 |
| C8-B | B7 | Compound 15 | 76 | $C_{46}H_{29}N_3S$ / 655.81 |

TABLE 5-continued reactants and intermediates adopted to prepare Compounds 1 to 17 and
their yields, formulae, and FD-MS data.

| | | Claimed Compound | | |
|---|---|---|---|---|
| Intermediate No. | Reactant No. | Chemical Structure of Claimed Compound | Yield (%) | Formula/ Mass (M+) |
| C9-B | B7 | Compound 16 | 80 | $C_{48}H_{29}N_3OS$/ 695.83 |
| C10-B | B7 | Compound 17 | 73 | $C_{51}H_{35}N_3S$/ 721.91 |

Modifications of Compounds 1 to 17

In addition to the Compounds 1 to 17, one person skilled in the art can react any Intermediate C, i.e., the foresaid Intermediate Cn or Cn-B, with any Reactant Bn through a reaction mechanism similar to Scheme I to synthesize other desired claimed novel compounds.

Preparation of OLED Devices

A glass substrate coated with ITO layer (abbreviated as in ITO substrate) in a thickness of 1500 Å was placed in distilled water containing a detergent dissolved therein, and was ultrasonically washed. The detergent was a product manufactured by Fischer Co., and the distilled water was distilled water filtered twice through a filter (Millipore Co.). After the ITO layer had been washed for 30 minutes, it was ultrasonically washed twice with distilled water for 10 minutes. After the completion of washing, the glass substrate was ultrasonically washed with isopropyl alcohol, acetone and methanol solvents and then dried, after which it was transported to a plasma cleaner. Then the substrate was cleaned with oxygen plasma for 5 minutes, and then transferred to a vacuum evaporator.

After that, various organic materials and metal materials were sequentially deposited on the ITO substrate to obtain the OLED device of Examples 1 to 35 and Comparative Examples 1 to 6. The vacuum degree during the deposition was maintained at $1\times10^{-6}$ to $3\times10^{-7}$ torr. Herein, the ITO substrate was deposited with a first hole injection layer (HIL-1), a second hole injection layer (HIL-2), a hole transporting layer(HTL), a blue/green/red emission layer (BEL/GEL/REL), an electron transporting layer (ETL), an electron injection layer (EIL), and a cathode (Cthd).

Herein, HI was a material for forming HIL-1 and HIL-2; HI-D was a material for forming HIL-1; HT was a material for forming HTL; novel compounds of the present invention and commercial ETs (BCP and TPBi) were materials for forming ETL; Liq was a material for forming ETL and EIL. RH/GH/BH was host material for forming REL/GEL/BEL, and RD/GD/BD was dopant for forming REL/GEL/BEL. The main difference of the OLEDs between the Examples and Comparative Examples was that the ETL of the OLED in the following comparative examples was made of BCP or TPBi but the ETL of the OLED in the following examples was made of the novel compounds of the present invention as listed in Table 5. The detailed chemical structures of foresaid commercial materials were listed in Table 6.

TABLE 6
chemical structures of commercial materials for OLED devices.
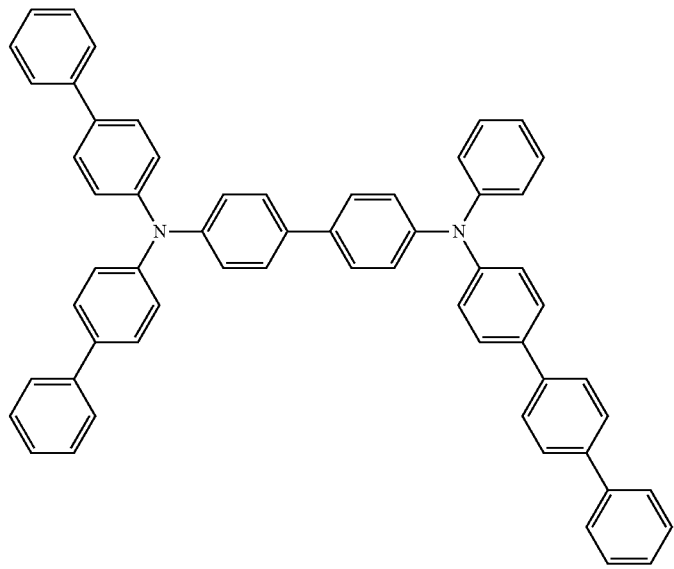 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]
HI
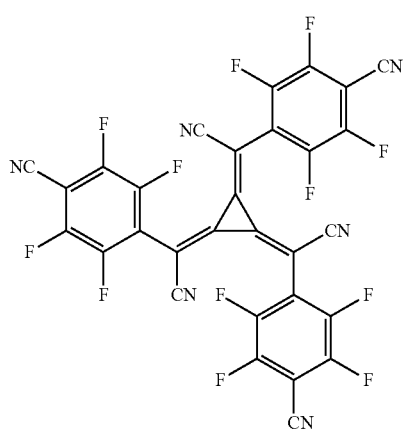 [SMILES: N#CC(=C1C(=C(C#N)c2c(F)c(F)c(C#N)c(F)c2F)C1=C(C#N)c1c(F)c(F)c(C#N)c(F)c1F)c1c(F)c(F)c(C#N)c(F)c1F]
HI-D
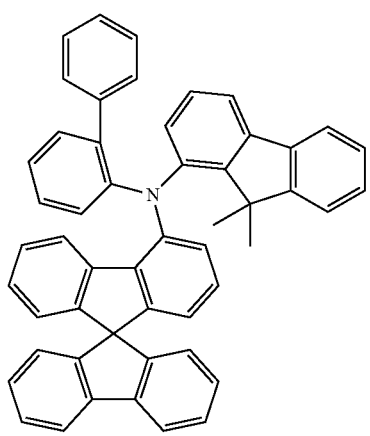 [SMILES: CC1(C)c2ccccc2-c2cccc(N(c3ccccc3-c3ccccc3)c3cccc4c3-c3ccccc3C43c4ccccc4-c4ccccc43)c21]
HT TABLE 6-continued
chemical structures of commercial materials for OLED devices.
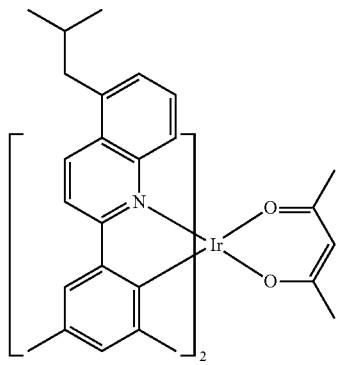
RD
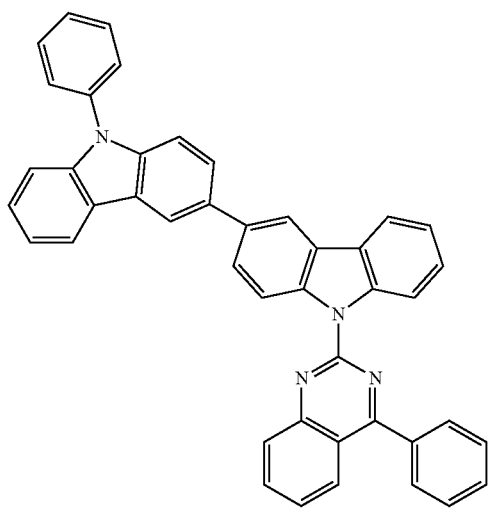 [SMILES: c1ccc(-c2nc(-n3c4ccccc4c4cc(-c5ccc6c(c5)c5ccccc5n6-c5ccccc5)ccc43)nc3ccccc23)cc1]
RH
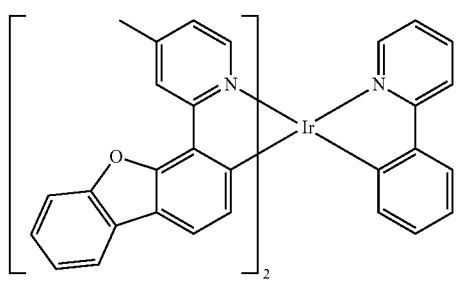
GD TABLE 6-continued
chemical structures of commercial materials for OLED devices.
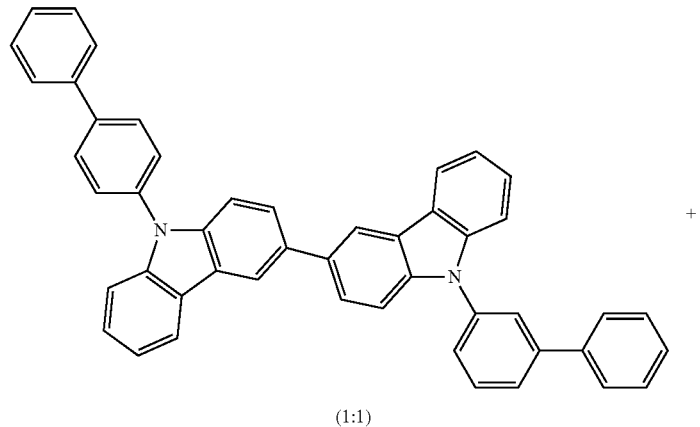 [SMILES: c1ccc(-c2ccc(-n3c4ccccc4c4cc(-c5ccc6c(c5)c5ccccc5n6-c5cccc(-c6ccccc6)c5)ccc43)cc2)cc1]
(1:1)
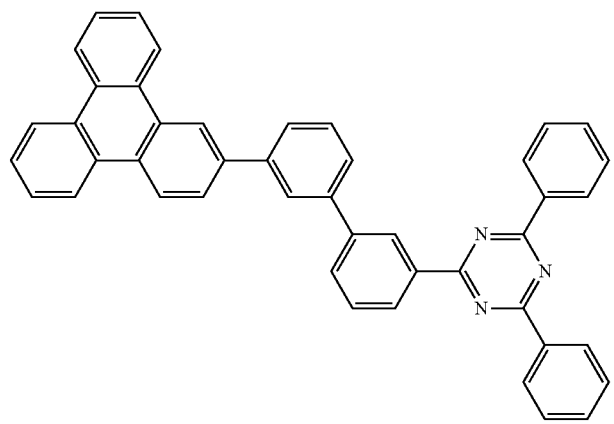 [SMILES: c1ccc(-c2nc(-c3ccccc3)nc(-c3cccc(-c4cccc(-c5ccc6c7ccccc7c7ccccc7c6c5)c4)c3)n2)cc1]
GH
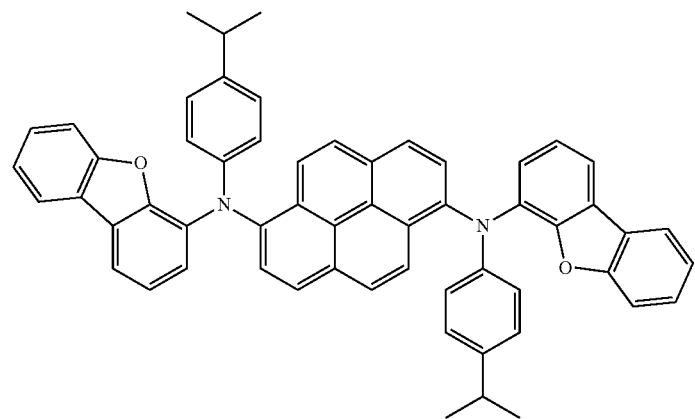 [SMILES: CC(C)c1ccc(N(c2ccc3ccc4c(N(c5ccc(C(C)C)cc5)c5cccc6c5oc5ccccc56)ccc5ccc2c3c54)c2cccc3c2oc2ccccc23)cc1]
BD TABLE 6-continued
chemical structures of commercial materials for OLED devices.
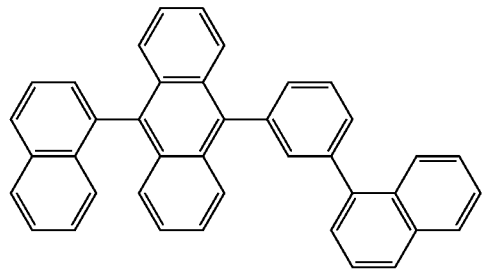 [SMILES: c1cc(-c2cccc3ccccc23)cc(-c2c3ccccc3c(-c3cccc4ccccc34)c3ccccc23)c1]
BH
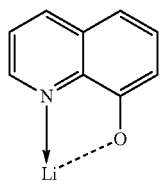
Liq
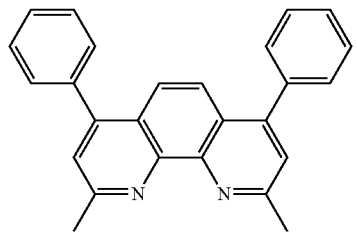 [SMILES: Cc1cc(-c2ccccc2)c2ccc3c(-c4ccccc4)cc(C)nc3c2n1]
BCP
(commercial ET)
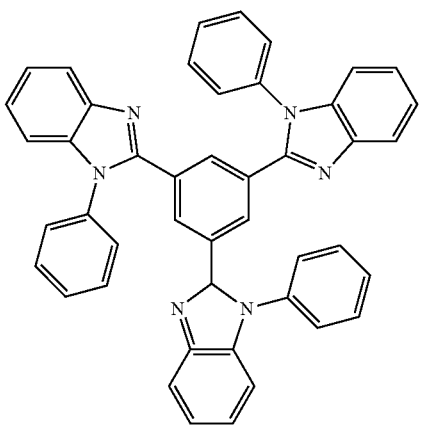
TPBi
(commercial ET)

Preparation of Red OLED Devices

To prepare the red OLED device, multiple organic layers were respectively deposited on the ITO substrate according to the sequence as listed in Table 7, and the materials and the thicknesses of the organic layers in red OLED devices were also listed in Table 7.

TABLE 7 coating sequence, materials and thickness of the organic layers in red OLED device.

| Coating Sequence | Layer | Material | Thickness |
|---|---|---|---|
| 1 | HIL-1 | HI doped with 3.0 wt % of HI-D | 100 Å |
| 2 | HIL-2 | HI | 2200 Å |
| 3 | HTL | HT | 100 Å |
| 4 | REL | RH doped with 3.5 wt % of RD | 300 Å |
| 5 | ETL | Commercial ET/novel compounds doped with 35.0 wt % of Liq | 350 Å |
| 6 | EIL | Liq | 15 Å |
| 7 | Cthd | Al | 1500 Å |

Preparation of Green OLED Devices

To prepare the green OLED device, multiple organic layers were respectively deposited on the ITO substrate according to the sequence as listed in Table 8, and the materials and the thicknesses of the organic layers in green OLED devices were also listed in Table 8.

TABLE 8 coating sequence, materials and thickness of the layers in green OLED device.

| Coating Sequence | Layer | Material | Thickness |
|---|---|---|---|
| 1 | HIL-1 | HI doped with 3.0 wt % of HI-D | 100 Å |
| 2 | HIL-2 | HI | 1400 Å |
| 3 | HTL | HT | 100 Å |
| 4 | GEL | GH doped with 10.0 wt % of GD | 400 Å |
| 5 | ETL | Commercial ET/novel compounds doped with 35.0 wt % of Liq | 350 Å |
| 6 | EIL | Liq | 15 Å |
| 7 | Cthd | Al | 1500 Å |

Preparation of Blue OLED Devices

To prepare the blue OLED device, multiple organic layers were respectively deposited on the ITO substrate according to the sequence as listed in Table 9, and the materials and the thicknesses of the organic layers in blue OLED devices were also listed in Table 9.

TABLE 9 coating sequence, materials and thickness of the layers in blue OLED device.

| Coating Sequence | Layer | Material | Thickness |
|---|---|---|---|
| 1 | HIL-1 | HI doped with 3.0 wt % of HI-D | 100 Å |
| 2 | HIL-2 | HI | 850 Å |
| 3 | HTL | HT | 100 Å |
| 4 | BEL | BH doped with 3.5 wt % of BD | 250 Å |
| 5 | ETL | Commercial ET/novel compounds doped with 35.0 wt % of Liq | 350 Å |
| 6 | EIL | Liq | 15 Å |
| 7 | Cthd | Al | 1500 Å |

Performance of OLED Device

To evaluate the performance of OLED devices, red, green, and blue OLED devices were measured by PR650 as photometer and Keithley 2400 as power supply. Color coordinates (x,y) were determined according to the CIE chromaticity scale (Commission Internationale de L'Eclairage, 1931). The results were shown in Table 10. For the blue and red OLED devices, the data were collected at 1000 nits. For the green OLED devices, the data were collected at 3000 nits.

The materials of ETL, color and data of CIE, driving voltage, current efficiency, and external quantum efficiency of Examples 1 to 35 (E1 to E35) and Comparative Example 1 to 6 (C1 to C6) were listed in Table 10.

TABLE 10 materials of ETL, colors, CIEs, voltages, current efficiencies, and external quantum efficiency of OLED devices of Examples 1 to 35 and Comparative Examples 1 to 6.

| Example No. | Material of ETL | CIE(x, y) | Voltage (V) | Current Efficiency (cd/A) | External Quantum Efficiency (%) |
|---|---|---|---|---|---|
| E1 | Compound 2 | B(0.135, 0.153) | 4.08 | 10.2 | 6.2 |
| E2 | Compound 1 | B(0.129, 0.155) | 4.43 | 7.98 | 5.62 |
| E3 | Compound 3 | B(0.129, 0.157) | 4.11 | 9.3 | 6.42 |
| E4 | Compound 4 | B(0.130, 0.144) | 4.49 | 7.01 | 4.92 |
| E5 | Compound 5 | B(0.129, 0.156) | 3.97 | 9.32 | 6.58 |
| E6 | Compound 6 | B(0.130, 0.149) | 4.49 | 7.58 | 5.25 |
| E7 | Compound 7 | B(0.130, 0.150) | 4.56 | 7.65 | 5.32 |
| E8 | Compound 8 | B(0.103, 0.152) | 4.02 | 8.49 | 5.38 |
| E9 | Compound 9 | B(0.129, 0.151) | 3.71 | 10.3 | 6.19 |
| E10 | Compound 10 | B(0.129, 0.17) | 4.03 | 10.4 | 7.11 |
| E11 | Compound 12 | B(0.129, 0.164) | 4.27 | 8.33 | 5.62 |
| E12 | Compound 13 | B(0.129, 0.155) | 4.35 | 7.91 | 5.57 |
| E13 | Compound 14 | B(0.129, 0.158) | 3.7 | 9.7 | 6.34 |
| E14 | Compound 15 | B(0.129, 0.163) | 4.44 | 7.59 | 5.32 |
| C1 | BCP | B(0.129, 0.154) | 5.66 | 7.49 | 4.62 |
| C2 | TPBi | B(0.129, 0.154) | 5.65 | 7.33 | 4.61 |
| E15 | Compound 2 | G(0.329, 0.635) | 3.9 | 76.2 | 17.62 |
| E16 | Compound 1 | G(0.315, 0.639) | 3.8 | 78.2 | 17.52 |
| E17 | Compound 3 | G(0.316, 0.638) | 3.83 | 79.6 | 17.66 |
| E18 | Compound 5 | G(0.316, 0.638) | 3.92 | 77.7 | 17.85 |
| E19 | Compound 6 | G(0.316, 0.637) | 3.99 | 76.8 | 17.6 |
| E20 | Compound 7 | G(0.315, 0.638) | 4.17 | 74.4 | 16.21 |
| E21 | Compound 8 | G(0.329, 0.629) | 4.15 | 79.6 | 17.98 |
| E22 | Compound 9 | G(0.322, 0.634) | 3.72 | 79.7 | 18.06 |
| E23 | Compound 10 | G(0.312, 0.639) | 3.7 | 78.1 | 17.47 |
| E24 | Compound 11 | G(0.337, 0.624) | 4.24 | 75.8 | 18.25 |
| E25 | Compound 12 | G(0.325, 0.632) | 3.95 | 78.9 | 18.19 |
| E26 | Compound 13 | G(0.321, 0.635) | 3.84 | 75.3 | 17.12 |
| E27 | Compound 14 | G(0.313, 0.638) | 4.11 | 78.5 | 17.9 |
| E28 | Compound 15 | G(0.319, 0.636) | 4.01 | 77.8 | 17.62 |
| C3 | BCP | G(0.308, 0.643) | 5.42 | 72.4 | 16.1 |
| C4 | TPBi | G(0.306, 0.643) | 6.34 | 68.9 | 14.86 |
| E29 | Compound 2 | R(0.660, 0.337) | 3.95 | 28.5 | 21.53 |
| E30 | Compound 3 | R(0.659, 0.339) | 4.25 | 27.9 | 21.85 |
| E31 | Compound 5 | R(0.658, 0.34) | 3.91 | 28.9 | 21.67 |
| E32 | Compound 9 | R(0.657, 0.34) | 4.11 | 27.9 | 21.766 |
| E33 | Compound 10 | R(0.659, 0.338) | 3.94 | 28.2 | 22.18 |
| E34 | Compound 12 | R(0.657, 0.341) | 3.92 | 29.6 | 20.71 |
| E35 | Compound 14 | R(0.66, 0.338) | 3.96 | 28.6 | 22.45 |
| C5 | BCP | R(0.659, 0.339) | 5.4 | 27.7 | 20.23 |
| C6 | TBPi | R(0.659, 0.339) | 5.81 | 27.1 | 19.65 |

Based on the results, in comparison with the commercial electron transport material, adopting Compounds 1 to 15 as the electron transport material can reduce the driving voltage and improve the current efficiency of the red, green, or blue OLEDs. It demonstrates that the novel compound of the present invention is suitable as an electron transport material for any color OLEDs, and allows the OLEDs using the same to have low driving voltage and improved current efficiency.

Even though numerous characteristics and advantages of the present invention have been set forth in the foregoing description, together with details of the structure and fea-

145 tures of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A compound represented by the following Formula (I):

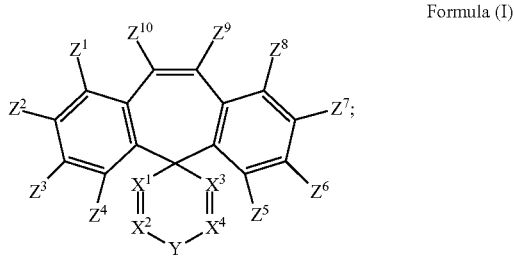

Formula (I)

wherein $X^1$ and $X^2$ are each independently $C(R^a)$, the two ($R^a$)s are the same or different, and the two ($R^a$)s are joined together to form a first aryl ring;
wherein $X^3$ and $X^4$ are each independently $C(R^b)$, the two ($R^b$)s are the same or different, and the two ($R^b$)s are joined together to form a second aryl ring or a heteroaryl ring;
wherein Y is an oxygen atom or a sulfur atom;
wherein at least one of $Z^1$ to $Z^8$ is selected from the group consisting of: an alkyl group having 1 to 40 carbon atoms and substituted with at least one functional group, an alkenyl group having 2 to 40 carbon atoms and substituted with at least one functional group, an alkynyl group having 2 to 40 carbon atoms and substituted with at least one functional group, a cycloalkyl group having 3 to 60 ring carbon atoms and substituted with at least one functional group, a heterocycloalkyl group having 3 to 60 ring carbon atoms and substituted with at least one functional group, an aryl group having 6 to 60 ring carbon atoms and substituted with at least one functional group, a heteroaryl group having 3 to 60 ring carbon atoms containing at least one nitrogen atom, an alkoxy group having 1 to 40 carbon atoms and substituted with at least one functional group, an aryloxy group having 6 to 60 ring carbon atoms and substituted with at least one functional group, an alkylsilyl group having 1 to 40 carbon atoms and substituted with at least one functional group, an arylsilyl group having 6 to 60 ring carbon atoms and substituted with at least one functional group, an alkylboron group having 1 to 40 carbon atoms and substituted with at least one functional group, an arylboron group having 6 to 60 ring carbon atoms, a phosphine group having 1 to 40 ring carbon atoms and substituted with at least one functional group, and a phosphine oxide group having 1 to 40 carbon atoms and substituted with at least one functional group, wherein said functional group is selected from the group consisting of: a cyano group, a nitro group, a trifluoromethyl group, a fluoro group, and a chloro group;
wherein the others of $Z^1$ to $Z^8$, $Z^9$ and $Z^{10}$ are each independently selected from the group consisting of: a hydrogen atom, a deuterium atom, a halogen group, a cyano group, a nitro group, a trifluoromethyl group, an alkyl group having 1 to 40 carbon atoms, an alkenyl

146 group having 2 to 40 carbon atoms, an alkynyl group having 2 to 40 carbon atoms, a cycloalkyl group having 3 to 60 ring carbon atoms, a heterocycloalkyl group having 3 to 60 ring carbon atoms, an aryl group having 6 to 60 ring carbon atoms, a heteroaryl group having 3 to 60 ring carbon atoms, an alkoxy group having 1 to 40 carbon atoms, an aryloxy group having 6 to 60 ring carbon atoms, an alkylsilyl group having 1 to 40 carbon atoms, an arylsilyl group having 6 to 60 ring carbon atoms, an alkylboron group having 1 to 40 carbon atoms, an arylboron group having 6 to 60 ring carbon atoms, a phosphine group having 1 to 40 carbon atoms, and a phosphine oxide group having 1 to 40 carbon atoms.

2. The compound as claimed in claim 1, wherein the compound is represented by

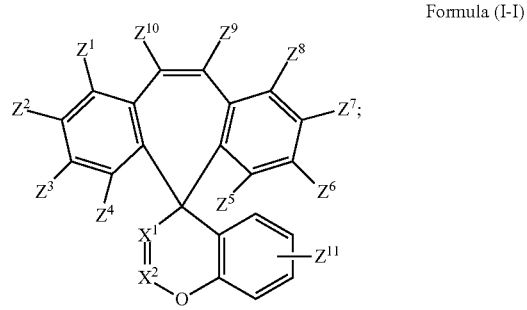

Formula (I-I)

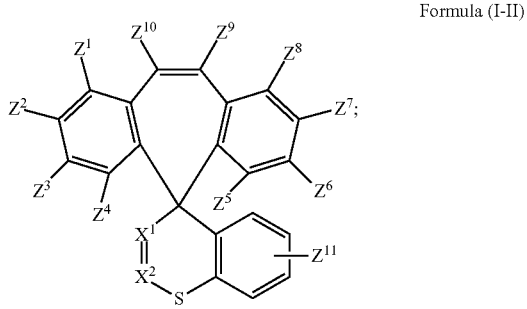

Formula (I-II)

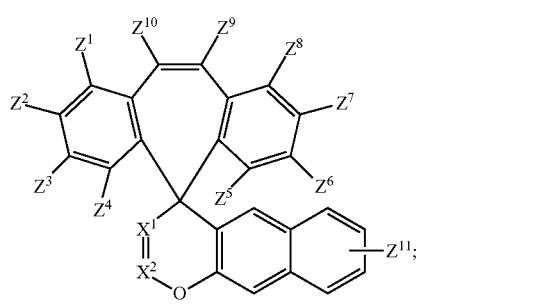

Formula (I-III)

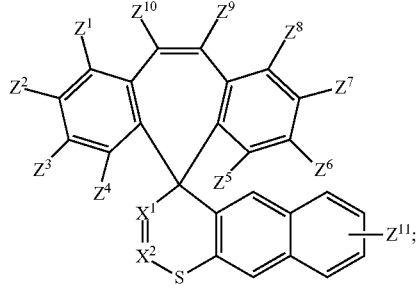

Formula (I-IV)

Formula (I-V)
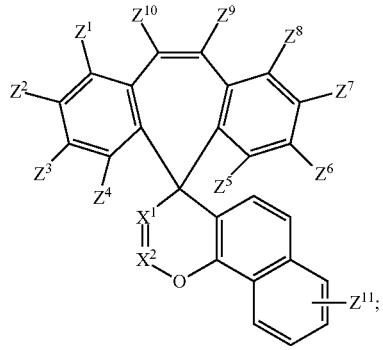
Formula (I-VI)
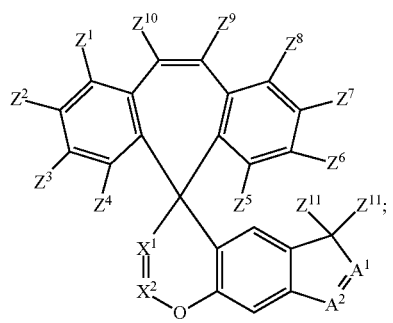
Formula (I-VII)
Formula (I-VIII)
Formula (I-IX)
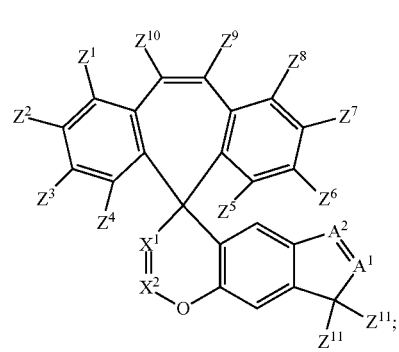
Formula (I-X)
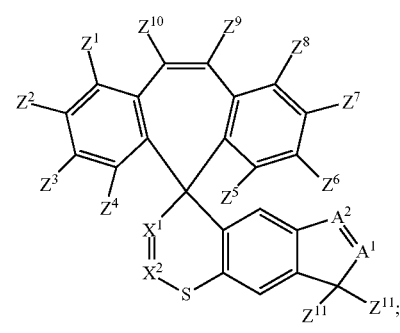
Formula (I-XI)
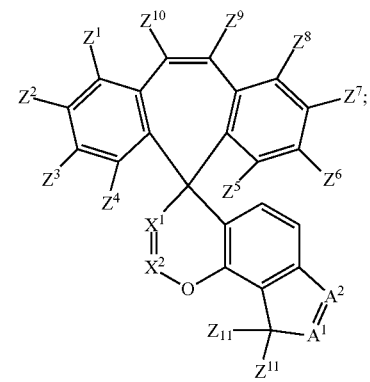
Formula (I-XII)
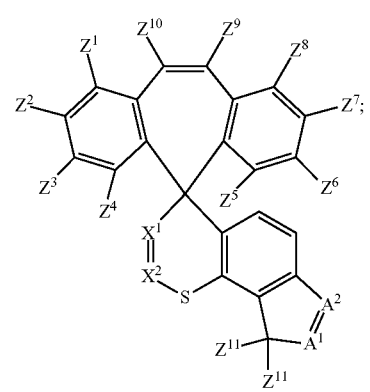

Formula (I-XIII)
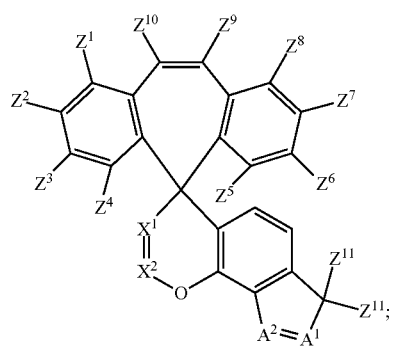
Formula (I-XIV)
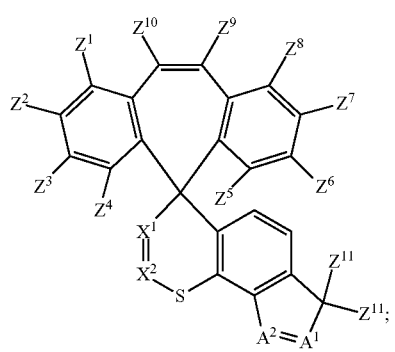
Formula (I-XV)
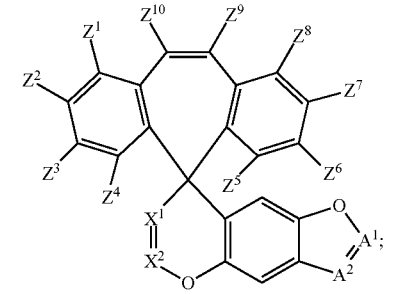
Formula (I-XVI)
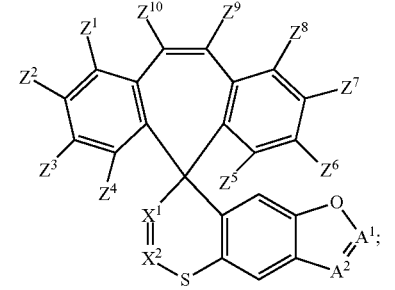
Formula (I-XVII)
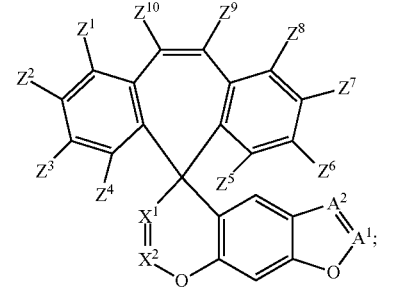
Formula (I-XVIII)
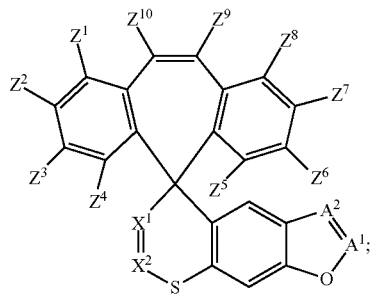
Formula (I-XIX)
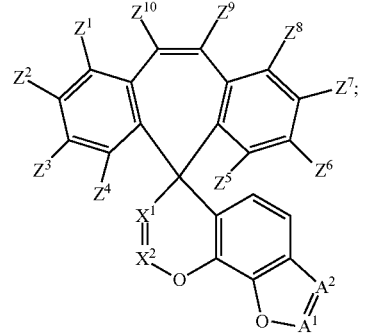
Formula (I-XX)
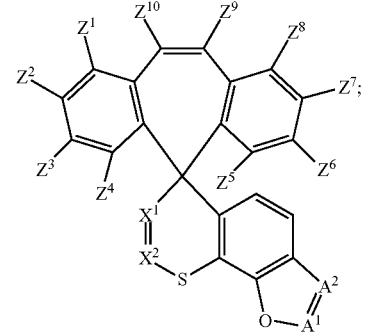
Formula (I-XXI)
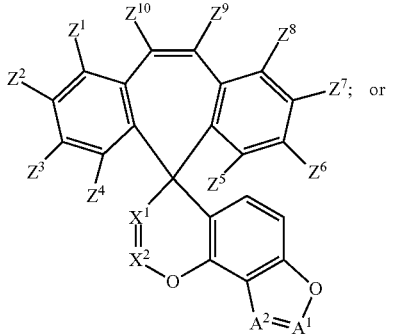

Formula (I-XXII)

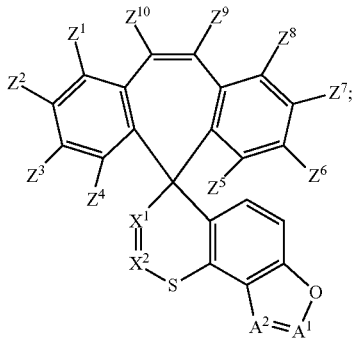

wherein A¹ and A² are each independently C(R$^c$), the two (R$^c$)s are the same or different, and the two (R$^c$)s are joined together to form an aromatic structure contained in the second aryl ring or the heteroaryl ring;

wherein each $Z^{11}$ is selected from the group consisting of: a methyl group, an ethyl group, a propyl group, a butyl group, a pentyl group, a hexyl group, and a phenyl group.

3. The compound as claimed in claim 2, wherein the aromatic structure extended from A¹ and A² is a substituted or unsubstituted 6 to 20-membered carbon aromatic cyclic structure.

4. The compound as claimed in claim 3, wherein the substituted or unsubstituted 6 to 20-membered carbon aromatic cyclic structure is selected from the group consisting of: a substituted or unsubstituted benzene structure, a substituted or unsubstituted naphthalene structure, a substituted or unsubstituted anthracene structure, a substituted or unsubstituted phenanthrene structure, a substituted or unsubstituted pyrene structure, a substituted or unsubstituted fluoranthene structure, a substituted or unsubstituted benzofluoranthene structure, and a substituted or unsubstituted fluorene structure.

5. The compound as claimed in claim 1, wherein the first aryl ring extended from X¹ and X² is a substituted or unsubstituted 6 to 60-membered carbon ring.

6. The compound as claimed in claim 5, wherein the substituted or unsubstituted 6 to 60-membered carbon ring is selected from the group consisting of: a substituted or unsubstituted benzene ring, a substituted or unsubstituted naphthalene ring, a substituted or unsubstituted anthracene ring, a substituted or unsubstituted phenanthrene ring, a substituted or unsubstituted pyrene ring, a substituted or unsubstituted fluoranthene ring, a substituted or unsubstituted benzofluoranthene ring, and a substituted or unsubstituted fluorene structure.

7. The compound as claimed in claim 6, wherein the substituted or unsubstituted 6 to 60-membered carbon ring is a substituted or unsubstituted benzene structure.

8. The compound as claimed in claim 1, wherein at least one of $Z^1$ to $Z^8$ in Formula (I) is selected from the group consisting of:

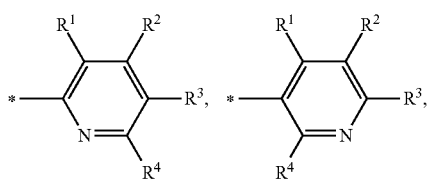

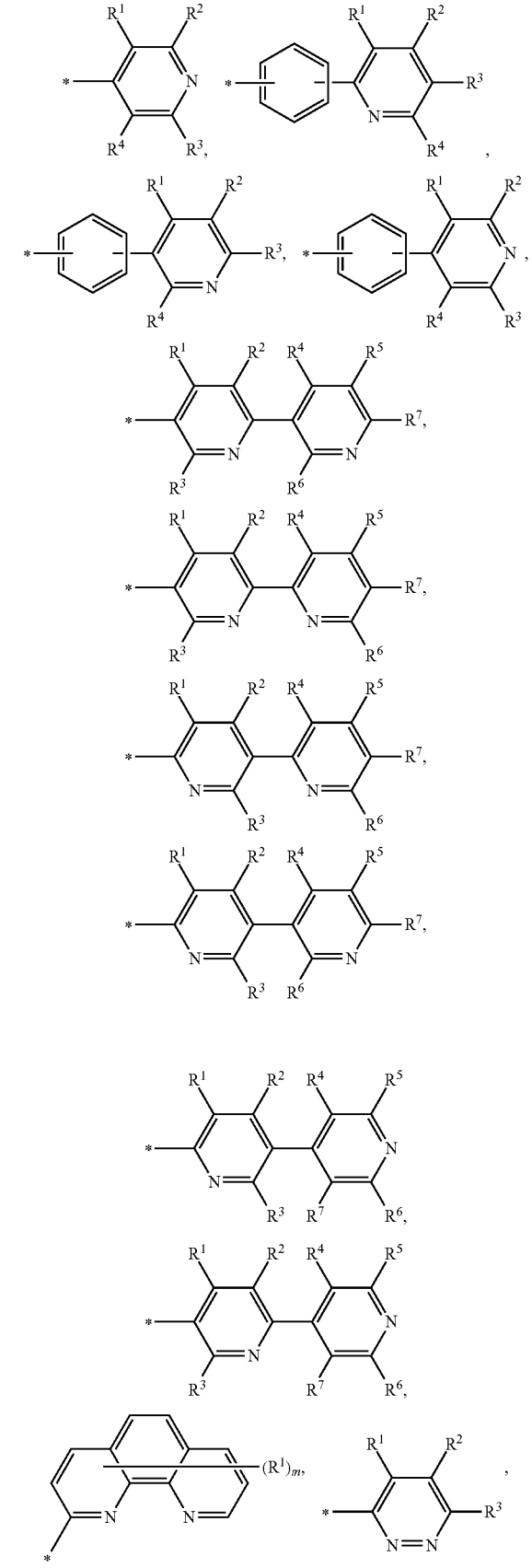

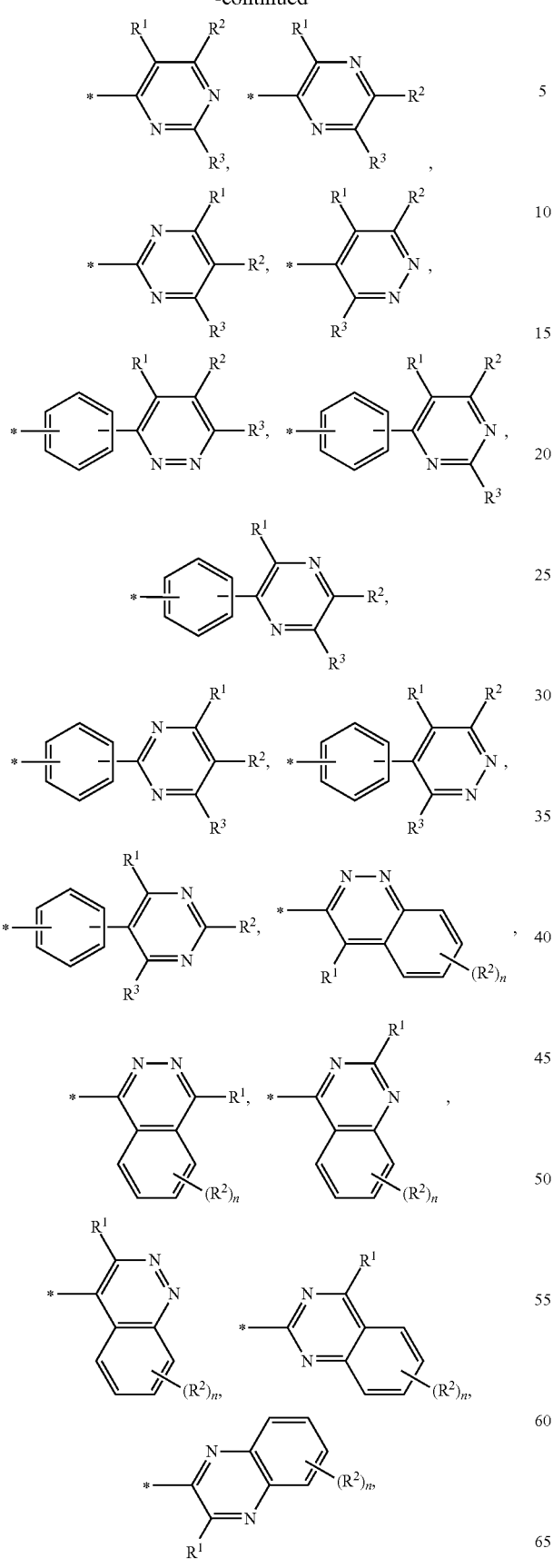
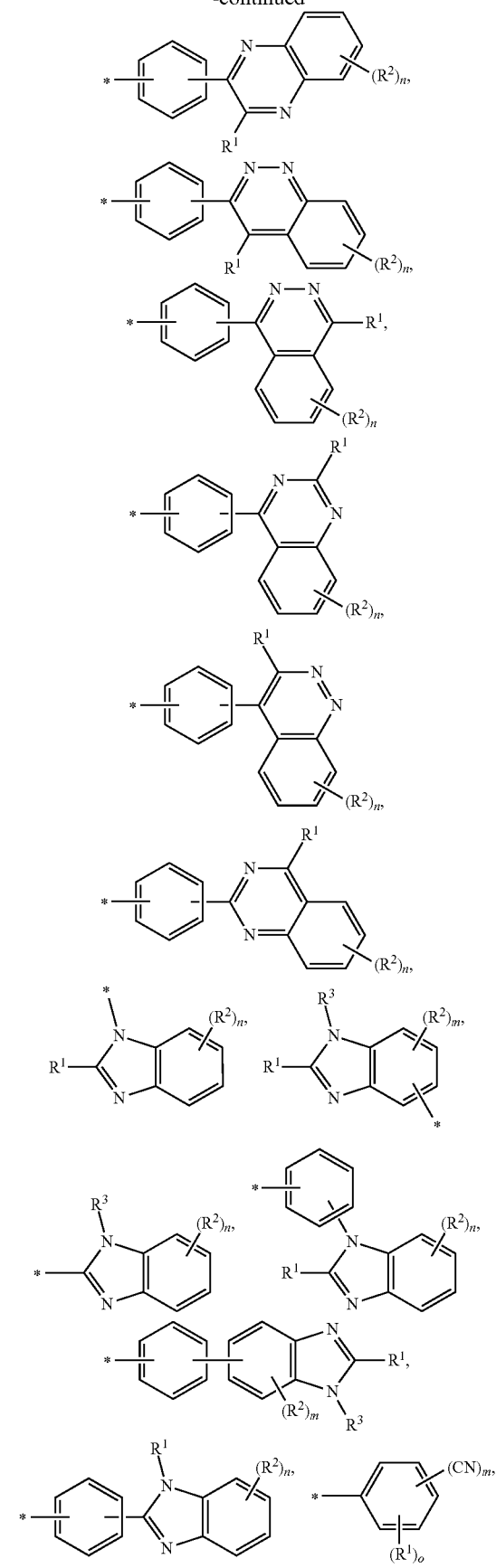

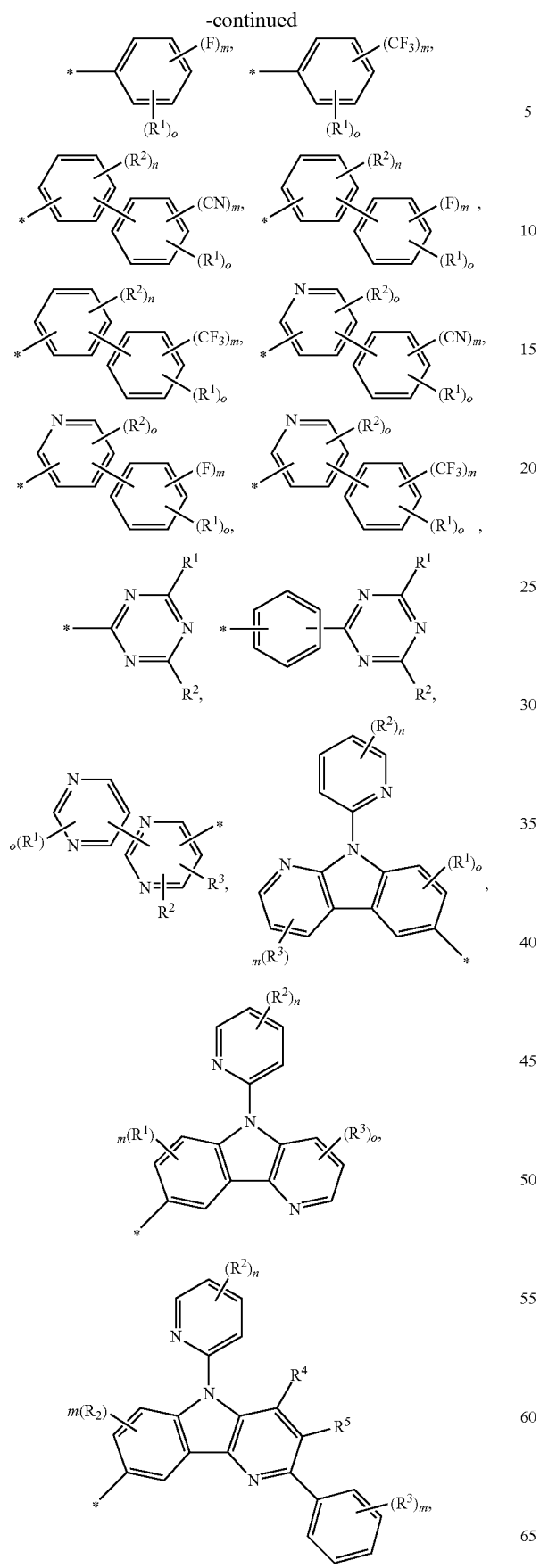

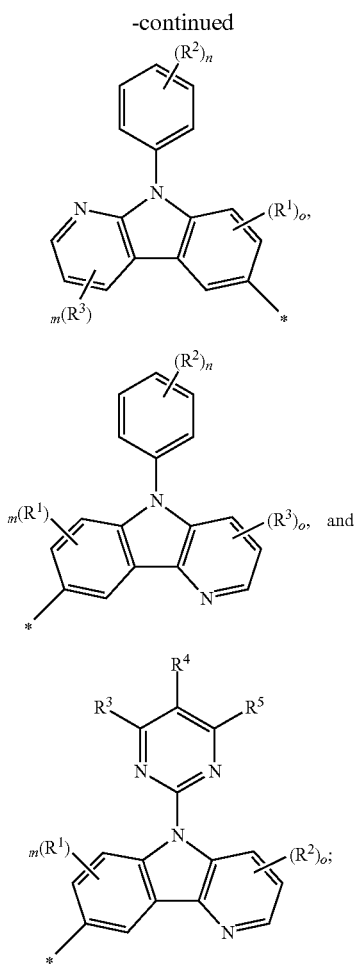

wherein $R^1$ to $R^7$ are each independently selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is an integer from 0 to 4, m is an integer from 0 to 3, o is an integer from 0 to 3, and the total of m and o is not more than 5.

9. The compound as claimed in claim 1, wherein at least one of $Z^2$, $Z^3$, $Z^6$, and $Z^7$ in Formula (I) is selected from the group consisting of:

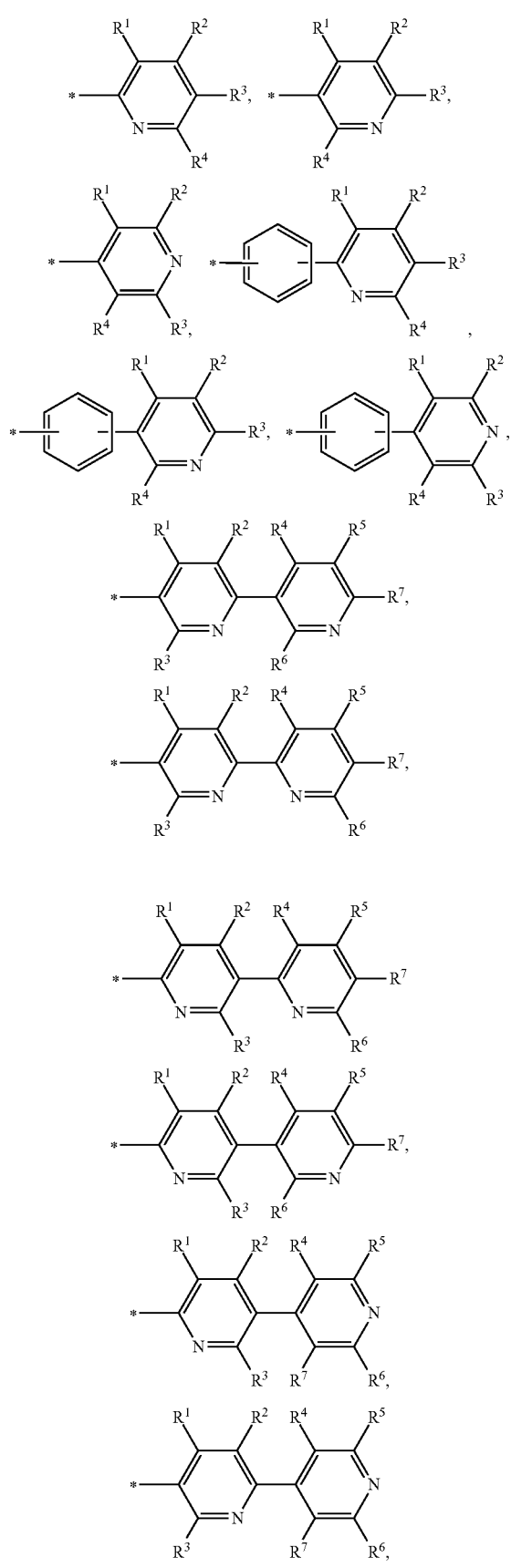
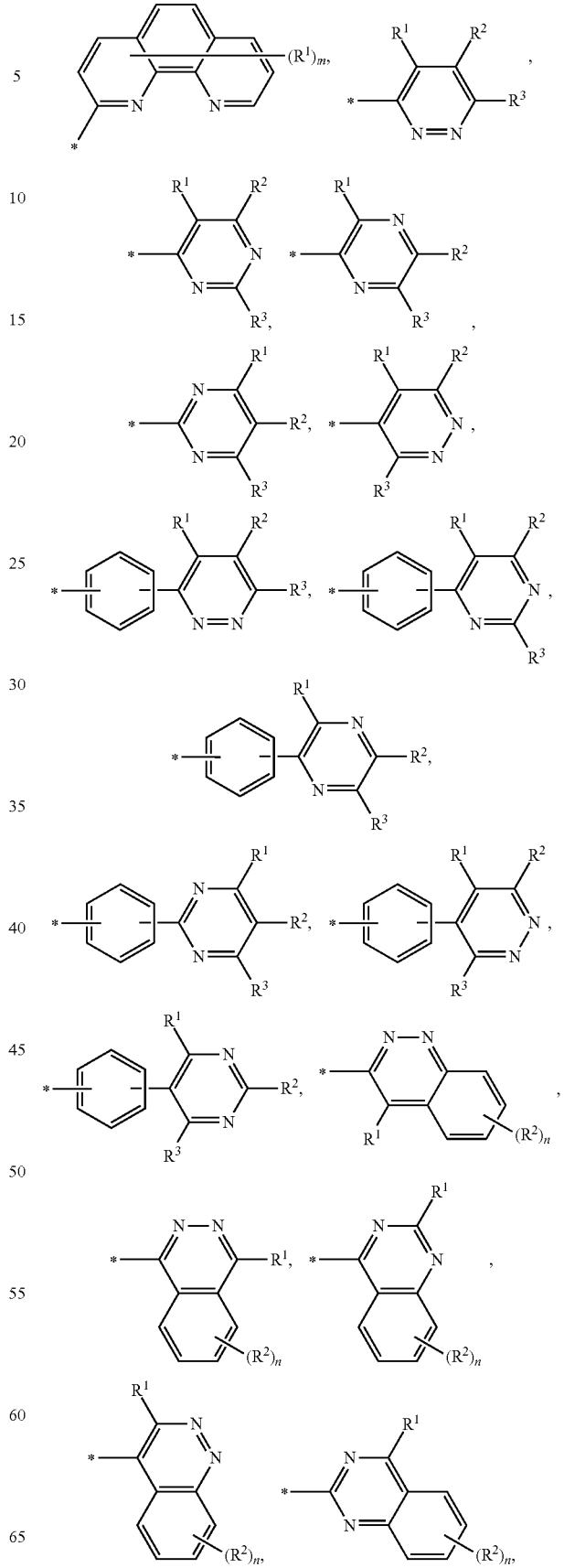
-continued

-continued
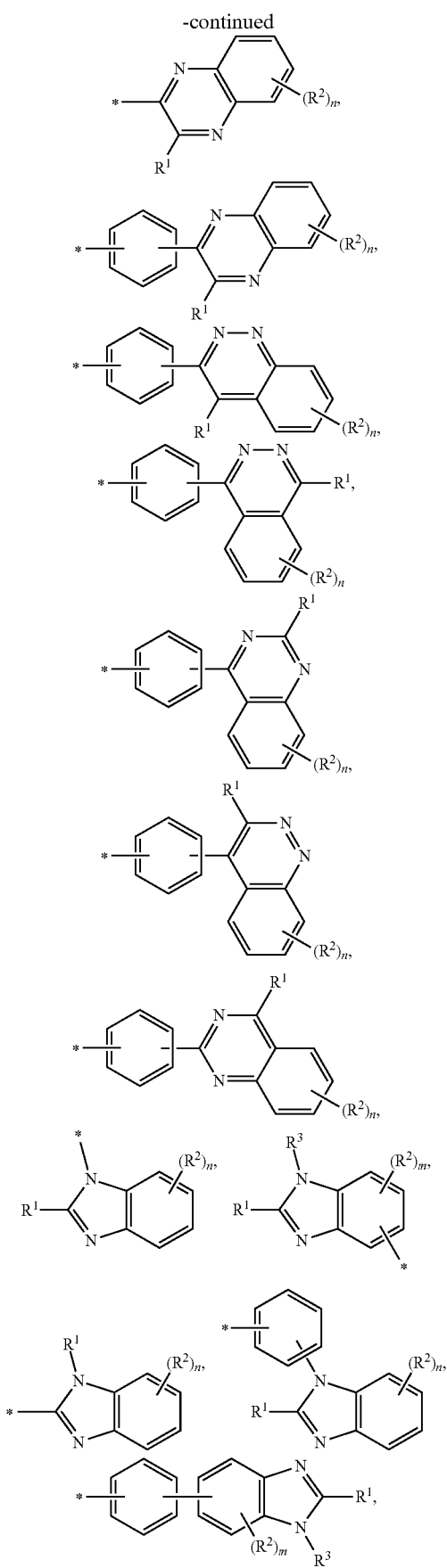
-continued
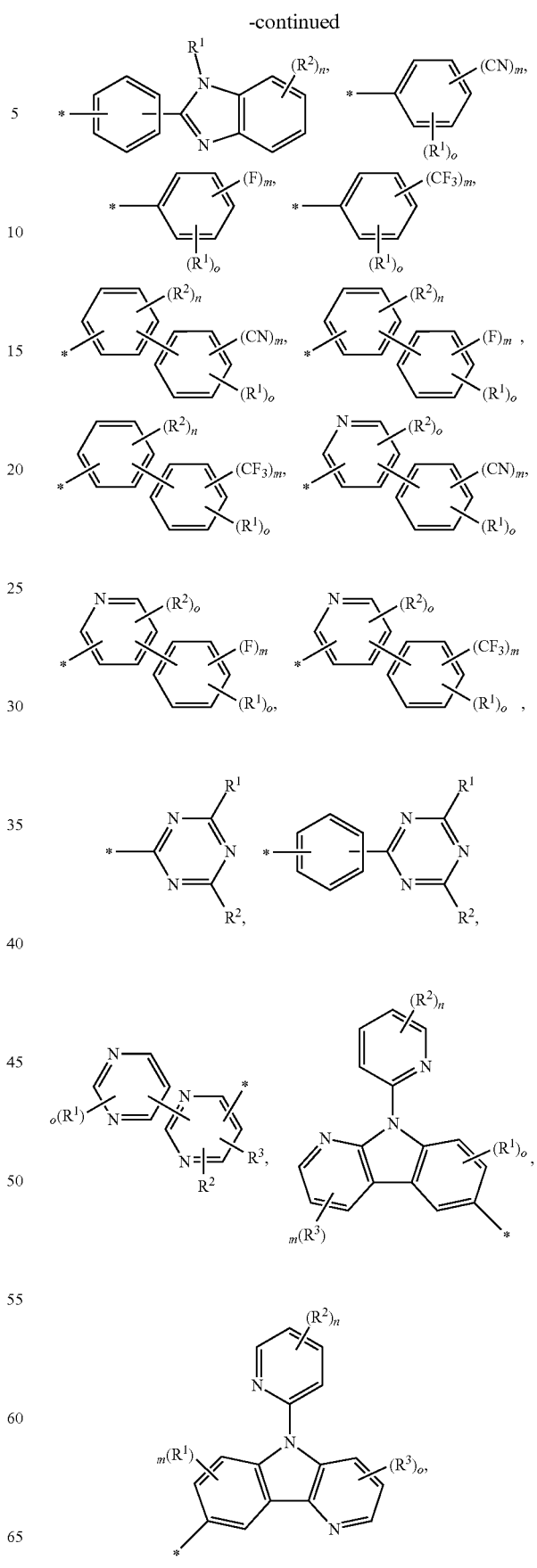

-continued

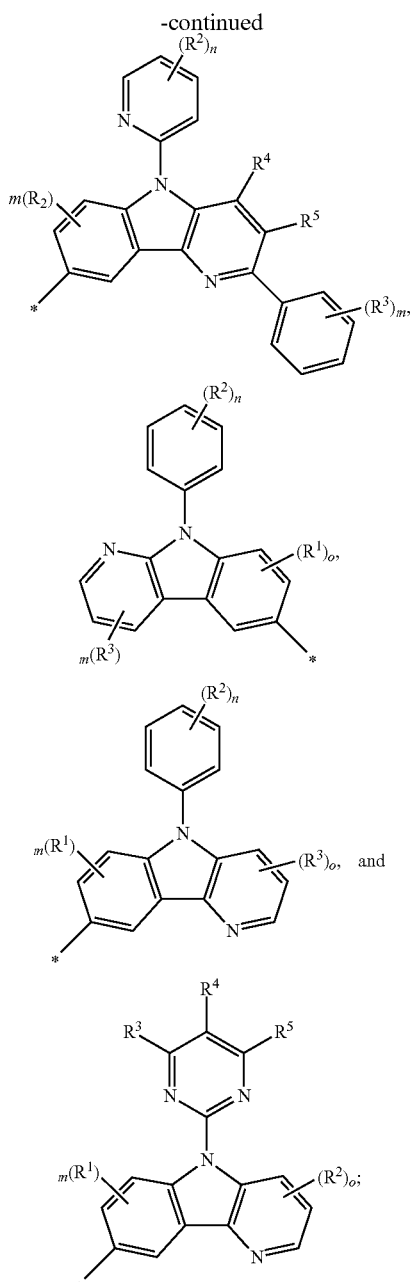

wherein R¹ to R⁷ are each independently selected from the group consisting of: a hydrogen atom, a deuterium atom, a halogen group, a cyano group, a nitro group, a trifluoromethyl group, an alkyl group having 1 to 12 carbon atoms, an alkenyl group having 2 to 12 carbon atoms, an alkynyl group having 2 to 12 carbon atoms, a cycloalkyl group having 3 to 30 ring carbon atoms, a heterocycloalkyl group having 3 to 30 ring carbon atoms, an aryl group having 6 to 30 ring carbon atoms, a heteroaryl group having 3 to 20 ring carbon atoms, an alkoxy group having 1 to 40 carbon atoms, an aryloxy group having 6 to 30 ring carbon atoms, an alkylsilyl group having 1 to 40 carbon atoms, an arylsilyl group having 6 to 30 ring carbon atoms, an alkylboron group having 1 to 40 carbon atoms, an arylboron group having 6 to 30 ring carbon atoms, a phosphine group having 1 to 30 carbon atoms, and a phosphine oxide group having 1 to 30 carbon atoms;

wherein n is an integer from 0 to 4, m is an integer from 0 to 3, o is an integer from 0 to 3, and the total of m and o is not more than 5;

wherein $Z^1$, $Z^4$, $Z^5$, $Z^8$ are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

10. The compound as claimed in claim 1, wherein at least one of $Z^2$, $Z^3$, $Z^6$, and $Z^7$ in Formula (I) is selected from the group consisting of:

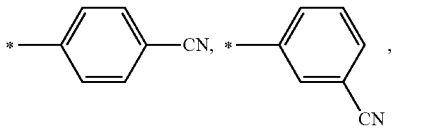

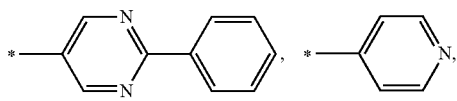

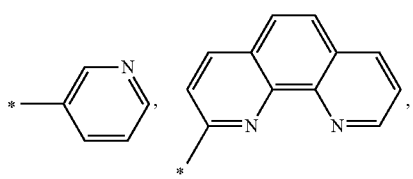

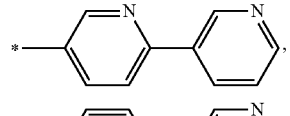

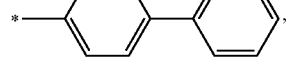

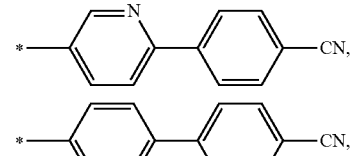

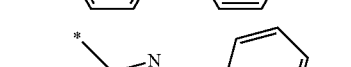

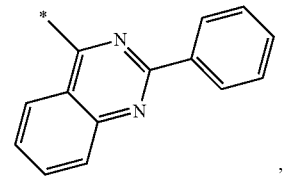

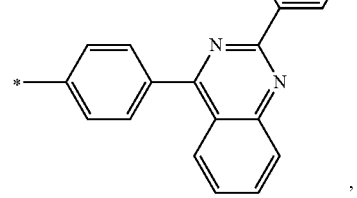

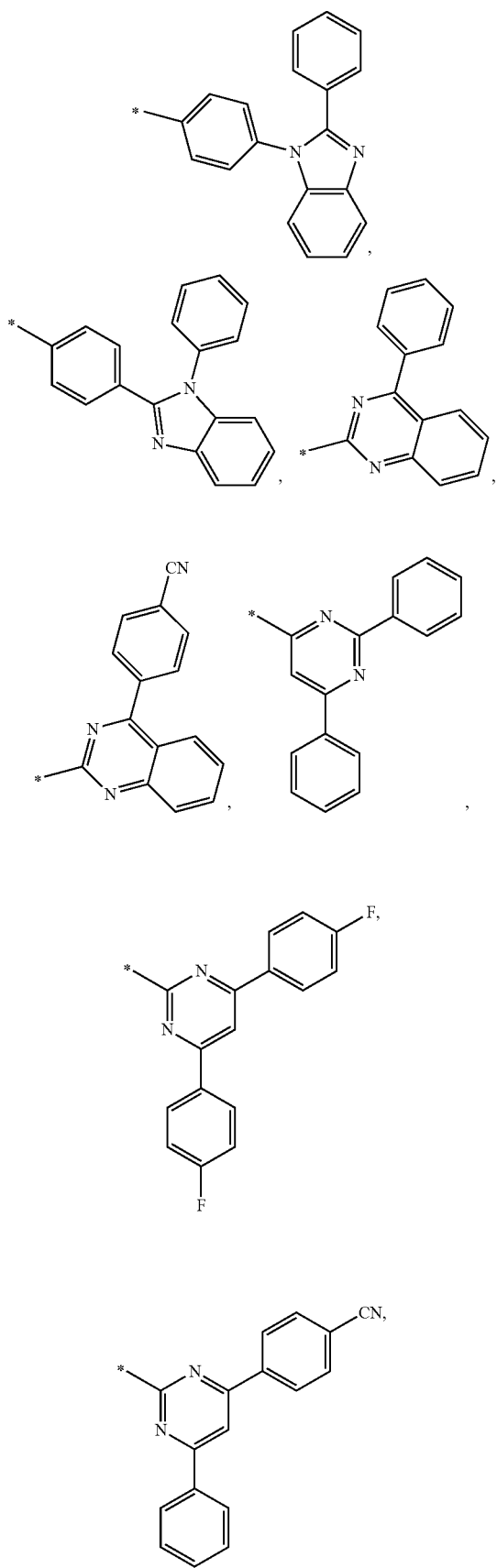
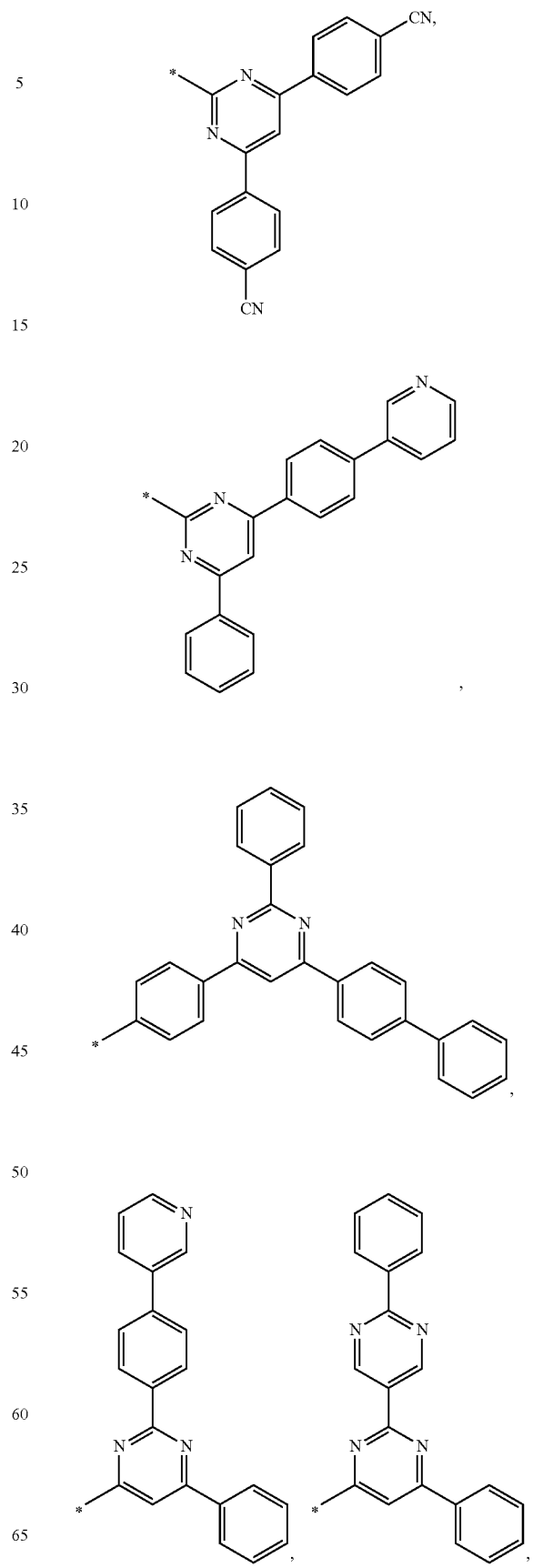

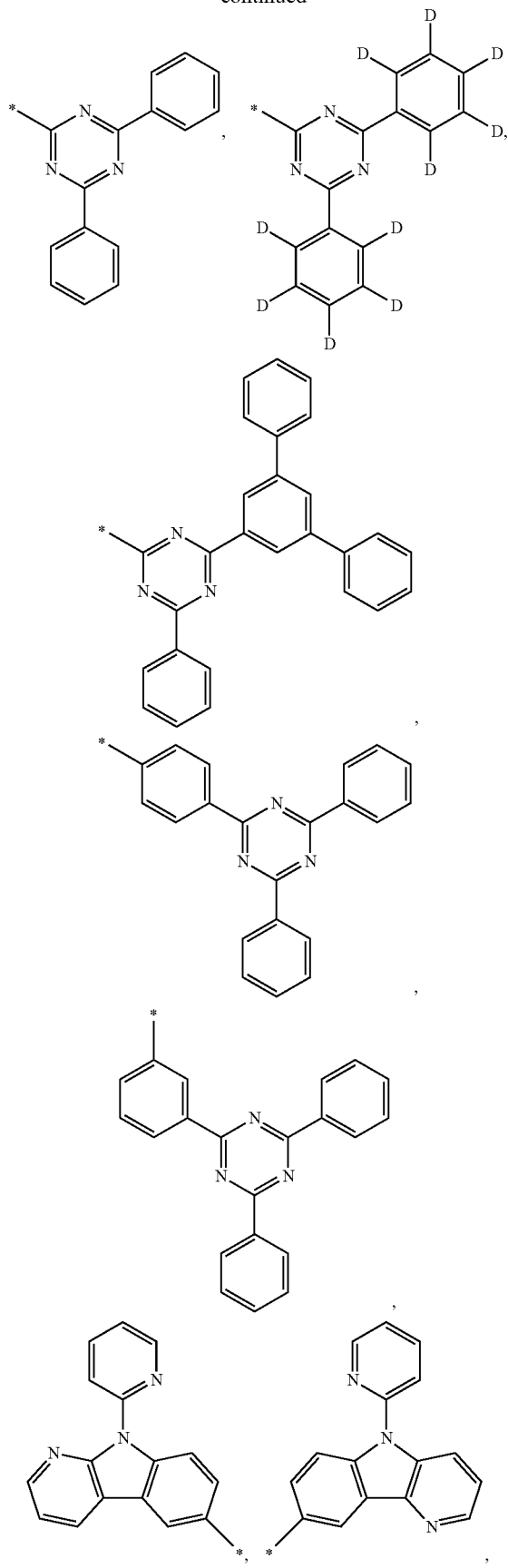

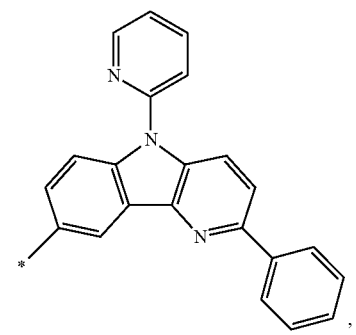

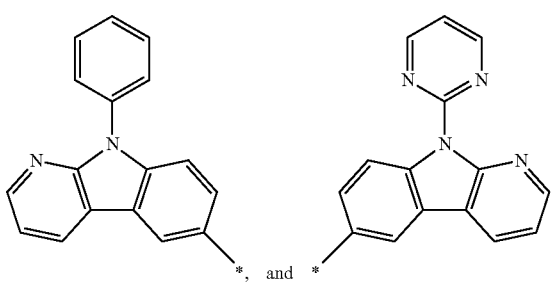

11. The compound as claimed in claim 1, wherein $Z^9$ and $Z^{10}$ in Formula (I) are each independently selected from the group consisting of: a hydrogen atom, a deuterium atom, a halogen group, a cyano group, a nitro group, an alkyl group having 1 to 12 carbon atoms, an alkenyl group having 2 to 12 carbon atoms, and an alkynyl group having 2 to 12 carbon atoms.

12. The compound as claimed in claim 1, wherein the compound is selected from the group consisting of:

Compound 1

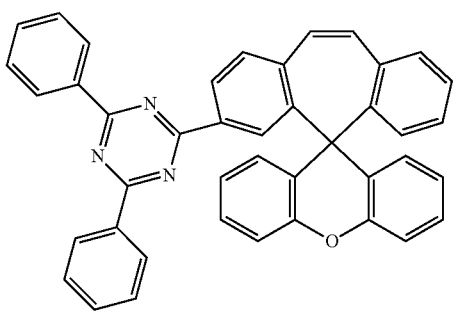

Compound 2

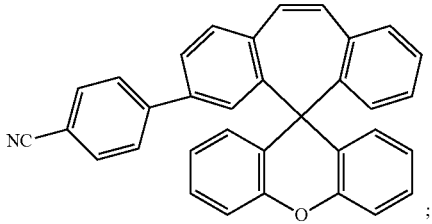

Compound 3
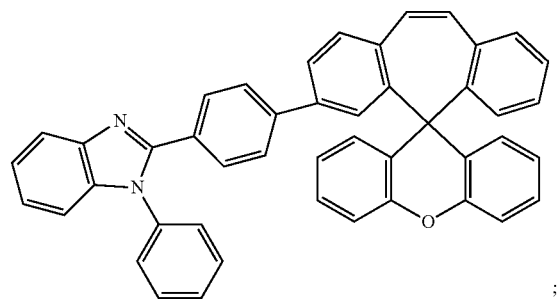
;
Compound 4
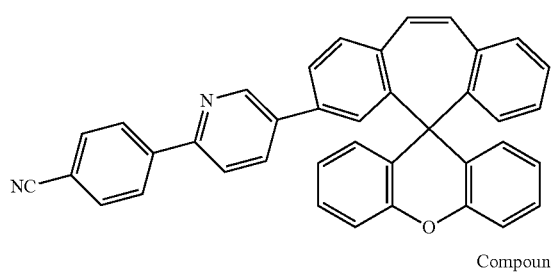
;
Compound 5
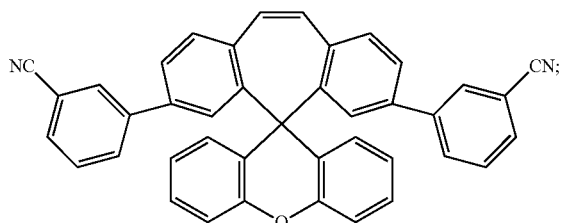
;
Compound 6
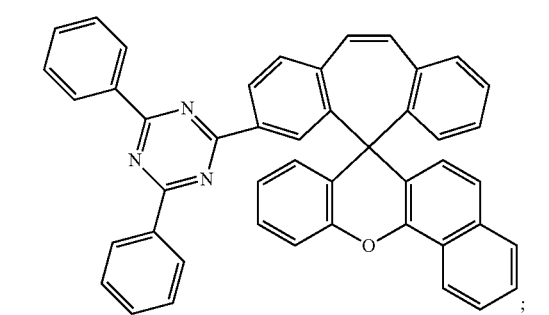
;
Compound 7
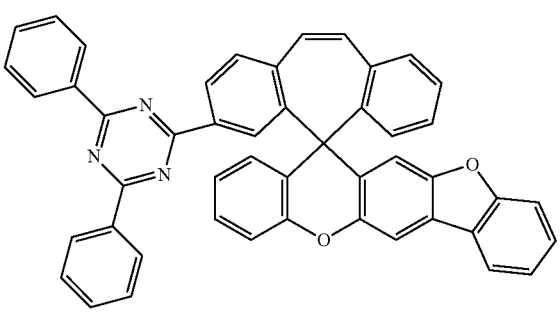
;
Compound 8
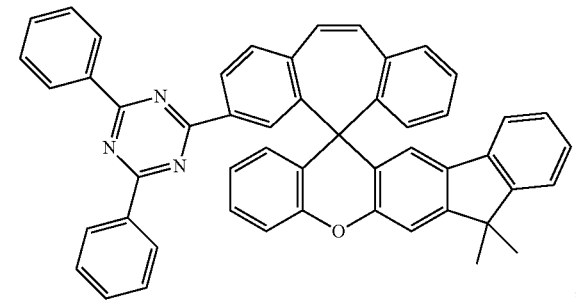
;
Compound 9
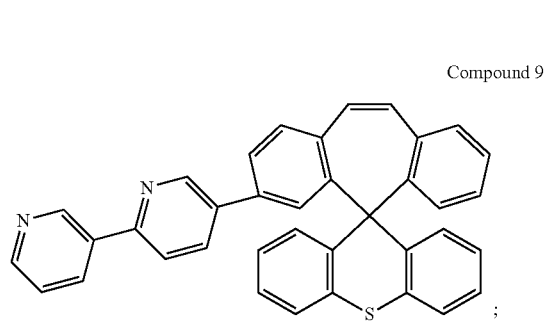
;
Compound 10
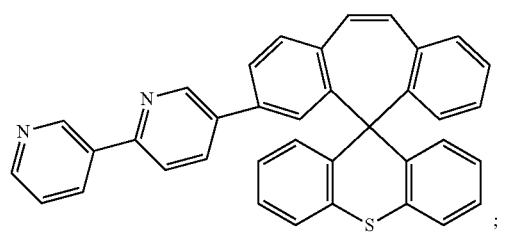
;
Compound 11
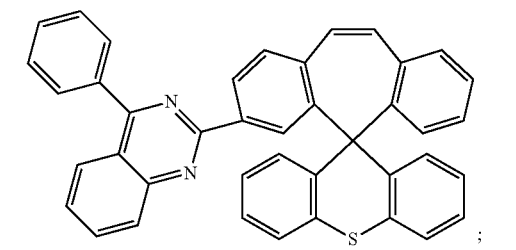
;
Compound 12
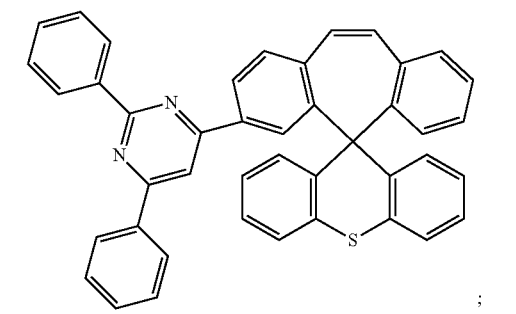
;

-continued

Compound 13

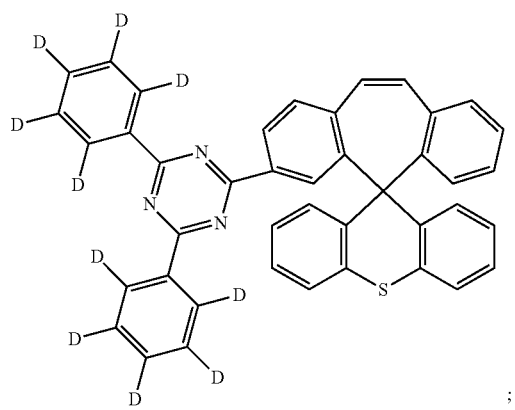

Compound 14

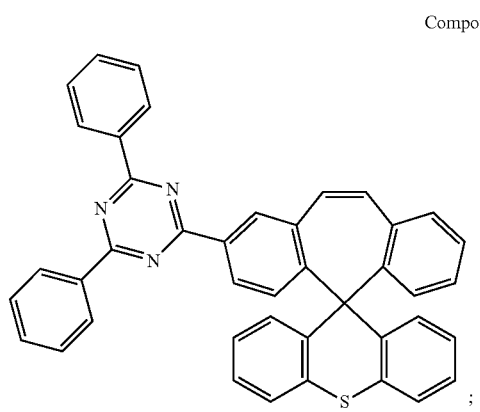

Compound 15

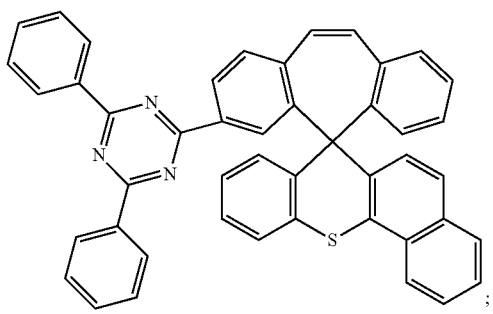

Compound 16

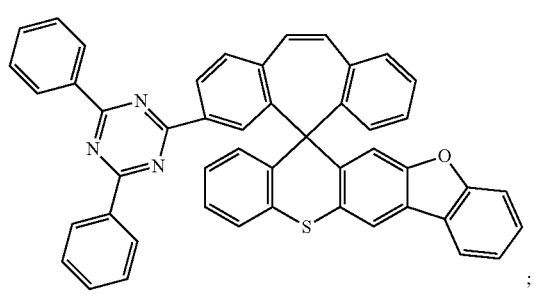

; and

-continued

Compound 17

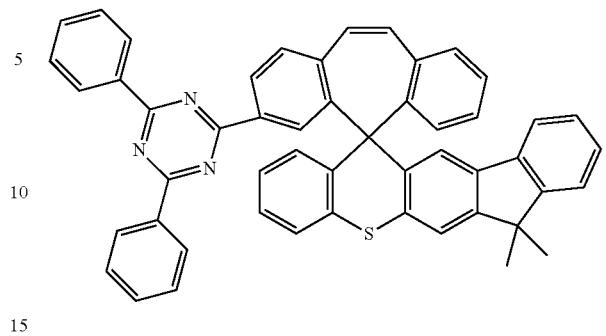

13. An organic electronic device, comprising a first electrode, a second electrode, and an organic layer disposed between the first electrode and the second electrode, wherein the organic layer comprises the compound as claimed in claim 1.

14. The organic electronic device as claimed in claim 13, wherein the organic electronic device is an organic light emitting device.

15. The organic electronic device as claimed in claim 14, wherein the organic light emitting device comprises:
    a hole injection layer formed on the first electrode;
    a hole transport layer formed on the hole injection layer;
    an emission layer formed on the hole transport layer;
    an electron transport layer formed on the emission layer, wherein the organic layer is the electron transport layer; and
    an electron injection layer formed between the electron transport layer and the second electrode.

16. The organic electronic device as claimed in claim 14, wherein the organic light emitting device comprises:
    a hole injection layer formed on the first electrode;
    a hole transport layer formed on the hole injection layer;
    an emission layer formed on the hole transport layer;
    a hole blocking layer formed on the emission layer, wherein the organic layer is the hole blocking layer;
    an electron transport layer formed on the hole blocking layer; and
    an electron injection layer formed between the electron transport layer and the second electrode.

17. The organic electronic device as claimed in claim 13, wherein the compound is selected from the group consisting of:

Compound 1

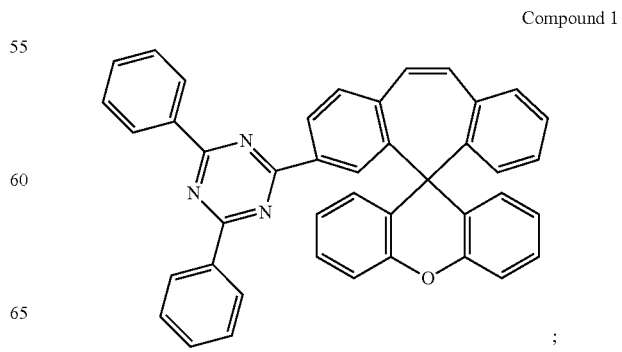

;

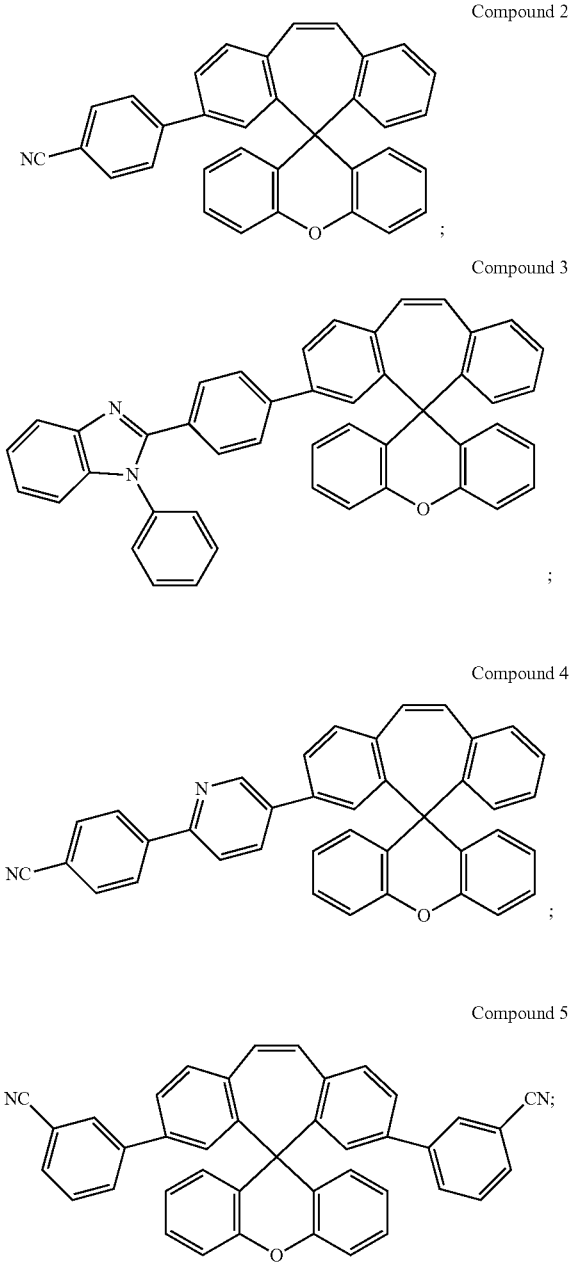
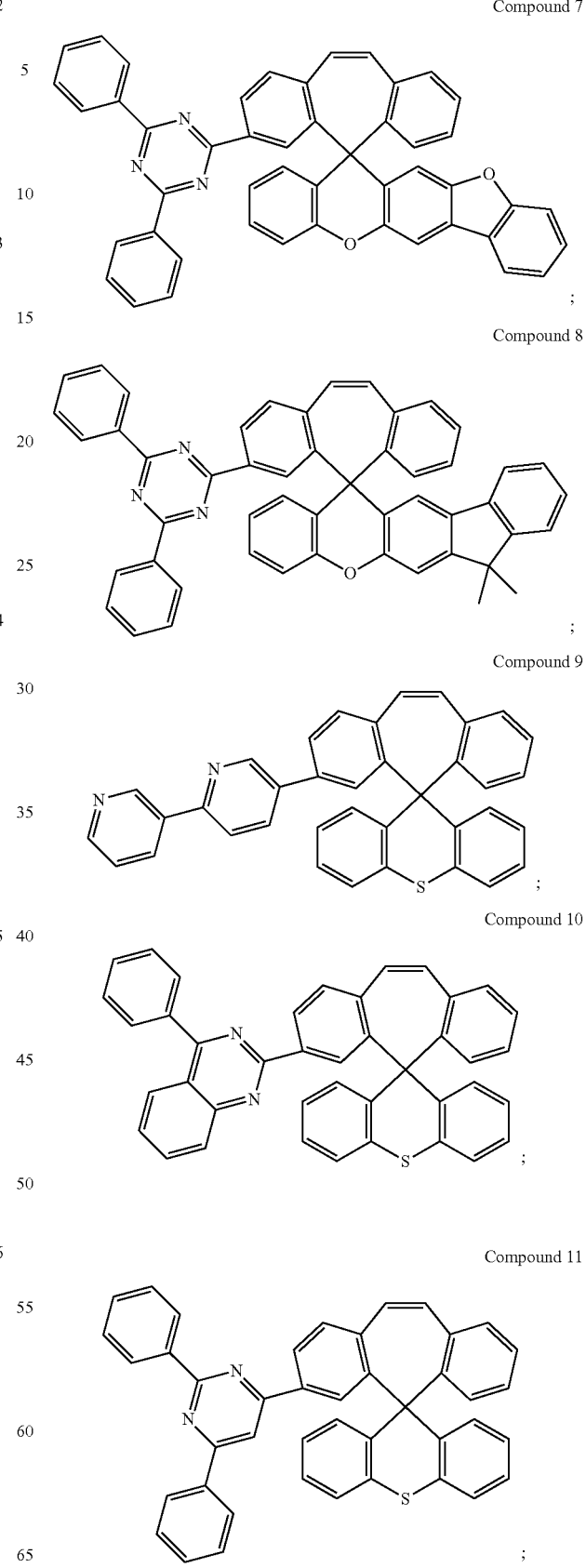

Compound 12
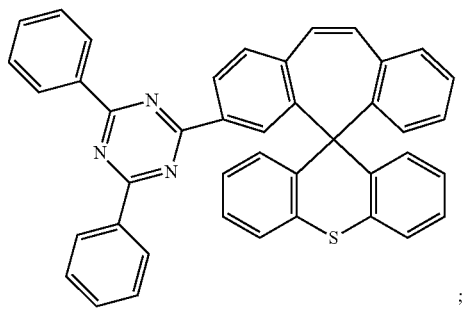
Compound 15
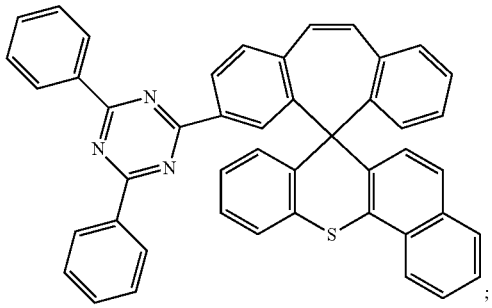
;
Compound 13
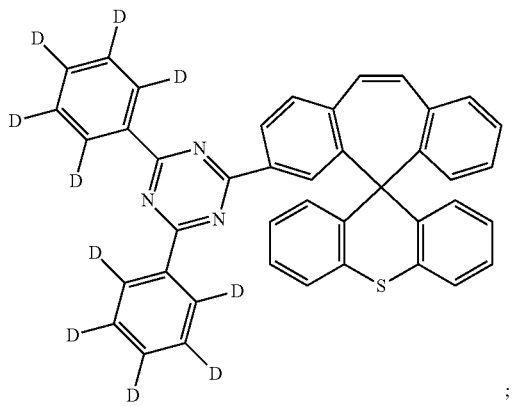
;
Compound 16
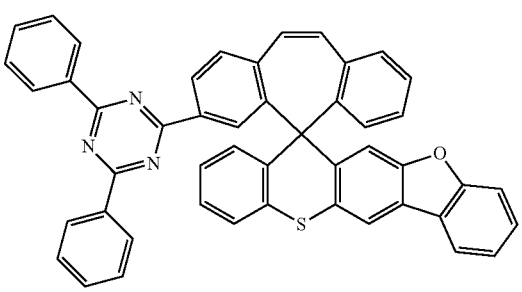
; and
Compound 14
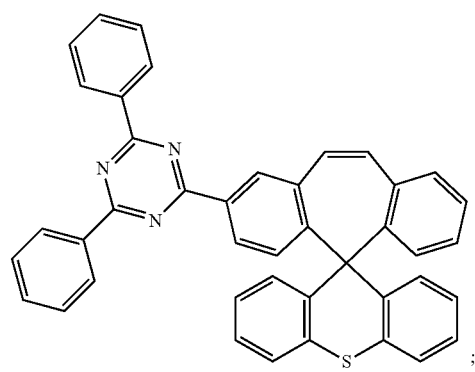
;
Compound 17
* * * * *